(12) United States Patent
Bashan et al.

(10) Patent No.: US 9,220,456 B2
(45) Date of Patent: Dec. 29, 2015

(54) SYSTEMS, METHODS AND DEVICES FOR ACHIEVING GLYCEMIC BALANCE

(75) Inventors: Eran Bashan, Ann Arbor, MI (US); Israel Hodish, Ann Arbor, MI (US)

(73) Assignee: Hygieia, Inc., Ann Arbor, MI (US)

(*) Notice: Subject to any disclaimer, the term of this patent is extended or adjusted under 35 U.S.C. 154(b) by 1192 days.

(21) Appl. No.: 13/168,659

(22) Filed: Jun. 24, 2011

(65) Prior Publication Data

US 2011/0319322 A1 Dec. 29, 2011

Related U.S. Application Data

(63) Continuation-in-part of application No. 12/417,955, filed on Apr. 3, 2009, and a continuation-in-part of application No. 12/417,960, filed on Apr. 3, 2009.

(60) Provisional application No. 61/042,487, filed on Apr. 4, 2008, provisional application No. 61/060,645, filed on Jun. 11, 2008.

(51) Int. Cl.
*G01N 33/48* (2006.01)
*G01N 31/00* (2006.01)
(Continued)

(52) U.S. Cl.
CPC ............ *A61B 5/4839* (2013.01); *A61B 5/14532* (2013.01); *G06F 19/3468* (2013.01); *A61B 5/0002* (2013.01); *A61M 5/142* (2013.01); *A61M 5/1723* (2013.01)

(58) Field of Classification Search
CPC .. A61B 5/145; A61B 5/14532; A61B 5/4839; G06F 19/30; G06F 19/3437; G06F 19/3487
See application file for complete search history.

(56) References Cited

U.S. PATENT DOCUMENTS

| 4,403,984 A | 9/1983 | Ash et al. |
| 4,731,726 A | 3/1988 | Allen |

(Continued)

FOREIGN PATENT DOCUMENTS

| WO | 03/065033 | 8/2003 |
| WO | 2005/072792 | 8/2005 |

(Continued)

OTHER PUBLICATIONS

Bu, Davis et al. "Benefits of Information Technology-Enabled Diabetes Management," *Diabetes Care*, 30:5 (May 2007) 1137-1142.

(Continued)

*Primary Examiner* — Larry D Riggs, II
(74) *Attorney, Agent, or Firm* — Jones Day

(57) ABSTRACT

Systems, methods and/or devices for optimizing a patient's insulin dosage regimen over time, comprising at least a first memory for storing data inputs corresponding at least to one or more components in a patient's present insulin dosage regimen, and data inputs corresponding at least to the patient's blood-glucose-level measurements determined at a plurality of times, and a processor operatively connected to the at least first memory. The processor is programmed at least to determine from the data inputs corresponding to the patient's blood-glucose-level measurements determined at a plurality of times whether and by how much to vary at least one of the one or more components in the patient's present insulin dosage regimen. Also disclosed are systems, methods and/or devices for treating a patient's diabetes by providing treatment guidance, wherein the patient's current glycemic state is determined relative to a desired balance point; and determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before increasing the frequency of hypoglycemic events above a predetermined threshold.

30 Claims, 23 Drawing Sheets

(51) Int. Cl.

| | | |
|---|---|---|
| *G06G 7/48* | (2006.01) | |
| *G06G 7/58* | (2006.01) | |
| *A61B 5/00* | (2006.01) | |
| *A61B 5/145* | (2006.01) | |
| *G06F 19/00* | (2011.01) | |
| *A61M 5/142* | (2006.01) | |
| *A61M 5/172* | (2006.01) | |

(56) References Cited

U.S. PATENT DOCUMENTS

| | | | |
|---|---|---|---|
| 4,981,779 | A | 1/1991 | Wagner |
| 5,216,597 | A | 6/1993 | Beckers |
| 5,251,126 | A | 10/1993 | Kahn et al. |
| 5,822,715 | A * | 10/1998 | Worthington et al. ......... 702/19 |
| 5,840,020 | A | 11/1998 | Heinonen et al. |
| 5,956,501 | A | 9/1999 | Brown |
| 6,024,699 | A | 2/2000 | Surwit et al. |
| 6,186,145 | B1 | 2/2001 | Brown |
| 6,233,539 | B1 | 5/2001 | Brown |
| 6,379,301 | B1 | 4/2002 | Worthington et al. |
| 6,540,672 | B1 | 4/2003 | Simonsen et al. |
| 6,544,212 | B2 | 4/2003 | Galley et al. |
| 6,560,471 | B1 * | 5/2003 | Heller et al. .................. 600/347 |
| 6,565,114 | B1 | 5/2003 | Thomas |
| 6,575,905 | B2 | 6/2003 | Knobbe et al. |
| 6,669,663 | B1 | 12/2003 | Thompson |
| 6,740,072 | B2 | 5/2004 | Starkweather et al. |
| 7,025,425 | B2 | 4/2006 | Kovatchev et al. |
| 7,039,560 | B2 | 5/2006 | Kawatahara et al. |
| 7,060,059 | B2 | 6/2006 | Keith et al. |
| 7,108,680 | B2 | 9/2006 | Rohr et al. |
| 7,137,951 | B2 | 11/2006 | Pilarski |
| 7,167,818 | B2 | 1/2007 | Brown |
| 7,204,823 | B2 | 4/2007 | Estes et al. |
| 7,267,665 | B2 | 9/2007 | Steil et al. |
| 7,282,029 | B1 | 10/2007 | Poulsen et al. |
| 7,291,107 | B2 | 11/2007 | Hellwig et al. |
| 7,404,796 | B2 | 7/2008 | Ginsberg |
| 7,509,156 | B2 | 3/2009 | Flanders |
| 7,553,281 | B2 | 6/2009 | Hellwig et al. |
| 7,651,845 | B2 | 1/2010 | Doyle et al. |
| 7,734,323 | B2 | 6/2010 | Blomquist |
| H2246 | H * | 8/2010 | Miller et al. .................. 600/365 |
| 7,853,455 | B2 | 12/2010 | Brown |
| 7,877,271 | B2 | 1/2011 | Brown |
| 7,901,625 | B2 | 3/2011 | Brown |
| 7,904,310 | B2 | 3/2011 | Brown |
| 7,912,688 | B2 | 3/2011 | Brown |
| 7,920,998 | B2 | 4/2011 | Brown |
| 7,949,507 | B2 | 5/2011 | Brown |
| 2003/0028089 | A1 | 2/2003 | Galley et al. |
| 2003/0050621 | A1 | 3/2003 | Lebel et al. |
| 2003/0216628 | A1 * | 11/2003 | Bortz et al. .................. 600/365 |
| 2004/0042272 | A1 | 3/2004 | Kurata |
| 2004/0044272 | A1 | 3/2004 | Moerman et al. |
| 2004/0054263 | A1 | 3/2004 | Moerman et al. |
| 2005/0049179 | A1 | 3/2005 | Davidson et al. |
| 2005/0055010 | A1 | 3/2005 | Pettis et al. |
| 2005/0171503 | A1 | 8/2005 | Van Den Berghe et al. |
| 2005/0177398 | A1 | 8/2005 | Watanabe et al. |
| 2005/0192494 | A1 | 9/2005 | Ginsberg |
| 2005/0192557 | A1 | 9/2005 | Brauker et al. |
| 2005/0197533 | A1 | 9/2005 | May et al. |
| 2005/0197621 | A1 | 9/2005 | Poulsen et al. |
| 2005/0272640 | A1 | 12/2005 | Doyle et al. |
| 2006/0160722 | A1 | 7/2006 | Green et al. |
| 2006/0173260 | A1 | 8/2006 | Gaoni et al. |
| 2006/0224109 | A1 | 10/2006 | Steil et al. |
| 2006/0264886 | A9 | 11/2006 | Pettis et al. |
| 2007/0078314 | A1 | 4/2007 | Grounsell et al. |
| 2007/0078818 | A1 | 4/2007 | Zivitz et al. |
| 2007/0168224 | A1 | 7/2007 | Letzt et al. |
| 2007/0293742 | A1 | 12/2007 | Simonsen et al. |
| 2008/0077072 | A1 | 3/2008 | Keenan et al. |
| 2008/0097289 | A1 | 4/2008 | Steil et al. |
| 2008/0119705 | A1 | 5/2008 | Patel et al. |
| 2008/0139907 | A1 | 6/2008 | Rao et al. |
| 2008/0172030 | A1 | 7/2008 | Blomquist |
| 2008/0214919 | A1 | 9/2008 | Harmon et al. |
| 2008/0234943 | A1 | 9/2008 | Ray et al. |
| 2008/0269585 | A1 | 10/2008 | Ginsberg |
| 2009/0069636 | A1 | 3/2009 | Zivitz et al. |
| 2009/0247982 | A1 | 10/2009 | Krulevitch et al. |
| 2009/0253970 | A1 | 10/2009 | Bashan |
| 2009/0253973 | A1 | 10/2009 | Bashan |
| 2009/0299152 | A1 | 12/2009 | Taub et al. |
| 2010/0016700 | A1 | 1/2010 | Sieh et al. |
| 2010/0124996 | A1 | 5/2010 | Lindsay |
| 2010/0160740 | A1 | 6/2010 | Cohen et al. |
| 2010/0161236 | A1 | 6/2010 | Cohen et al. |
| 2010/0161346 | A1 | 6/2010 | Getschmann et al. |
| 2010/0256047 | A1 | 10/2010 | Sieh et al. |
| 2010/0305545 | A1 | 12/2010 | Kanderian et al. |
| 2010/0331652 | A1 | 12/2010 | Groll et al. |
| 2010/0331654 | A1 | 12/2010 | Jerdonek et al. |

FOREIGN PATENT DOCUMENTS

| | | |
|---|---|---|
| WO | 2005/110222 | 11/2005 |
| WO | 2007/116226 | 10/2007 |
| WO | 2009/146119 | 12/2009 |
| WO | 2009/146121 | 12/2009 |
| WO | 2010/056718 | 5/2010 |
| WO | 2010/075350 | 7/2010 |
| WO | 2010/089304 | 8/2010 |
| WO | 2010/089305 | 8/2010 |
| WO | 2010/089306 | 8/2010 |
| WO | 2010/089307 | 8/2010 |

OTHER PUBLICATIONS

Hayes, R. P. et al. "Primary Care Physician Beliefs About Insulin Initiation in Patients with Type 2 Diabetes," *Int J Clin Pract*, 62:6 (Jun. 2008) 860-868.

Bretzel, Reinhard G. et al. "Once-Daily Basal Insulin Glargine Versus Thrice-Daily Prandial Insulin Lispro in People with Type 2 Diabetes on Oral Hypoglycaemic Agents (APOLLO): An Open Randomised Controlled Trial," *Lancet*, 371 (2008) 1073-1084.

Bergenstal, Richard M. et al. "Adjust to Target in Type 2 Diabetes: Comparison of a Simple Algorithm with Carbohydrate Counting for Adjustment of Mealtime Insulin Glulisine," *Diabetes Care*, 31:7 (Jul. 2008) 1305-1310.

Deutsch, T. et al. "UTOPIA: A Consultation System for Visit-by-Visit Diabetes Management," *Med Inform*, 21:4 (1996) 345-358.

Albisser, A. M. "Devices for the Control of Diabetes Mellitus," *Proceedings of the IEEE*, 67:9 (Sep. 1979) 1308-1320.

Deutsch, T. et al. "Computer-Assisted Diabetic Management: A Complex Approach," *Computer Methods and Programs in BioMedicine*, 32 (1990) 195-214.

Farmer, Terry G., Jr. et al. "The Future of Open- and Closed-Loop Insulin Delivery Systems," *Journal of Pharmacy and Pharmacology*, 60 (2008) 1-13.

Cramer, J. A. et al. "The Significance of Compliance and Persistence in the Treatment of Diabetes, Hypertension and Dyslipidaemia: A Review," *Int J Clin Pract*, 62:1 (Jan. 2008) 76-87.

American Diabetes Association Statement, "Economic Costs of Diabetes in the U.S. in 2007," *Diabetes Care*, 31:3 (Mar. 2008) 596-615.

Andreassen, Steen et al. "A Probabilistic Approach to Glucose Prediction and Insulin Dose Adjustment: Description of Metabolic Model and Pilo Evaluation Study," *Computer Methods and Programs in BioMedicine*, 41 (1994) 153-165.

Day, J. P. "Some Considerations of Legal Liability Concerning the Use and Future Development of Knowledge Based or Expert Systems in Diabetes Care," *Diab Nutr Metab*, 8:4 (1995) 195-200.

Chiarelli, Francesco et al. "Controlled Study in Diabetic Children Comparing Insulin-Dosage Adjustment by Manual and Computer Algorithms," *Diabetes Care*, 13:10 (Oct. 1990) 1080-1088.

Nathan, David M. et al. "Translating the A1C Assay into Estimated Average Glucose Values," *Diabetes Care*, 31:8 (Aug. 2008) 1-6.

(56) References Cited

OTHER PUBLICATIONS

Deutsch, T. et al. "Time Series Analysis and Control of Blood Glucose Levels in Diabetic Patients," *Computer Methods and Programs in BioMedicine*, 41 (1994) 167-182.
Ray, Kausik K. et al. "Effect of Intensive Control of Glucose on Cardiovascular Outcomes and Death in Patients with Diabetes Mellitus: a Meta-Analysis of Randomized Controlled Trials," *Lancet*, 373 (May 23, 2009) 1765-1772.
Ryff-de Léche, Arnika et al. "Clinical Application of Two Computerized Diabetes Management Systems: Comparison with the Log-Book Method," *Diabetes Research*, 19 (1992) 97-105.
Janka, Hans U. et al. "Comparison of Basal Insulin Added to Oral Agents Versus Twice-Daily Premixed Insulin as Initial Insulin Therapy for Type 2 Diabetes," *Diabetes Care*, 28:2 (Feb. 2005) 254-259.
Lougheed, W. D. et al. "Stabilizing Blood Glucose with a Novel Medical Expert System," *Biosensors*, 3 (1988) 381-389.
Pernick, Nat L. et al. "Personal Computer Programs to Assist with Self-Monitoring of Blood Glucose and Self-Adjustment of Insulin Dosage," *Diabetes Care*, 9:1 (Jan.-Feb. 1986) 61-69.
Spoelstra, José A. et al. "Refill Compliance in Type 2 Diabetes Mellitus: A Predictor of Switching to Insulin Therapy?" *Pharmacoepidemiology and Drug Safety*, 12 (2003) 121-127.
Marshall, Trevor G. et al. "New Microprocessor-Based Insulin Controller," *IEEE Transactions on BioMedical Engineering*, BME-30:11 (Nov. 1983) 689-695.
Barnett, Anthony "Dosing of Insulin Glargine in the Treatment of Type 2 Diabetes," *Clinical Therapeutics*, 29:6 (Jun. 2007) 987-999.
Herman, William H. et al. "A Clinical Trial of Continuous Subcutaneous Insulin Infusion Versus Multiple Daily Injections in Older Adults with Type 2 Diabetes," *Diabetes Care*, 28:7 (Jul. 2005) 1568-1573.
Eliaschewitz, Freddy G. et al. "Therapy in Type 2 Diabetes: Insulin Glargine vs. NPH Insulin Both in Combination with Glimepiride," *Archives of Medical Research*, 37 (2006) 495-501.
Hoerger, Thomas J. et al. "Is Glycemic Control Improving in U.S. Adults?" *Diabetes Care*, 31:1 (Jan. 2008) 81-86.
Albisser, A. M. "The Role(s) of Glucose Sensing in Diabetes: Informative, Archival, or Control?" *Annual International Conference of the IEEE Engineering in Medicine and Biology Society*, 12:2 (1990) 0474-0475.
Nathan, David M. et al. "Medical Management of Hyperglycemia in Type 2 Diabetes: A Consensus Algorithm for the Initiation and Adjustment of Therapy," *Diabetes Care*, 31:12 (Dec. 2008) 1-11.
Albisser, A. Michael "Intelligent Instrumentation in Diabetic Management," *Critical Reviews in BioMedical Engineering*, 17:1 (1989) 1-24.
Miyako, Kenichi et al. "Improved Diabetes Control by Using 'Close Adjustment Algorithms'," *Pediatrics International*, 46 (2004) 678-684.
Lehmann, E. D. "Application of Computers in Clinical Diabetes Care," *Diab Nutr Metab*, 10 (1997) 45-59.
Hirsch, Irl B. et al. "Clinical Application of Emerging Sensor Technologies in Diabetes Management: Consensus Guidelines for Continuous Glucose Monitoring (CGM)," *Diabetes Technology & Therapeutics*, 10:4 (2008) 232-244.
Choe, Hae Mi et al. "Proactive Case Management of High-Risk Patients with Type 2 Diabetes Mellitus by a Clinical Pharmacist: A Randomized Controlled Trial," *Am J Manag Care*, 11:4 (2005) 253-260.
Schrezenmeir, J. et al. "Computer Assisted Insulin Dosage Adjustment—Perspectives for Diabetes Control," 1990.
Spellman, Craig W. "Management of Diabetes in the Real World: Tight Control of Glucose Metabolism," *JAOA*, Supplement 5, 103:8 (Aug. 2003) S8-S13.
Schiffrin, Alicia et al. "Computer-Assisted Insulin Dosage Adjustment," *Diabetes Care*, 8:6 (Nov./Dec. 1985) 545-552.
Albisser, A. M. et al. "Insulin Dosage Adjustment Using Manual Methods and Computer Algorithms: A Comparative Study," *Medical and Biological Engineering & Computing*, 24 (Nov. 1986) 577-584.
Hirsch, Irl B. et al. "A Real-World Approach to Insulin Therapy in Primary Care Practice," *Clinical Diabetes*, 23:2 (2005) 78-86.
Lehmann, E. D. et al. "Compartmental Models for Glycaemic Prediction and Decision-Support in Clinical Diabetes Care: Promise and Reality," *Computer Methods and Programs in BioMedicine*, 56 (1998) 193-204.
Guler, Serdar et al. "Intensification Lessons with Modern Premixes: From Clinical Trial to Clinical Practice," *Diabetes Research and Clinical Practice*, 81S (2008) S23-S30.
Lehmann, E. D. et al. "Insulin Dosage Adjustment in Diabetes," *J Biomed Eng*, 14 (May 1992) 243-249.
Davies, M. et al. "Initiation of Insulin Glargine in Suboptimally Controlled Patients with Type 2 Diabetes: Sub-Analysis of the AT.LANTUS Trial Comparing Treatment Outcomes in Subjects From Primary and Secondary Care in the UK," *Diabetes, Obesity and Metabolism*, 9 (2007) 706-713.
Albisser, A. Michael "Six Generations of the Insulin Dosage Computer: A New Clinical Device for Diabetes Self-Management Through Specialized Centres," *Annual International Conference of the IEEE Engineering in Medicine and Biology Society*, 12:3 (1990) 0996-0997.
Davies, Melanie et al. "Improvement of Glycemic Control in Subjects with Poorly Controlled Type 2 Diabetes," *Diabetes Care*, 28:6 (Jun. 2005) 1282-1288.
Gomis, Ramon et al. "Improving Metabolic Control in Sub-Optimally Controlled Subjects with Type 1 Diabetes: Comparison of Two Treatment Algorithms Using Insulin Glargine," *Diabetes Research and Clinical Practice*, 77 (2007) 84-91.
Saaddine, Jinan B. et al. "Improvements in Diabetes Processes of Care and Intermediate Outcomes: United States, 1988-2002," *Annals of Internal Medicine*, 144 (2006) 465-474.
Van Herpe, Tom et al. "Glycemic Penalty Index for Adequately Assessing and Comparing Different Blood Glucose Control Algorithms," *Critical Care*, 12:1 (R24)(2008) 1-14.
Kennedy, Laurence et al. "Impact of Active Versus Usual Algorithmic Titration of Basal Insulin and Point-of-Care Versus Laboratory Measuremenet of $HbA_{1c}$ on Glycemic Control in Patients with Type 2 Diabetes," *Diabetes Care*, 29:1 (Jan. 2006) 1-8.
Brahams, Diana et al. "Decision Aids and the Law," *The Lancet* (Sep. 9, 1989) 632-634.
Meneghini, L. et al. "The Usage of a Simplified Self-Titration Dosing Guideline (303 Algorithm) for Insulin Detemir in Patients with Type 2 Diabetes—Results of the Randomized, Controlled PREDICTIVE™ 303 Study," *Diabetes, Obesity and Metabolism*, 9 (2007) 902-913.
Stratton, Irene M. et al. "Association of Glycaemia with Macrovascular and Microvascular Complications of Type 2 Diabetes (UKPDS 35): Prospective Observational Study," *BMJ*, 321 (Aug. 12, 2000) 405-412.
Dinsmoor, Robert S. "The Artificial Pancreas: How to 'Close the Loop'," *JDRF Countdown* (Winter 2007) 24-25.
Ford, Earl S. et al. "Trends in A1C Concentrations Among U.S. Adults with Diagnosed Diabetes From 1999 to 2004," *Diabetes Care*, 31:1 (Jan. 2008) 102-104.
Skyler, Jay S. et al. "Algorithms for Adjustment of Insulin Dosage by Patients Who Monitor Blood Glucose," *Diabetes Care*, 4:2 (Mar.-Apr. 1981) 311-318.
Lehmann, E. D. et al. "Application of Computers in Diabetes Care—A Review, I. Computers for Data Collection and Interpretation," *Med Inform*, 20:4 (1995) 281-302.
Lehmann, E. D. et al. "Application of Computers in Diabetes Care—A Review, II. Computers for Decision Support and Education," *Med Inform*, 20:4 (1995) 303-329.
Davies, M. et al. "Initiation of Insulin Glargine Therapy in Type 2 Diabetes Subjects Suboptimally Controlled on Oral Antidiabetic Agents: Results from the AT.LANTUS Trial," *Diabetes, Obesity and Metabolism*, 10 (2008) 387-399.
Meneghini, Luigi et al. "An Electronic Case Manager for Diabetes Control," *Diabetes Care*, 21:4 (Apr. 1998) 591-596.
Buse, John B. et al. "DURAbility of Basal Versus Lispro Mix 75/25 Insulin Efficacy (DURABLE) Trial 24-Week Results," *Diabetes Care*, 32:6 (Jun. 2009) 1007-1013.

(56) References Cited

OTHER PUBLICATIONS

Balas, E. Andrew et al. "Computerized Knowledge Management in Diabetes Care," *Medical Care*, 42:6 (Jun. 2004) 610-621.
Berger, M. et al. "Computer Programs to Assist the Physician in the Analysis of Self-Monitored Blood Glucose Data," Nov. 1988, 52-57.
Raskin, Philip R. et al. "Basal Insulin or Premix Analogue Therapy in Type 2 Diabetes Patients," *European Journal of Internal Medicine*, 18 (2007) 56-62.
Koro, Carol E. et al. "Glycemic Control From 1988 to 2000 Among U.S. Adults Diagnosed with Type 2 Diabetes," *Diabetes Care*, 27:1 (Jan. 2004) 17-20.
Mayfield, Jennifer A. et al. "Insulin Therapy for Type 2 Diabetes: Rescue, Augmentation, and Replacement of Beta-Cell Function," *American Family Physician*, 70:3 (Aug. 1, 2004) 489-500.
Peterson, Charles M. et al. "Randomized Trial of Computer-Assisted Insulin Delivery in Patients with Type I Diabetes Beginning Pump Therapy," *Am J Med*, 81 (Jul. 1986) 69-72.
Queale, William S. et al. "Glycemic Control and Sliding Scale Insulin Use in Medical in patients with Diabetes Mellitus," *Arch Intern Med*, 157 (Mar. 10, 1997) 545-552.
Holman, Rury R. et al. "Addition of Biphasic, Prandial, or Basal Insulin to Oral Therapy in Type 2 Diabetes," *N Engl J Med*, 357:17 (Oct. 25, 2007) 1716-1730.
Woodcock, Alison et al. "Patient Concerns in Their First Year with Type 2 Diabetes: Patient and Practice Nurse Views," *Patient Education and Counseling*, 42 (2001) 257-270.
Hermányi, István et al. "Management of Diabetes with the Use of a Microprocessor: Comparison of Insulin Treatments Based on Blood and Urine Glucose Levels," 1988, 33-40.
Farmer, Andrew J. et al. "A Randomized Controlled Trial of the Effect of Real-Time Telemedicine Support on Glycemic Control in Young Adults with Type 1 Diabetes (ISRCTN 46889446)," *Diabetes Care*, 28:11 (Nov. 2005) 2697-2702.
Schulz, G. et al. "Diabetes Self-Adjustment by a Computerized Program—First Experiences in Inpatient and Outpatient Treatment," 1985, 578-582.
Ambrosiadou, B. V. et al. "Clinical Evaluation of the DIABETES Expert System for Decision Support by Multiple Regimen Insulin Dose Adjustment," *Computer Methods and Programs in BioMedicine*, 49 (1996) 105-115.
Hirsch, Irl B. et al. "Self-Monitoring of Blood Glucose (SMBG) in Insulin- and Non-Insulin-Using Adults with Diabetes: Consensus Recommendations for Improving SMBG Accuracy, Utilization and Research," *Diabetes Technology & Therapeutics*, 10:6 (2008) 419-440.
Nathan, David M. et al. "Management of Hyperglycemia in Type 2 Diabetes: A Consensus Algorithm for the Initiation and Adjustment of Therapy," *Diabetes Care*, 29:8 (Aug. 2006) 1963-1972.
Aubert, Ronald E. et al. "Nurse Case Management to Improve Glycemic Control in Diabetic Patients in a Health Maintenance Organization," 129:8 (Oct. 15, 1998) 605-612.
Lehmann, E. D. et al. "Retrospective Validation of a Physiological Model of Glucose-Insulin Interaction in Type 1 Diabetes Mellitus," *Med Eng Phys*, 16 (May 1994) 193-202.
Albisser, A. Michael "Toward Algorithms in Diabetes Self-Management," *Diabetes Technology & Therapeutics*, 5:3 (2003) 371-373.
Albisser, A. M. et al. "Electronics and the Diabetic," *IEEE Transactions on Biomedical Engineering*, BME-29:4 (Apr. 1982) 239-248.

European Diabetes Policy Group 1998 "Desktop Guide to Type 1 (Insulin-Dependent) Diabetes Mellitus," *Diabetic Medicine*, 16 (1999) 253-266.
European Diabetes Policy Group 1999 "Desktop Guide to Type 2 Diabetes Mellitus," *Diabetic Medicine*, 16 (1999) 716-730.
Action to Control Cardiovascular Risk in Diabetes (ACCORD) Trial—*Protocol*, May 11, 2005, 1-167.
Jenkins, Alicia J. et al. "Evaluation of an Algorithm to Guide Patients with Type 1 Diabetes Treated with Continuous Subcutaneous Insulin Infusion on How to Respond to Real-Time Continuous Glucose Levels," *Diabetes Care*, 33:6 (Jun. 2010) 1242-1248.
Charpentier, Guillaume et al. "The Diabeo Software Enabling Individualized Insulin Dose Adjustments Combined with Telemedicine Support Improves $HbA_{1c}$ in Poorly Controlled Type 1 Diabetic Patients," *Diabetes Care* (online: care.diabetesjournals.org)(Jan. 25, 2011) 1-7.
Mulvaney, Shelagh A. et al. "An Internet-Based Program to Improve Self-Management in Adolescents with Type 1 Diabetes," *Diabetes Care*, 33:3 (Mar. 2010) 602-604.
Strange, Poul "Treat-to-Target Insulin Titration Algorithms When Initiating Long or Intermediate Acting Insulin in Type 2 Diabetes," *Journal of Diabetes Science and Technology*, 1:4 (Jul. 2007) 540-548.
The Juvenile Diabetes Research Foundation Continuous Glucose Monitoring Study Group "Continuous Glucose Monitoring and Intensive Treatment of Type 1 Diabetes," *N Eng J Med*, 359 (2008) 1-13.
Renard, Eric "Clinical Experience with an Implanted Closed-Loop Insulin Delivery System," *Arq Bras Endrocrinol Metab*, 52:2 (2008) 349-354 (with English Abstract).
Oyer, David S. "$A_{1c}$ Control in a Primary Care Setting: Self-Titrating an Insulin Analog Pre-Mix (INITIATEplus Trial)," *Am J Med*, 122:11 (Nov. 2009) 1043-1049.
Stone, Roslyn A. et al. "Active Care Management Supported by Home Telemonitoring in Veterans with Type 2 Diabetes," *Diabetes Care*, 33:3 (Mar. 2010) 478-484.
Quinn, Charlene C. et al. "Cluster-Randomized Trial of a Mobile Phone Personalized Behavioral Intervention for Blood Glucose Control," *Diabetes Care* (online: care.diabetesjournals.org)(Jul. 25, 2011) 1-9.
Bergenstal, Richard M. et al. " Effectiveness of Sensor-Augmented Insulin-Pump Therapy in Type 1 Diabetes," *N Eng J Med*, 363:4 (Jul. 22, 2010) 311-320.
Miller, Shahar et al. "Automatic Learning Algorithm for the MD-Logic Artificial Pancreas System," *Diabetes Technology & Therapeutics*, 13:10 (2011) 1-8.
Kilbride, Lynn et al. "Managing Blood Glucose During and After Exercise in Type 1 Diabetes: Reproducibility of Glucose Response and a Trial of a Structured Algorithm Adjusting Insulin and Carbohydrate Intake," *Journal of Clinical Nursing* (2011) 1-7.
Campos-Cornejo, Fabiola et al. "An Advisory Protocol for Rapid- and Slow-Acting Insulin Therapy Based on a Run-to-Run Methodology," *Diabetes Technology & Therapeutics*, 12:7 (2010) 555-565.
International Search Report for PCT/US2009/039418 dated Nov. 17, 2009.
International Search Report for PCT/US2009/063989 dated May 28, 2010.
International Search Report for PCT/US2010/055246 dated Dec. 13, 2010.
International Search Report for PCT/US2009/039421 dated Nov. 17, 2009.

* cited by examiner

SYSTEMS, METHODS AND DEVICES FOR ACHIEVING GLYCEMIC BALANCE

RELATED DOCUMENTS

The application is a continuation in part of U.S. patent application Ser. No. 12/417,955, filed Apr. 3, 2009, which claims the benefit of priority from, U.S. provisional application Ser. No. 61/042,487, filed 4 Apr. 2008, and U.S. provisional application Ser. No. 61/060,645, filed 11 Jun. 2008. The application is also a continuation in part of U.S. patent application Ser. No. 12/417,960, filed Apr. 3, 2009, which claims the benefit of priority from, U.S. provisional application Ser. No. 61/042,487, filed 4 Apr. 2008, and U.S. provisional application Ser. No. 61/060,645, filed 11 Jun. 2008. The disclosure of each application is incorporated herein by reference in its entirety.

In addition, the present application is related to PCT/US2009/039421, filed Apr. 3, 2009; PCT/US2009/039418, filed Apr. 3, 2009; U.S. patent application Ser. No. 61/113,252, filed Nov. 11, 2008; U.S. patent application Ser. No. 61/257,866, filed Nov. 4, 2009; PCT/US2009/063989, filed Nov. 11, 2009; U.S. patent application Ser. No. 61/257,886 filed Nov. 4, 2009; U.S. patent application Ser. No. 12/926,234, filed Nov. 3, 2010; and PCT/US2010/055246, filed Nov. 3, 2010. Each of these applications is incorporated herein by reference in its entirety. Finally, the reference "Convex Optimization" by Boyd and Vandenberghe (Cambridge University Press, 2004; ISBN-10: 0521833787), is hereby incorporated by reference in its entirety.

FIELD

The present disclosure relates to systems, methods and/or devices for optimizing the insulin dosage regimen for a diabetes patient, and more particularly to such systems, methods and/or devices according to which a processor is programmed at least to determine from the data inputs corresponding to the patient's blood-glucose-level measurements determined at a plurality of times whether and by how much to vary at least one of the one or more components in the patient's present insulin dosage regimen in order to get closer to the patient's desired balance point; wherein the desired balance point, for example, is the patient's lowest blood glucose-level within a predetermined range achievable before increasing the frequency of hypoglycemic events above a predetermined threshold.

BACKGROUND

Diabetes is a chronic disease resulting from deficient insulin secretion by the endocrine pancreas. About 7% of the general population in the Western Hemisphere suffers from diabetes. Of these persons, roughly 90% suffer from Type-2 diabetes while approximately 10% suffer from Type-1. In Type-1 diabetes, patients effectively surrender their endocrine pancreas to autoimmune distraction and so become dependent on daily insulin injections to control blood-glucose-levels. In Type-2 diabetes, on the other hand, the endocrine pancreas gradually fails to satisfy increased insulin demands, thus requiring the patient to compensate with a regime of oral medications or insulin therapy. In the case of either Type-1 or Type-2 diabetes, the failure to properly control glucose levels in the patient may lead to such complications as heart attacks, strokes, blindness, renal failure, and even premature death.

Diabetes is a metabolic disorder where the individual's ability to secrete insulin, and therefore to regulate glucose level has been compromised. For a non-diabetic person, normal glucose levels are typically around 85-110 mg/dl, and can spike after meals to typically around 140-200 mg/dl. Glucose levels can range from hypo- to hyper-glycemia. Low glucose levels or hypoglycemia can drop below life-sustaining level and lead to seizures, consciousness-loss, and even death. Hyperglycemia over a long period of time has been associated with far increased chances to develop diabetes related complications such as heart disease, hypertension, kidney disease, and blindness among others.

Insulin therapy is the mainstay of Type-1 diabetes management and one of the most widespread treatments in Type-2 diabetes, about 27% of the sufferers of which require insulin. Insulin administration is designed to imitate physiological insulin secretion by introducing two classes of insulin into the patient's body: Long-acting insulin, which fulfills basal metabolic needs; and short-acting insulin (also known as fast-acting insulin), which compensates for sharp elevations in blood-glucose-levels following patient meals. Orchestrating the process of dosing these two types of insulin, in whatever form (e.g., separately or as premixed insulin) involves numerous considerations.

First, patients measure their blood-glucose-levels (using some form of a glucose meter) on average about 3 to 4 times per day. The number of such measurements and the variations therebetween complicates the interpretation of these data, making it difficult to extrapolate trends therefrom that may be employed to better maintain the disease. Second, the complexity of human physiology continuously imposes changes in insulin needs for which frequent insulin dosage regimen adjustments are warranted. Presently, these considerations are handled by a patient's endocrinologist or other healthcare professional during clinic appointments. Unfortunately, these visits are relatively infrequent—occurring once every 3 to 6 months—and of short duration, so that the physician or other healthcare professional is typically only able to review the very latest patient medical data. In consequence, it has been shown that more than 60% of patients control their diabetes at sub-optimal levels, leading to unwanted complications from the disease.

Indeed, one of the major obstacles of diabetes management is the lack of availability of a patient's healthcare professional and the relative infrequency of clinic appointments. Studies have, in fact, established that more frequent insulin dosage regimen adjustments, for example, every 1 to 2 weeks—improves diabetes control in most patients. Yet as the number of diabetes sufferers continues to expand, it is expected that the possibility of more frequent insulin dosage regimen adjustments via increased clinic visits will, in fact, decrease. And, unfortunately, conventional diabetes treatment solutions do not address this obstacle.

The device most commonly employed in diabetes management is the glucose meter. Such devices come in a variety of forms, although most are characterized by their ability to provide patients near instantaneous readings of their blood-glucose-levels. This additional information can be used to better identify dynamic trends in blood-glucose-levels. However, conventional glucose meters are designed to be diagnostic tools rather than therapeutic ones. Therefore, by themselves, even state-of-the-art glucose meters do not lead to improved glycemic control.

One conventional solution to the treatment of diabetes is the insulin pump. Insulin pumps are devices that continuously infuse short acting insulin into a patient at a predetermined rate to cover both basal needs and meals. As with manual insulin administration therapy, a healthcare professional sets the pump with the patient's insulin dosage regimen during clinic visits. In addition to their considerable current expense, which prohibits their widespread use by patients with Type-2 diabetes, insulin pumps require frequent adjustment by the physician or other healthcare professional to compensate for the needs of individual patients based upon frequent blood-glucose-level measurements.

An even more recent solution to diabetes treatment seeks to combine an insulin pump and near-continuous glucose monitoring in an effort to create, in effect, an artificial pancreas regulating a patient's blood-glucose-level with infusions of short-acting insulin. According to this solution, real-time patient information is employed to match insulin dosing to the patient's dynamic insulin needs irrespective of any underlying physician-prescribed treatment plan. While such systems address present dosing requirements, they are entirely reactive and not instantaneously effective. In consequence of these drawbacks, such combined systems are not always effective at controlling blood glucose levels. For instance, such combined units cannot forecast unplanned activities, such as exercise, that may excessively lower a patient's blood-glucose level. And when the hypoglycemic condition is detected, the delay in the effectiveness of the insulin occasioned not only by the nature of conventional synthetic insulin but also the sub-dermal delivery of that insulin by conventional pumps results in inefficient correction of the hypoglycemic event.

The most common biomarker used to access glycemic control is hemoglobin A1C (A1C for brevity). The relationship between average glucose levels and A1C has been studied. For healthy individuals A1C is between 4.6% and 5.8%, for people with diabetes the American Diabetes Association (ADA) and the European Association for the Study of Diabetes (EASD) recommend maintaining A1C<7% that correlates to an average glucose level below 150 mg/dl.

Studies have demonstrated the relationship between A1C and complication. The ADA and EASD have set the goal of getting A1C to below 7%. This was chosen as a compromise between lowering the risk for developing complications and the risk of severe (and potentially fatal) hypoglycemia. As a result, diabetes management has developed with its main goal being to bring A1C down as reflected by several consensus statements issued by various authorities. Up until recently, little attention has been devoted to the other side of the equation being prevention of hypoglycemia. It is assumed that hypoglycemia is a side effect of insulin, or oral anti-diabetes drugs (OAD), therapy as when mean glucose decreases one's chances of seeing more low glucose levels increases. Since lowering A1C and avoiding hypoglycemia may be considered as inversely related the standard of care is that clinical studies aim at reducing A1C while reporting the observed rate of hypoglycemia as the unavoidable evil that is part of the therapy.

While the foregoing solutions are beneficial in the management and treatment of diabetes in some patients, or at least hold the promise of being so, there continues to exist the need for methods, devices and/or systems that would cost-effectively improve diabetes control in patients wherein a goal of diabetes management may be achieving glycemic balance and/or improved glycemic composite index weighing both A1C and the risk for or frequency of hypoglycemia. And the other needs and advantages addressed herein.

SUMMARY

Certain embodiments are directed to systems, devices and/or methods for treating a patient's diabetes by providing treatment guidance. For example, a method for treating a patient's diabetes by providing treatment guidance, the method comprising: storing one or more components of the patient's insulin dosage regimen; obtaining data corresponding to the patient's blood glucose-level measurements determined at a plurality of times; tagging each of the blood glucose-level measurements with an identifier reflective of when or why the reading was obtained; and determining the patient's current glycemic state relative to a desired balance point; and determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before increasing the frequency of hypoglycemic events above a predetermined threshold.

Certain embodiments are directed to systems, devices and/or methods for updating a patient's insulin dosage regimen. For example, the method comprising: storing one or more components of the patient's insulin dosage regime; obtaining data corresponding to the patient's blood glucose-level measurements determined at a plurality of times; incrementing a timer based on at least one of the passage of a predetermined amount of time and the receipt of each blood glucose-level measurement; tagging each of the blood glucose-level measurements with an identifier reflective of when the reading was obtained; determining for each of the obtained blood glucose-level measurements whether the measurement reflects a hypoglycemic event or a severe hypoglycemic event; and varying at least one of the one or more components in the patient's insulin dosage regime in response to a determination that the most recent blood glucose-level measurement represents a severe hypoglycemic event.

Certain embodiments are direct to apparatus for treating a patient's diabetes by providing treatment guidance. For example, an apparatus comprising: a processor; and a computer readable medium coupled to the processor; wherein the combination of the processor and the computer readable medium are configured to: store one or more components of the patient's insulin dosage regimen; obtain data corresponding to the patient's blood glucose-level measurements determined at a plurality of times; tag each of the blood glucose-level measurements with an identifier reflective of when or why the reading was obtained; determine the patient's current glycemic state relative to a desired balance point; and determine from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before increasing the frequency of hypoglycemic events above a predetermined threshold.

Certain embodiments are direct to apparatus for updating a patient's insulin dosage regimen. For example, an apparatus comprising: a processor; and a computer readable medium coupled to the processor; wherein the combination of the processor and the computer readable medium are configured to: store one or more components of the patient's insulin dosage regime; obtain data corresponding to the patient's blood glucose-level measurements determined at a plurality of times; increment a timer based on at least one of the passage of a predetermined amount of time and the receipt of each blood glucose-level measurement; tag each of the blood glucose-level measurements with an identifier reflective of when the reading was obtained; determine for each of the obtained blood glucose-level measurements whether the measurement reflects a hypoglycemic event or a severe hypoglycemic event; vary at least one of the one or more components in the patient's insulin dosage regime in response to a determination that the most recent blood glucose-level measurement represents a severe hypoglycemic event.

Certain embodiments are direct to apparatus for improving the health of a diabetic population. For example, an apparatus comprising: a processor and a computer readable medium coupled to the processor and collectively capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before the frequency of hypoglycemic events exceeds a predetermined threshold.

Certain embodiments are directed to systems, methods and or devices for improving the health of a diabetic population. For example, a method comprising: treating a least one diabetic patient in the population using a device capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before the frequency of hypoglycemic events exceeds a predetermined threshold.

Certain embodiments are directed to systems, methods and or devices for improving the health of a diabetic population. For example, a method comprising: identifying at least one diabetic patient; treating the a least one diabetic patient to control the patient's blood glucose level; wherein the patient's blood glucose level is controlled using a device capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before the frequency of hypoglycemic events exceeds a predetermined threshold.

Certain embodiments of the methods, devices and/or systems disclosed herein are useful to achieve reduction in the frequency of hypoglycemia by changing the distribution of insulin between different administration points rather than reducing the daily total insulin dosage. Certain embodiments are directed to methods, systems and/or devices for treating a patient's diabetes by providing treatment guidance wherein the frequency of hypoglycemic events is reduced without significantly reducing the total amount of insulin used by the patient.

In certain embodiments, the system comprises at least a first memory for storing data inputs corresponding at least to one or more components of a patient's present insulin dosage regimen, and data inputs corresponding at least to the patient's blood-glucose-level measurements determined at a plurality of times; and a processor operatively connected to the at least first memory. The processor is programmed at least to determine from the data inputs corresponding to the patient's blood-glucose-level measurements determined at a plurality of times whether and by how much to vary at least one of the one or more components in the patient's present insulin dosage regimen.

In certain embodiments, the at least first memory and the processor are resident in a single apparatus. Per one feature, the single apparatus further comprises a glucose meter. The glucose meter may be separate from the single apparatus, further to which the glucose meter is adapted to communicate to the at least first memory of the single apparatus the data inputs corresponding at least to the patient's blood-glucose-level measurements determined at a plurality of times.

Per one feature thereof, the single apparatus may further comprises data entry means for entering data inputs corresponding at least to the patient's blood-glucose-level measurements determined at a plurality of times directly into the at least first memory. In certain aspects, the single apparatus may further comprises a way to enter data inputs corresponding at least to the patient's blood-glucose-level measurements determined at a plurality of times directly into the at least first memory.

There may, per other aspects of the disclosure, further be provided data entry means disposed at a location remote from the single apparatus for remotely entering data inputs corresponding at least to the one or more components in the patient's present insulin dosage regimen into the at least first memory. In certain aspects, the data entry may be disposed at a location remote from the single apparatus for remotely entering data inputs corresponding at least to the one or more components in the patient's present insulin dosage regimen into the at least first memory.

Certain embodiments may comprise at least a first data entry means disposed at a location remote from the at least first memory and processor for remotely entering data inputs corresponding at least to the one or more components in the patient's present insulin dosage regimen into the at least first memory, and at least second data entry means, disposed at a location remote from the at least first memory, processor and at least first data entry means, for remotely entering data inputs corresponding at least to the patient's blood-glucose-level measurements determined at a plurality of times into the at least first memory.

Certain embodiments may comprise a way to enter a first data set disposed at a location remote from the at least first memory and processor for remotely entering data inputs corresponding at least to the one or more components in the patient's present insulin dosage regimen into the at least first memory, and a way to enter a second data set, disposed at a location remote from the at least first memory, processor and the first data set corresponding at least to the patient's blood-glucose-level measurements determined at a plurality of times that is entered into the at least first memory.

In certain aspects, the data inputs corresponding at least to the patient's blood-glucose-level measurements determined at a plurality of times are each associated with an identifier indicative of when the measurement was input into the memory. Optionally, there may be provided data entry means enabling a user to define the identifier associated with each blood-glucose-level measurement data-input, to confirm the correctness of the identifier associated with each blood-glucose-level measurement data-input, and/or to modify the identifier associated with each blood-glucose-level measurement data-input. Optionally, there may be provided a way to enter data enabling a user to define the identifier associated with each blood-glucose-level measurement data-input, to confirm the correctness of the identifier associated with each blood-glucose-level measurement data-input, and/or to modify the identifier associated with each blood-glucose-level measurement data-input.

According to other embodiments, the processor is programmed to determine on a predefined schedule whether and by how much to vary at least one of the one or more components in the patient's present insulin dosage regimen.

In certain aspects, the processor is programmed to determine whether each data input corresponding to the patients blood-glucose-level measurements represents a severe hypoglycemic event, and to vary at least one of the one or more components in the patient's present insulin dosage regimen in response to a determination that a data input corresponding to the patient's blood-glucose-level measurements represents a severe hypoglycemic event.

According to certain embodiments, the processor is programmed to determine from the data inputs corresponding to the patient's blood-glucose-level measurements determined at a plurality of times if there have been an excessive number of hypoglycemic events over a predefined period of time, and to vary at least one of the one or more components in the patient's present insulin dosage regimen in response to a determination that there have been an excessive number of such hypoglycemic events over a predefined period of time.

In certain aspects, the processor is programmed to determine from the data inputs corresponding at least to the patient's blood-glucose-level measurements determined at a plurality of times if the patient's blood-glucose level measurements fall within or outside of a predefined range, and to vary at least one of the one or more components in the patient's present insulin dosage regimen only if the patients blood-glucose level measurements fall outside of the predefined range. The processor may be further programmed to determine from the data inputs corresponding at least to the patients blood-glucose-level measurements determined at a plurality of times whether the patient's blood-glucose-level measurements determined at a plurality of times represent a normal or abnormal distribution. In certain aspects, this determination comprises determining whether the third moment of the distribution of the patients blood-glucose-level measurements determined at a plurality of times fall within a predefined range.

In certain embodiments, where the one or more components in the patient's present insulin dosage regimen comprise a long-acting insulin dosage component, the processor is programmed to determine from the identifier indicative of when a measurement was input into the memory at least whether the measurement is a morning or bed-time blood-glucose-level measurement, to determine whether the patient's morning and bed-time blood-glucose-level measurements fall within a predefined range, and to determine by how much to vary the patient's long-acting insulin dosage component only when the patient's morning and bed-time blood-glucose-level measurements are determined to fall outside of the said predefined range. In connection therewith, the processor may further be programmed to factor in an insulin sensitivity correction factor that defines both the percentage by which any of the one or more components of the insulin dosage regimen may be varied and the direction in which any fractional variations in any of the one or more components are rounded to the nearest whole number. Optionally, the at least first memory further stores data inputs corresponding to a patient's present weight, and the insulin sensitivity correction factor is in part determined from the patient's present weight. Per certain aspects, the determination of by how much to vary the long-acting insulin dosage component of a patient's present insulin dosage regimen may be a function of the present long-acting insulin dosage, the insulin sensitivity correction factor, and the patient's blood-glucose-level measurements.

In certain embodiments, the one or more components in the patient's present insulin dosage regimen comprise a short-acting insulin dosage component defined by a carbohydrate ratio and plasma glucose correction factor, and the processor is programmed to determine whether and by how much to vary the patient's carbohydrate ratio and plasma glucose correction factor. In connection with this determination, the processor may be programmed to factor in an insulin sensitivity correction factor that defines both the percentage by which any one or more components of the insulin dosage regimen may be varied and the direction in which any fractional variations in the one or more components are rounded to the nearest whole number.

In certain embodiments, the determination of by how much to vary the present plasma glucose correction factor component of a patient's insulin dosage regimen may be a function of a predefined value divided by the mean of the total daily dosage of insulin administered to the patient, the patient's present plasma glucose correction factor, and the insulin sensitivity correction factor. Alternatively, a value representing twice the patient's daily dosage of long-acting insulin in the present insulin dosage regimen may be substituted for the mean of the total daily dosage of insulin administered to the patient as an approximation thereof. Per still another feature hereof, the plasma glucose correction factor component of the patient's insulin dosage regimen may be quantized to predefined steps of mg/dL.

According to certain embodiments, the determination of by how much to vary the present carbohydrate ratio component of a patient's insulin dosage regimen is a function of a predefined value divided by the mean of the total daily dosage of insulin administered to the patient, the patient's present carbohydrate ratio, and the insulin sensitivity correction factor. Alternatively, a value representing twice the patient's daily dosage of long-acting insulin in the present insulin dosage regimen is substituted for the mean of the total daily dosage of insulin administered to the patient as an approximation thereof. Further hereto, the processor may also be programmed to determine a correction factor that allows variations to the carbohydrate ratio component of a patient's insulin dosage regimen to be altered in order to compensate for a patient's individual response to insulin at different times of the day.

A further feature of certain embodiments is that the one or more components in the patient's present insulin dosage regimen comprise a long-acting insulin dosage component, and the determination of by how much to vary the long-acting insulin dosage component is constrained to an amount of variation within predefined limits.

In certain embodiments the one or more components in the patient's present insulin dosage regimen comprise a short-acting insulin dosage component defined by a carbohydrate ratio and plasma glucose correction factor, and the determination of by how much to vary any one or more of each component in the short-acting insulin dosage is constrained to an amount of variation within predefined limits.

According to certain embodiments, the one or more components in the patient's present insulin dosage regimen comprise a short-acting insulin dosage component taken according to a sliding scale, and the processor is programmed to determine whether and by how much to vary at least one of the components of the sliding scale. The determination of by how much to vary the sliding scale may further be constrained to an amount of variation within predefined limits.

According to certain embodiments, the one or more components in the patient's present insulin dosage regimen comprise a short-acting insulin dosage component where meal bolus components, whether a carbohydrate to insulin ratio or a fixed dose with a sliding scale, may differ from one meal to the other, and the processor is programmed to determine whether and by how much to vary at least one of the components independent of the other components. The determination of by how much to vary a dosage component may further be constrained to an amount of variation within predefined limits.

According to certain embodiments, insulin dosage may comprise of a single component representing a daily total of long acting insulin the user has to administer. Such daily total may be administer as a single injection or split between more than one injection, and the processor is programmed to determine whether and by how much to vary the daily total insulin units of the long acting insulin component.

According to certain embodiments, insulin dosage may comprise of a two component representing a two separate insulin doses to be taken with specific events. Such example may be a breakfast dose and a dinner dose of premixed or biphasic insulin, and the processor is programmed to determine whether and by how much to vary at least one of the two different dosage component.

In certain embodiments, the processor is programmed to calculate glycemic index indicative of the user metabolic state associated with a particular event. In certain embodiments, glycemic index is a single number comprised of the average, median, minimum, maximum, or other metrics of the data set being measured, and the processor is programmed to determine whether and by how much to vary at least one of the one or more insulin dosage components based at least on glycemic index.

Certain embodiments are methods for determining the amount of insulin needed by a diabetic comprising the steps of: A. taking a plurality of historical blood glucose readings from a patient; B. taking a plurality of historical readings of insulin administered to a patient; C. determining a protocol for providing insulin to a patient based upon the plurality of historical readings and a patient's blood glucose reading at a fixed time; and D. providing insulin to the patient based upon the protocol, historical readings of Steps A and B and the patient's blood glucose reading of Step C. In certain aspects, the protocol is reevaluated over a fixed time interval. In certain aspects, the fixed time interval is, for example, weekly or every two weeks. In certain aspects, the protocol is reevaluated based on predefined events (e.g., a blood glucose reading indicating a hypo-glycemic event) in an asynchronous manner. In certain embodiments, the plurality of historical readings of insulin administered to a patient includes the number of units and the type of insulin for each time insulin is administered to a patient.

Certain embodiments are to systems to determine the amount of insulin needed by a diabetic patient comprising: A. means to input blood glucose readings of a patient; B. means to determine a protocol based upon the blood glucose readings; and C. means to modify the protocol over a period of time based upon historical blood glucose readings. In certain aspects, the system is provided within a glucose meter. In certain aspects, the system further comprises means to input quantities of insulin administered by a patient. In certain aspects, the system further comprises an infusion pump to administer insulin to the patient based upon the protocol and the blood glucose readings.

Certain embodiments are systems to determine the amount of insulin needed by a diabetic patient comprising: A. a way to input blood glucose readings of a patient; B. a way to determine a protocol based upon the blood glucose readings; and C. a way to modify the protocol over a period of time based upon historical blood glucose readings. In certain aspects, the system is provided within a glucose meter. In certain aspects, the system further comprises a way to input quantities of insulin administered by a patient. In certain aspects, the system further comprises an infusion pump to administer insulin to the patient based upon the protocol and the blood glucose readings.

BRIEF DESCRIPTION OF THE DRAWINGS

The accompanying drawings and figures facilitate an understanding of the various embodiments of this technology.

DETAILED DESCRIPTION

Figure 1:
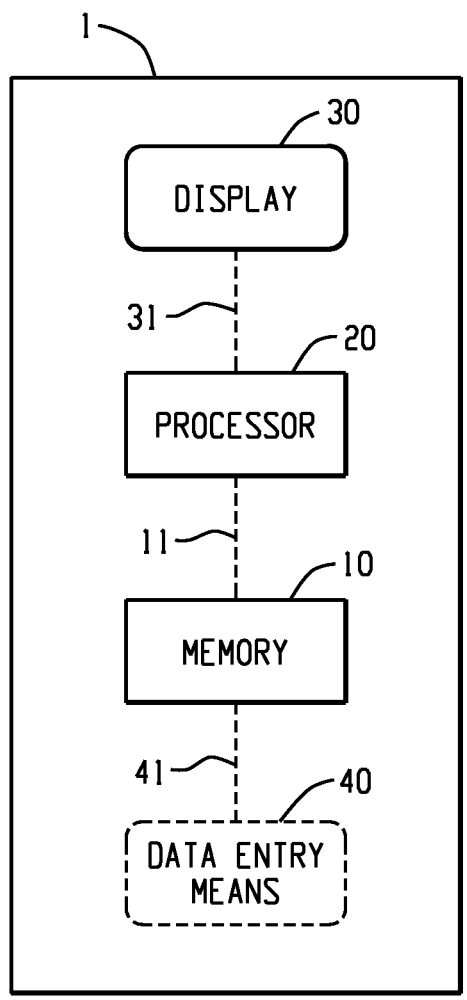
FIG. 1 is a simplified schematic of an apparatus according to certain exemplary embodiments.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The subject headings used in the detailed description are included only for the ease of reference of the reader and should not be used to limit the subject matter found throughout the disclosure or the claims. The subject headings should not be used in construing the scope of the claims or the claim limitations.

The term "insulin dosage function" or "IDF" as used herein with respect to certain embodiments refers to a lookup table indicative of an insulin regimen, a protocol, or a combination thereof that a user follows. For example, for a patient following premixed insulin regimen the insulin dosage function may contain two numbers associated with two events reflective of two insulin injection per day, say X insulin units with breakfast and Y insulin units with dinner. The term IDF history as used herein with respect to certain embodiments refers to chronology of insulin dosage functions and external insulin dosage functions viewed as one data set. The first IDF in an IDF history is the active insulin dosage function or the lookup table currently use to recommend the user an appropriate insulin dose per a particular event and event related information. The next record is the second IDF in IDF history the following is the third IDF in IDF history and so forth through the existing records in IDF history The term "partial update" as used herein with respect to certain embodiments refers to the operation of updating a single dosage component in an insulin dosage function. In certain embodiments, a partial update may change more than one dosage components. In certain embodiments, a partial update may not interfere with the synchronous dosage adjustment frequency. In certain embodiments, an event that caused a partial updated may be excluded when the time to perform a synchronous adjustment is due.

The term "full update" as used herein with respect to certain embodiments refers to the operation of assessing insulin dosage components to determine if and by how much to change one or more of the dosage components. In certain embodiments, the operation of a full update results in a reset of the synchronous clock. In certain embodiments, the operation of a full update may result in data expiring from the period under evaluation. For example, certain embodiments may employ a counter to determine the number of hypoglycemic events that occurred within a given interval, the process of a full update may cause a reset of that counter.

The terms "severe hypoglycemic event" or "SHE" as used herein with respect to certain embodiments refers to blood glucose value below a certain threshold. In certain embodiments, a severe hypoglycemic event is a patient history event with glucose data less than 55 mg/dl. In certain embodiments, a severe hypoglycemic event is a patient history event with glucose data less than 40, 45, 50, 55, 60, 65, 70 mg/dl or combinations thereof.

Certain embodiments are directed to a therapeutic device which is a glucose meter equipped with artificial intelligence (AI) and capable of optimizing medication dosage of patients treated with various types of insulin, including optimizing combination of insulin types, i.e., both short and long acting insulin. Certain embodiments monitor patient glucose reading and additional parameters and modify insulin dosage as needed in a similar manner to what an endocrinologist, or other qualified health care provider, would do if that person had continuous access to patient's data. By dynamically modifying medication dosage based on individual lifestyle and changing needs an optimal dosage level is reached. In turn, this leads to superior glycemic control and better patient prognosis.

Glycemic Balance

A goal of diabetes management may be achieving glycemic balance and/or improved glycemic composite index weighing both A1C and hypoglycemia. Another goal of diabetes management may be moving a patient towards glycemic balance and/or improved glycemic composite index weighing at least A1C and hypoglycemia. There are several potential ways of minimizing a combination of two parameters sometime referred to as minimizing a cost function of two arguments. The definition of the cost function is significant by itself as its shape may determine what type of solution for the minimization problem exists. Convex cost function can be minimized by several methods and the minimal solution is unique. Optimization of convex function is well studied and books like "Convex Optimization" by Boyd and Vandenberghe (Cambridge University Press, 2004; ISBN-10: 0521833787) and others describes several known methods to perform such optimization. Unfortunately, widely acceptable definitions of what is "an acceptable level of hypoglycemia" do not exist. However, certain aspects of the present disclosure are aimed at setting the goal of achieving a better glycemic balance or an improved glycemic composite index (GCI) by minimizing one argument while making an effort to keep the other argument under a certain threshold. Certain aspects of the present disclosure are aimed at setting the goal of guiding a subject to a glycemic balance or an improved glycemic composite index (GCI) by minimizing one argument while making an effort to keep the other argument under a certain threshold. For example, one possible approach is to minimize glycemic index (GI) as long as it is above a certain threshold while keeping the frequency of hypoglycemia below another threshold; wherein GI is a measure of a set reducing a plurality of historic blood glucose level to a single variable. For example GI can be the mean or median of a given set of glucose values. Other metrics can also be combined like the minimum, maximum, minimum of the mean or median, and other combinations like pattern recognition capable of reducing a multidimensional data set to a single value. In certain embodiments, it may be desired to increase one or more of the insulin dosage component in order to reduce glycemic index assuming glycemic index is above 120 mg/dl and provided that there have been no more than 3 low blood glucose values during the period under observation. Other numbers are also contemplated like increasing one or more of the insulin dosage components if glycemic index is above 150, 140, 130, 110, 100, 90, or 80 mg/dl and provided that there were no more than 1, 2, 4, 5, 6, 7, 8, 9, or 10 low blood glucose values during the period under observation. In certain embodiments low blood glucose values may be define as glucose level below 80, 75, 70, 65, 60, 55, 50, or 45 mg/dl. Other methods as disclosed herein may also be chosen.

In certain embodiments, as typically done in constrained optimization a dual approach is to reduce the frequency of hypoglycemia as long as glycemic index is below a certain threshold. For example, in certain embodiments, it may be desired to reduce on or more of the insulin dosage components, if the frequency of hypoglycemia is more than 3 during the observed interval and provided that glycemic index is less than 200 mg/dl. Other values like 1, 2, 4, 5, 6, 7, or 8 hypoglycemic episodes may be combined with glycemic a index less than 250, 240, 230, 220, 210, 190, 180, 170, 160, 150, 140, 130, 120 can also be used.

For example, to improve GCI certain embodiments may chose to reduce mean glucose as long as the rate of hypoglycemia does not exceed a certain threshold. If insulin is used to reduce mean glucose then increased insulin dosage may result in decreased glucose level. The reduction in glucose may, in some cases, lead to hypoglycemia. If the rate of hypoglycemia exceeds a predefined threshold then insulin dosage may be decreased. Decreased insulin dosage may lead to increased average glucose, which in turn reduces the chances of experiencing hypoglycemia. An exemplary algorithm that achieve that can be described as follows:

```
count the number of hypoglycemic episodes over a given
  time to determine hypoglycemia rate (HR)
    if HR > N
      reduce insulin level
    otherwise
      calculate glycemic index (GI)
      if GI < A₁
        decrease insulin dosage
      if GI > A₂
        increase insulin dosage.
```

The unacceptable hypoglycemic rate threshold (N) may be set to 80 events/year, although other numbers such as 50, 60, 70, 75, 85, 90, 100, 110 or 120 events/year may also be used. The two other thresholds $A_1$ and $A_2$ may be selected to drive GI to a desired target. For example one can set a lower level of 80 mg/dl and a higher level of 130 mg/dl, although other combinations of numbers may also be used. For example, glucose values of 60, 65, 70, 75, 85, 90, 95, 100, 105 or 110 mg/dl can be used as the lower threshold $A_1$, and glucose values of 110, 115, 120, 125, 135, 140, 145, 150, 155 or 160 mg/dl can be used as the upper threshold $A_2$.

The glycemic index (GI) is various statistics that may be derived from available glucose data. For example, statistics that may be used are mean, median, min, max, other mathematical operator that can be extract from a particular set of glucose data (e.g. pattern detection), or combinations thereof.

Hypoglycemic Events

To correctly account for hypoglycemic events for the purpose of insulin adjustment it is useful that such events would be appropriately tagged. In general, a non-fasting glucose level is reflective of the previous insulin injection. For example, a lunch glucose reading is reflective of the effect that the breakfast insulin bolus may had on the user blood glucose levels. In some cases, as a non-limiting example, when a user feels symptoms of hypoglycemia, they may measure glucose outside of their regular schedule. Such glucose data point is typically marked as 'Other'. If the 'Other' glucose level is low it is useful to identify the insulin injection that most likely caused the low 'Other' blood glucose level so that the appropriate insulin dosage component would be reduced accordingly. The process of reclassifying an 'Other' event relies on the timestamp of the 'Other' event and the time that past from a previous event that was not classified as 'Other', for example a meal event. The pharmacokinetic profile of the particular insulin used by the user can help set a time window during which an injection may had a particular effect that resulted in a low blood glucose level. In one example, the user may be administering fast-acting insulin which may be active 30 minutes post injection and its effect will completely wear off within 6 hours post injection. For this example, if a 'Lunch' event is recorded at 12 PM and a low blood glucose level is recorded as 'Other' at 12:10 PM it is unlikely that this low blood glucose level is a result of the Lunch fast-acting insulin injection because it happened too quickly and fast-acting insulin takes longer to start affecting blood glucose levels. Similarly, if an 'Other' event is recorded after 6 PM it is unlikely the cause of the lunch fast-acting injection since its effect has already worn off the user. Therefore, it is understood that for a fast acting insulin, with a pharmacokinetic activity profile of 30 minutes to 6 hours from an injection, low blood glucose levels, tagged as 'Other', that occurs within 30 minutes to 6 hours from an injection event are likely a result of that injection. Accordingly, it may be desired to reduce the dosage component that most likely caused that low blood glucose level.

Other types of insulin may also be considered. Some rapid-acting or ultra rapid-acting insulin may have a pharmacokinetic activity profile where they start affecting blood glucose levels within 15 minutes from administration and their effect wears off within 3 hours. Older types of insulin, like Regular Insulin (e.g. by Elly Lilly), may take 45 minutes to start affecting blood glucose levels and as many as 8 hours to wear off. If a user administers pre-mixed or biphasic insulin then the pharmacokinetic profile of such drugs, e.g. Humulin 70/30, Novolin 70/30, Humalog Mix 75/25, or Novolog Mix 70/30, may be affecting blood glucose levels starting about 1 hour after injection and ending around 12 hours post injection. It is also appreciated that long-acting insulin's, such as Lantus® or Levemir®, have a fairly flat pharmacokinetic profile and their activity level is nearly constant over a 24 hours period. Therefore, if a user is administering a combination of long acting and fast acting insulin for their diabetes management glucose levels tagged as 'Other' that falls outside of a particular time window following a fast-acting insulin administration are most likely attributed to the background long-acting insulin injection. Accordingly, if an 'Other' event recorded a low glucose level and appeared 7 hours post the last meal event recorded in history, that glucose level can be used to reduce the long-acting insulin dosage component.

In certain embodiments, it may be desired to reduce an insulin dosage component as soon as a very low blood glucose (VLG) level has been logged into history. A VLG level may be define as blood glucose level below 60 mg/dl, although other numbers, such as below 70, 65, 55, 50, 45, 40 or 35 mg/dl as well as other numbers in similar ranges can also be used. Once a VLG has been logged it is desired that the dosage component that has most likely caused that VLG will be reduced. That dosage component can be proportionally reduced by 10%, 20%, 30%, 40% or 50%, or reduced by a fixed number of insulin units such as reduced by 1, 2, 3, 4, 6, 8, 10, or other reasonable numbers in that range. The reduction of dosage may also be a combination of the two, for example dosage component will be reduced by the greater of (X units or Y %). In this case, if a user is administering 10 insulin units say X=2 and Y=10% than the greater of 2 [insulin units] or 10% of 10 [insulin units] is 2 [insulin units], in which case the new dosage component will be 8 insulin units, instead of the previous component that was 10. In other cases the combination may be the smaller of (X units or Y %). If the latter was applied to the previous example than the smaller of the two is 1 insulin units and the new recommended dosage component would be 9 insulin units, instead of the previous component that was 10. Another alternative to a dosage component reduction is a 'roll back', that is find the previous dosage component that is lower than the current one and replace the current component with the previous one. For example, if an insulin dosage component was 10 units and was later increased to 13 units. And, a while later the dosage component of 13 is suspected as the reason behind a VLG it may be desired to replace the component 13 with the previous lower value of 10. This is done regardless of proportionality or a fixed minimal/maximal reduction because according to the data in the device history the previous value of 10 did not cause any VLG.

In some cases it would be appreciated that glucose values may be low but not very low. A range for low glucose LG can be defined as values that are not VLG, contemplated before, yet lower than a particular value like 75 mg/dl. Other numbers can also be used for the upper threshold like, 90, 85, 80, 70, 65, 60, 55, 50, 45 or 40 mg/dl or other reasonable numbers in that range. In some embodiments, it may be desired to account for a plurality of LG values even if independently none of them accounts as a VLG to updated insulin dosage components. This is particularly useful if a similar event is suspicious as causing the LG values. For example if a dosage was installed on Monday evening and Tuesday lunch LG value is recorded and Wednesday lunch LG value is recorded it may be desired to reduce the breakfast dosage component. Another example can be that 3 LG values have been recorded for different events within a 24 hours period. Yet another example can be that 4 LG values have been recorded for different events from the time last dosage was instated. Other combinations, like 3 or more LG values for a particular event, 2 LG values or more within a 24 hours period, or 2, 3, 4, 5, 6, 7, 8, 9, 10 LG values recorded from the time stamp when current dosage was installed, are also contemplated.

It is appreciated that low blood glucose value are typically an indication the user is administering too much insulin for its current metabolic state. This condition may lead to VLG or to a severe hypoglycemic event that is potentially life threatening. It is therefore desired that a system adjusting insulin dosage is capable of reducing one or more of the user's insulin dosage components in an attempt to prevent the situation from having a negative clinical outcomes. The aforementioned behavior of a system that adjusts insulin dosage on a synchronous basis, e.g., once a week, can be summarized as follows: if one or more VLG values have been logged by the system an effort is made to identify a dosage component that may have caused that one or more VLG values and reduced it according to dosage reduction rules. This response to an occurrence of one or more VLG values may or may not reset the synchronous time base for the insulin adjustment process. If one or more LG values have been logged by the system there is an attempt to assess the cause of the one or more LG values and to respond accordingly by reducing one or more of the insulin dosage components. Such a reduction may or may not lead to a reset of the synchronous clock.

When adjusting insulin dosage it may be desirable to prevent oscillations, i.e., low blood glucose levels leading to a dosage reduction leading to higher blood glucose levels leading to a dosage increase leading to lower blood glucose levels and so forth. Several mechanisms can be used to dampen, reduce or substantially decrease, unstable dosage oscillations. One such mechanism would be inserting 'off intervals' between different directions of dosage adjustments. For example a system may follow a rule that if a dosage was reduced from baseline then the next dosage adjustment step can be further reduction or keep in place but not an increase. This way a dosage increase will typically never follow a dosage decrease reducing the likelihood of blood glucose levels oscillations. Another mechanism can be that if a dosage reduction occurred and an increase is recommended in the following dosage adjustment step, then such increase should typically be limited. The increase can be limited to be less than a particular level, for example, less than the value that was used before the reduction occurred, or no greater than the level that was used before the reduction occurred, or not to exceed that level that was used before the reduction occurred by more than 5%, 10%, 15% or 20%, or 2 insulin units or 4 insulin units, or other similar expression. This way it is understood that the insulin dosage adjustment system is using short term memory by not only reviewing the blood glucose data accumulated in history during the period under review but also utilizing the dosage history that preceded the period under review.

It would be appreciated that a similar mechanism can be used for the other direction, i.e., a dosage decrease that followed a prior increase. Such decrease may also be limited, dampened, reduced, to prevent, or substantially prevent unstable oscillations. However, it is understood that insulin dosage reduction is typically done to improve the safety of the therapy and prevent future hypoglycemia.

In some embodiments it is desired to prevent consecutive dosage increments as the user response to such increments may be delayed. A delayed response to insulin dosage increments may result in severe hypoglycemia or other adverse events. In some embodiments the contemplated system may use a consecutive dosage increment rule to establish an 'off period' if an excessive number of consecutive dosage increments occurred. For example, a system may employ a rule that prevents 2 consecutive increments from occurring, i.e., creating an 'off period' after each dosage increment allowing for a delayed response. Other rules may also apply, for example, allowing for two consecutive increments in dosage but not 3, or allowing for 3 consecutive dosage increments but not 4, or allowing for 4 consecutive increments but not five.

In certain embodiments, there are several ways one can use to assess as to whether the new dosage represents an increment compared to the previous dosage. Some examples are give below in table 1. This can be simple for basal only insulin regimen where the user has to administer $Z_1$ insulin units per day. Then, if the new dosage components $Z_2$ is greater than $Z_1$ the dosage has been increased. However, for more complex regimens such as premixed/biphasic insulin therapy or basal bolus insulin therapy alternative definitions can be used to define what constitutes a dosage increase. For example, for a premixed/biphasic insulin regimen each dosage component is simply the dose one needs to administer for a given event. That is, a premixed insulin dosage may include a dose of $X_1$ units of insulin at breakfast and a dose of $Y_1$ units at dinner. If the new dosage includes $X_2$ and $Y_2$ then several methods can be used to determine an increment, e.g., the methods shown in Table 1 below:

TABLE 1

$X_2 + Y_2 > X_1 + Y_1$
$X_2 > X_1$ and $+ Y_2 \geq Y_1$
$Y_2 > Y_1$ and $+ X_2 \geq X_1$
$X_2 > X_1$ and $+ Y_2 < Y_1$ but $X_2 + Y_2 > X_1 + Y_1$
$Y_2 > Y_1$ and $+ X_2 < X_1$ but $X_2 + Y_2 > X_1 + Y_1$
either $X_2 > X_1$ or $Y_2 > Y_1$ Regardless of the definition used, it may be desirable to prevent successive insulin dosage increments. In some embodiments, a projected daily total such as the sum of the dosage components may be used to determine whether the current insulin dosage represents an increase compared to prior week. In regimens that require carbohydrate counting, the projected daily total would require estimating average meal size as the dosage component are ratios and cannot be simply added to determine daily total. Meal size estimates can relies on recorded carbohydrate intake logged in the system over a predefined period of time, for example, the last week, the last couple of weeks, or the last month. An estimated meal content can be calculated for different meals or as a daily total recorded carbohydrate intake.

In some embodiments, historic data stored in the system memory may be incomplete. In certain embodiments, incomplete data may be defined as less than 3 data points for a particular events. In other embodiments, incomplete data may be defined as less than 5, 4, 2, or 1 data points per event. In some instances, the user may chose to only measure fasting blood glucose. This has a varying level of meaning depending on the insulin regimen used by the user. If a user is following a basal only regimen than fasting blood glucose level may be sufficient to safely and effectively adjust insulin dosage to achieve a better glycemic balance. However, for a person using premixed insulin therapy, that administers insulin twice a day, a single test per day may not suffice to appropriately adjust insulin. In certain embodiments, the instance when a particular data set, e.g. events of type 'Breakfast', is in complete is referred to as a missing data set.

In certain embodiments, if a single data set is missing the system may decide to keep insulin dosage unchanged for the particular period under observation. If more than one data set is missing, e.g., breakfast and lunch data sets, it may be decided to keep insulin dosage unchanged. In other embodiments, the presence of a missing data set may be a reason to limit the allowed change for other dosage components. For example, for a user taking premixed insulin twice daily at breakfast and dinner it may be decided that if breakfast data is missing than the breakfast dosage component, that is adjusted using dinner data set, cannot be increased to a level that is more than twice the dinner dosage component. Other limits are also contemplated. For example the breakfast dosage component cannot be increased to more than 150% of the dinner component.

In certain embodiments used with basal-bolus insulin therapy, the presence of a missing data set may be used to limit the ratio between fast acting and long acting insulin. For example, in the case of a missing data set it may be desired to keep the long acting insulin dosage component no more than 70% of the total daily amount of insulin injected. In the case of a missing data set it may be desired to keep the total fast insulin dosage components no more than 70% of the total daily amount of insulin injected. In other embodiments, it may be desired to limit the increase allowed for a single fast acting insulin dosage component. For example, if lunch data set is missing than the dinner dosage component can only be increased if the dinner dosage component is no more than 40% of the total fast acting insulin dosage. Similar examples that relates to the other dosage components are also contemplated. For example, if dinner data is missing than the breakfast dosage component can only be increased if it is no more than 40% of the total fast acting insulin.

Balance Point

Clinical data may suggest that the optimal balance point is different for different people with diabetes. For example, in some studies it was noted that a small portion of the study population (about 10% of subjects) experienced about 90% of the severe hypoglycemic episodes. It is very likely that some people with diabetes are more prone to hypoglycemia. For such individuals the optimal glycemic balance may mean A1C>7%, since A1C of 7% or less will place them at a too greater risk.

Figure 13:
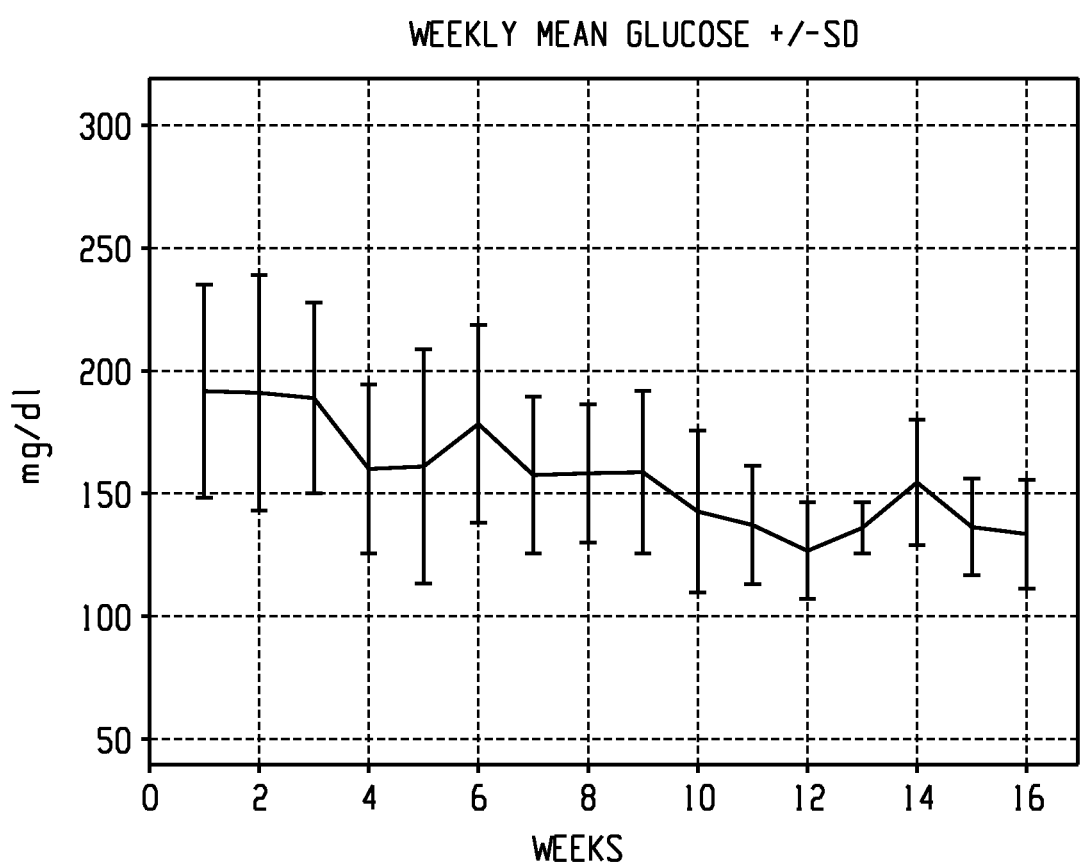
FIG. 13 illustrates a subject with low variability of glucose levels.
Figure 14:
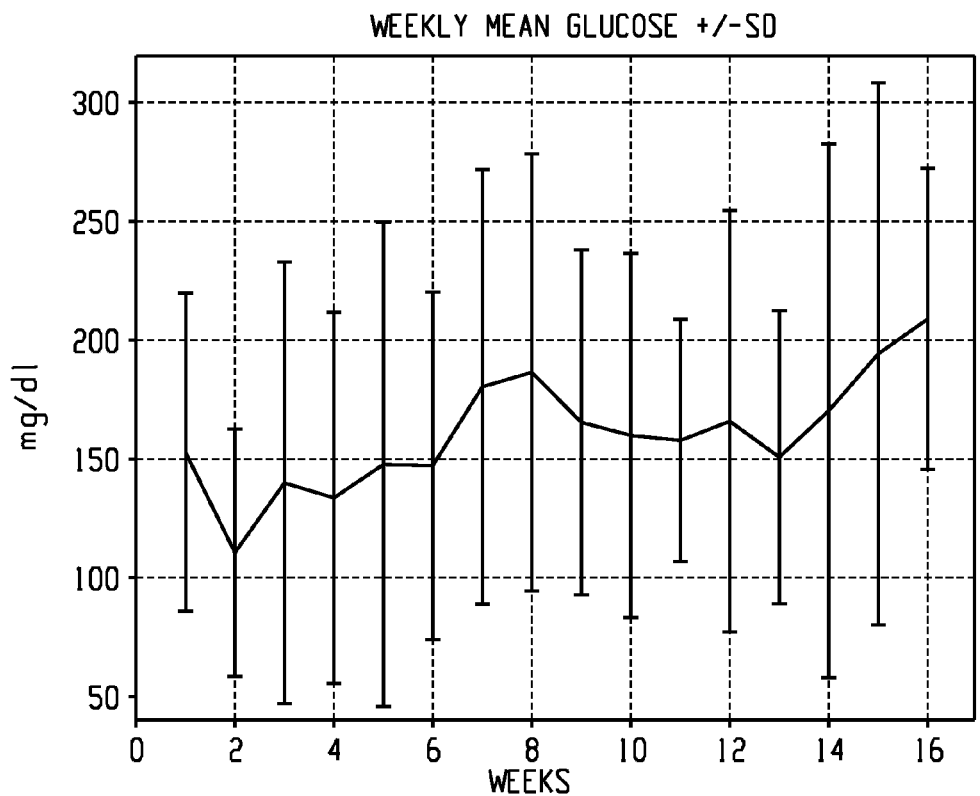
FIG. 14 illustrates a subject with high variability of glucose level.
Figure 15:
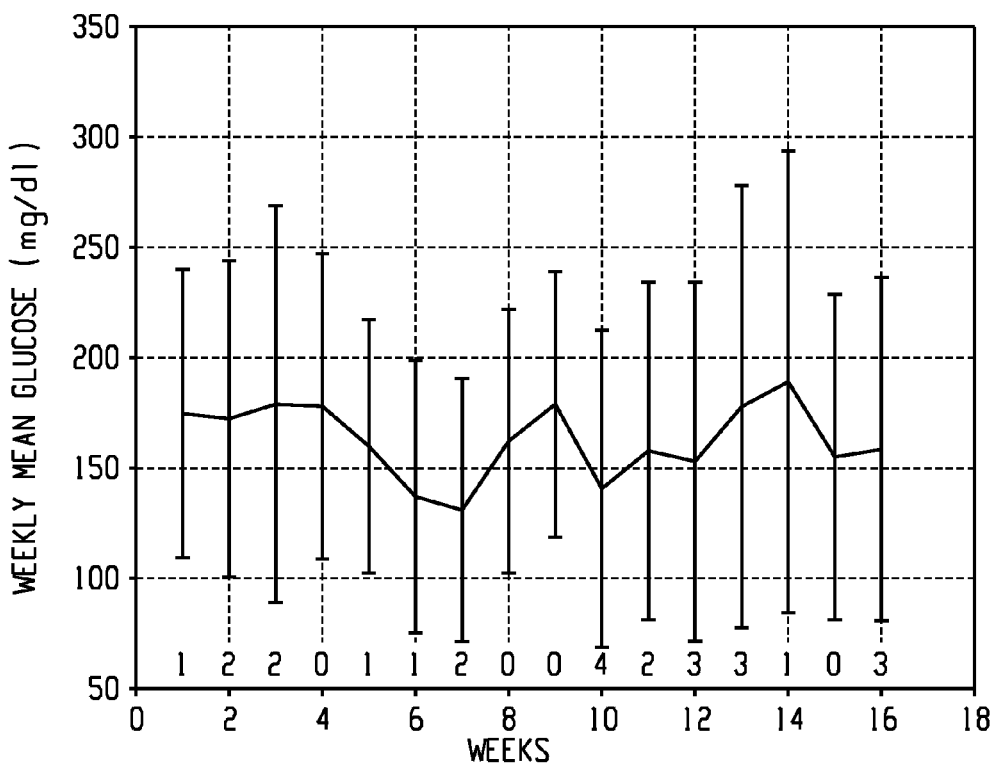
FIG. 15 illustrates a patient with varying level of glycemic variability.

The optimal glycemic balance for each individual may vary overtime and that there may be no 'steady state'. That is, the optimal GCI for each individual may need to be constantly evaluated. One reason for this may be that GCI may be affected by the variability of an individual glucose data. For some that variability is low as illustrated in FIG. 13. FIG. 13 illustrates a patient with low variability of glucose levels. Each point of the figure represents weekly mean glucose data and the vertical bars are plus or minus one standard deviation. In others the variability may be high as illustrated in FIG. 14. FIG. 14 illustrates a patient with high variability of glucose level. Each point of the figure represents weekly mean glucose data and the vertical bars are plus or minus one standard deviation. In others the variability may be inconsistent as illustrated in FIG. 15. FIG. 15 illustrates a patient with varying level of glycemic variability. Each point of the figure represents weekly mean glucose data and the vertical bars are plus or minus one standard deviation. In weeks 10-16 there are far more glucose values<65 mg/dl (the numbers beneath each bar) as compared to weeks 1-9 despite the fact that mean glucose is roughly stable and in fact slightly higher during the second period.

Overall, in certain embodiments applying a mass policy of optimizing GCI may be much safer than applying a policy aimed at reducing A1C. Neglecting to set therapy goals that accounts for hypoglycemia may lead to severe consequences and even death. However, by applying a policy of optimizing glycemic balanced or GCI, as illustrated in certain embodiments, one can be reassured that therapy will be intensify only as long as it does not lead to too many hypoglycemic episodes.

There is little consensus as to what constitute minor hypoglycemia. It is generally accepted that severe hypoglycemia is one that requires the assistant of a third party to be resolved. It is also accepted that minor hypoglycemia may be the best predictor for severe hypoglycemia. However, while some define minor hypoglycemia as capillary glucose levels below 70 mg/dl numbers such as 65, 50, and even 40 mg/dl can also be found.

Figure 16:
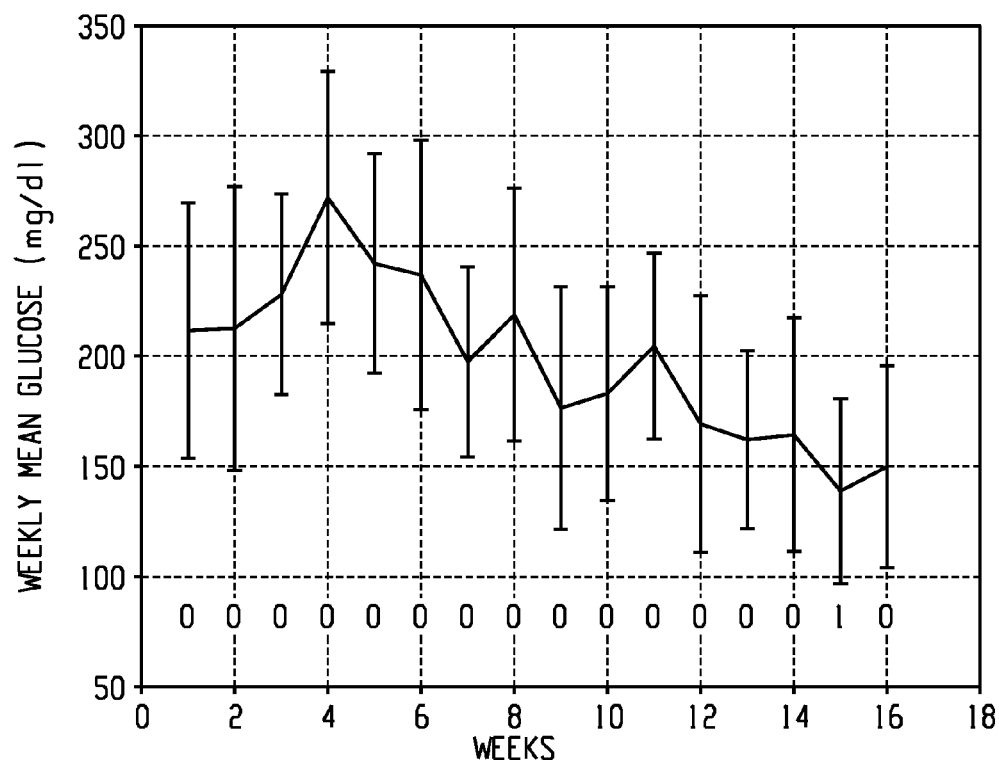
FIG. 16 illustrates a subject with a high glucose level and low variability.
Figure 17:
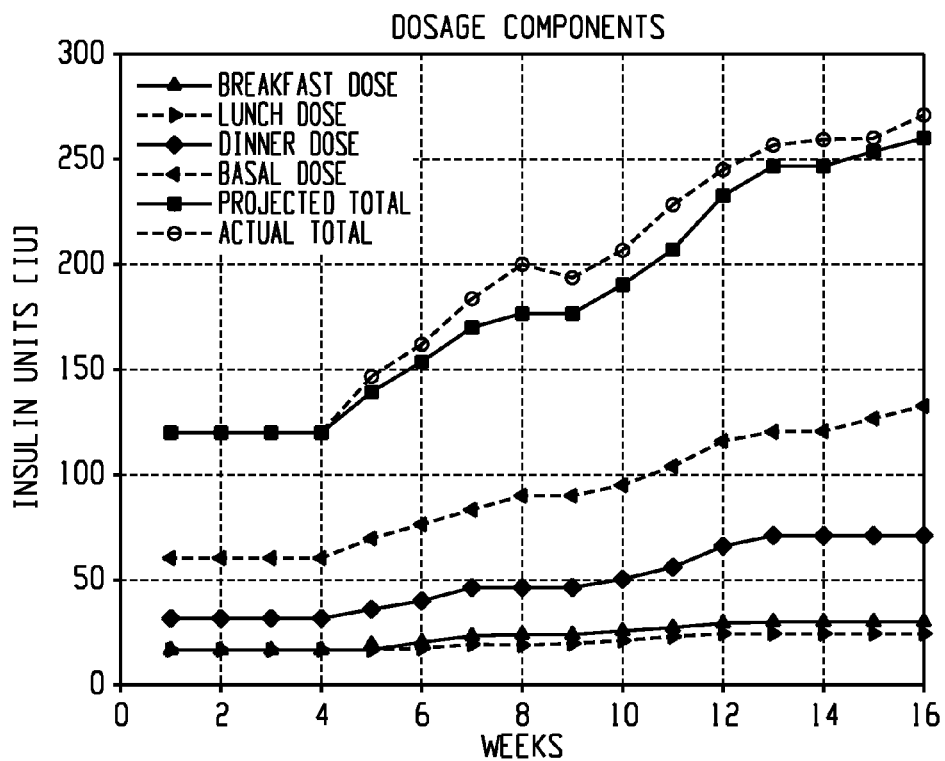
FIG. 17 illustrated insulin dosage of a subject with a high glucose level and low variability.

For example, a subject with a high glucose level and low variability is illustrated in FIGS. 16 and 17. In this example, the subject requires more insulin. There are no hypoglycemic episodes and his A1C is 8.5% at week 4 and 6.1% at week 16. FIG. 16 shows that throughout the 16 weeks period the patient had just one glucose level<65 mg/dl (week 15). FIG. 17 shows that the total daily insulin more than double over 12 weeks (120 to 270 [IU]). More specifically, dinner and basal insulin more than doubled (from 30→71 and 60→133, respectively), while breakfast and lunch almost doubled (15 to 29 and 27, respectively). This particular subject can safely maintain A1C level of 6.1%, well below the recommended goal of 7%.

Figure 18:
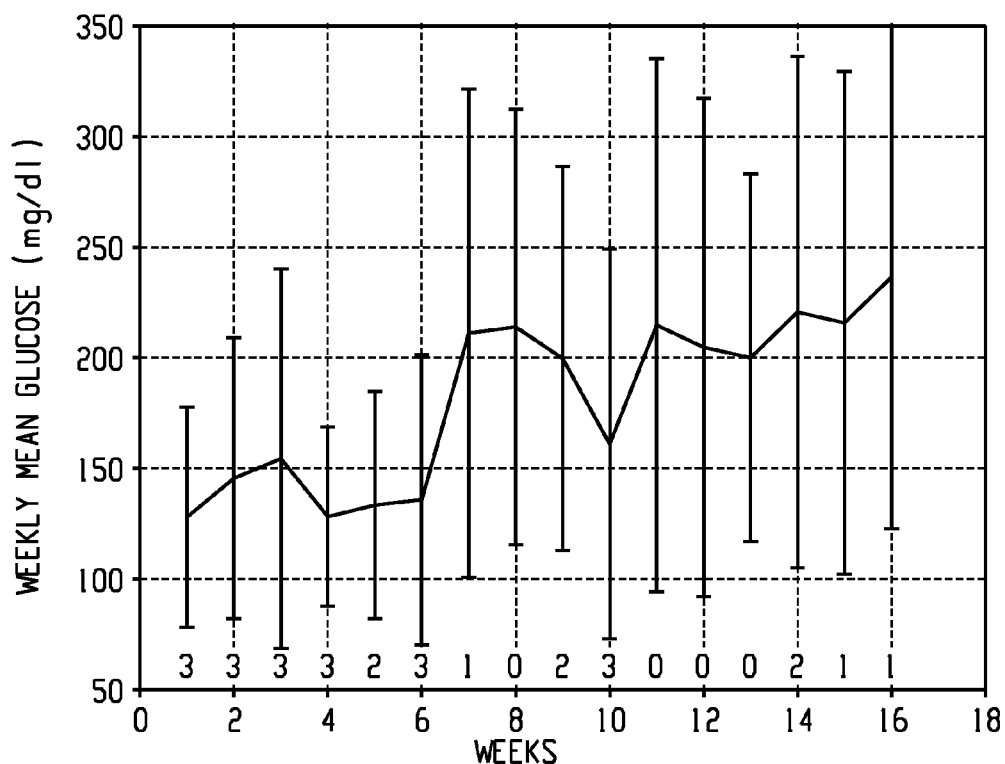
FIG. 18 illustrates a subject with low glucose with high variability.
Figure 19:
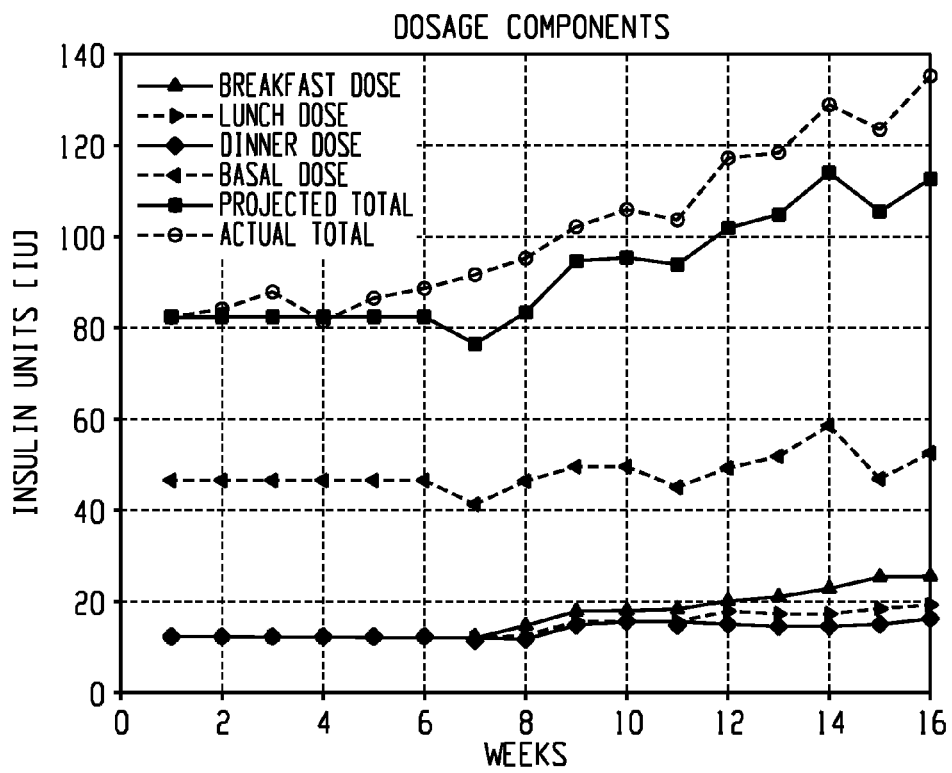
FIG. 19 illustrates insulin dosage of a subject with low glucose with high variability.

Another example of a subject with low glucose with high variability is illustrated in FIGS. 18 and 19. The subject had a baseline A1C of 8.5% yet during weeks 1 through 4, the ran-in period, the subject's mean glucose is below 150 mg/dl with 3 hypoglycemic episodes/week and week 4 A1C is 7.2%. For this subject it is unsafe to keep A1C that low. Hence, improved glycemic composite index translates to higher mean glucose with less hypoglycemia. The subject had week 16 A1C of 7.7% but hypoglycemia rate decreased 3 folds. FIG. 18 illustrates that during the first 4 weeks (ran-in period) subject has 3 hypoglycemic episodes per week (a rate of 156 episodes/year). During the last 4 weeks the subject had 4 hypoglycemic episodes, a rate of 52/yr. FIG. 19 illustrates that that insulin did not decrease but rather increased throughout the intervention period. Initially (weeks 5-6) it remains steady, then the patient experienced a shift in its metabolic state to higher mean glucose. Therefore, insulin dosage slowly increases from ~80 units a day to nearly 140 units a day. During week 10, 3 hypoglycemic episodes caused a temporal reduction of dosage.

Figure 20:
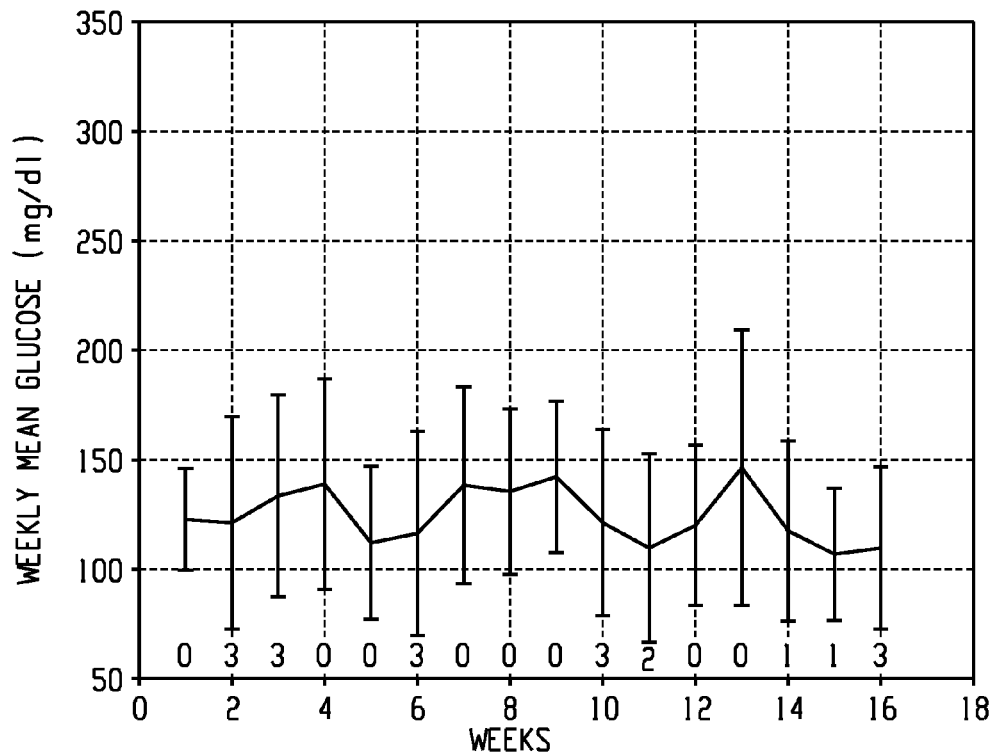
FIG. 20 illustrates a subject with low glucose with low variability.
Figure 21:
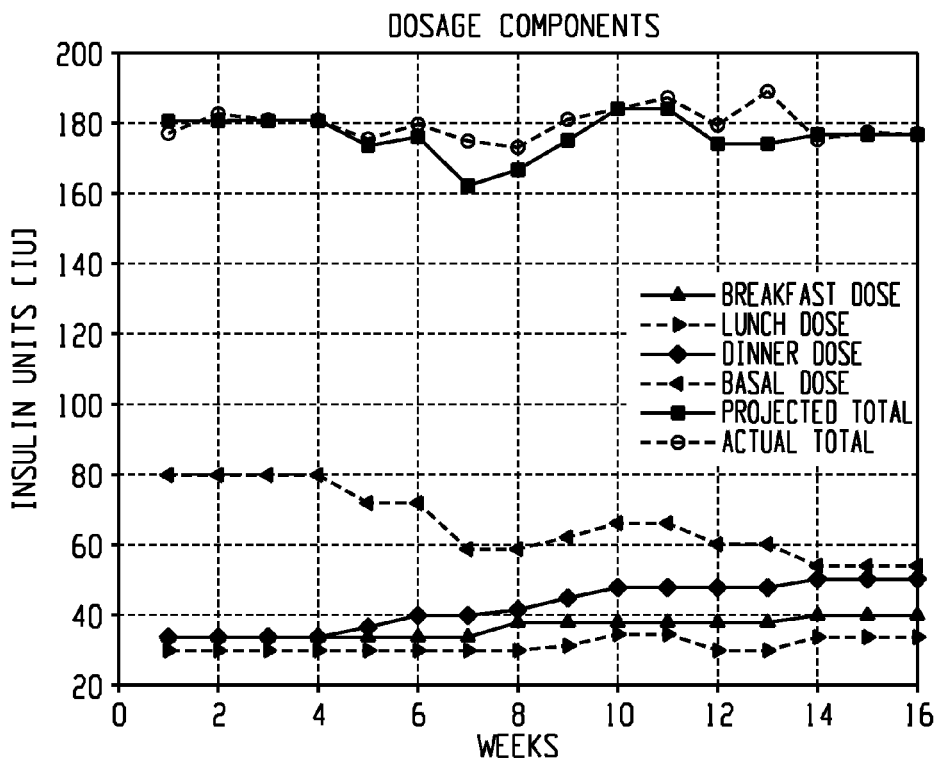
FIG. 21 illustrates insulin dosage of a subject with low glucose with low variability.

Another example of a subject with low glucose with low variability is illustrated in FIGS. 20 and 21. Here the subject had week 4 A1C of 7.7%, mean glucose is below 150 mg/dl, yet there are 6 episodes of hypoglycemia during the run-in period. FIG. 20 illustrates that the subject had low glycemic variability but also low mean glucose. Therefore, optimizing GCI is a delicate task balancing near normal glucose levels while keeping the rate of hypoglycemia at bay. Throughout the 12 weeks of intervention mean glucose is maintained near normal while annual rate of hypoglycemia decreases form 78 to 56. FIG. 21 shows that for this subject the total daily insulin remains fairly stable at ~180 units, yet its distribution is shifted from being 45%/55% basal to bolus in week 4 to being 30%/70% basal to bolus in week 16.

Figure 22:
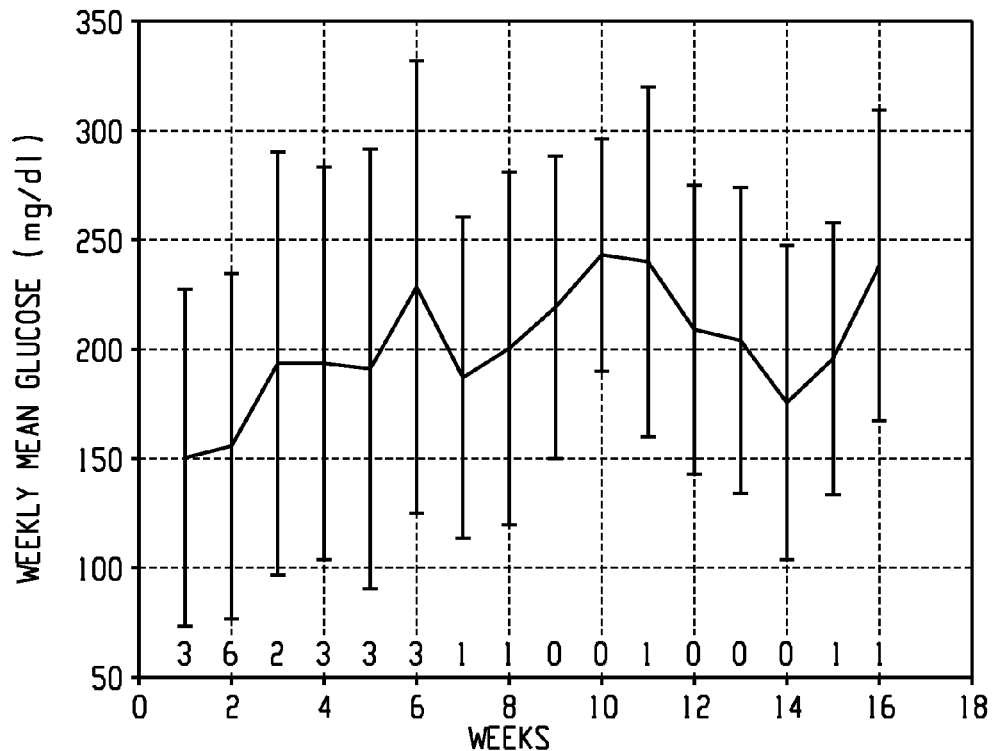
FIG. 22 illustrates a subject with high glucose with high variability.
Figure 23:
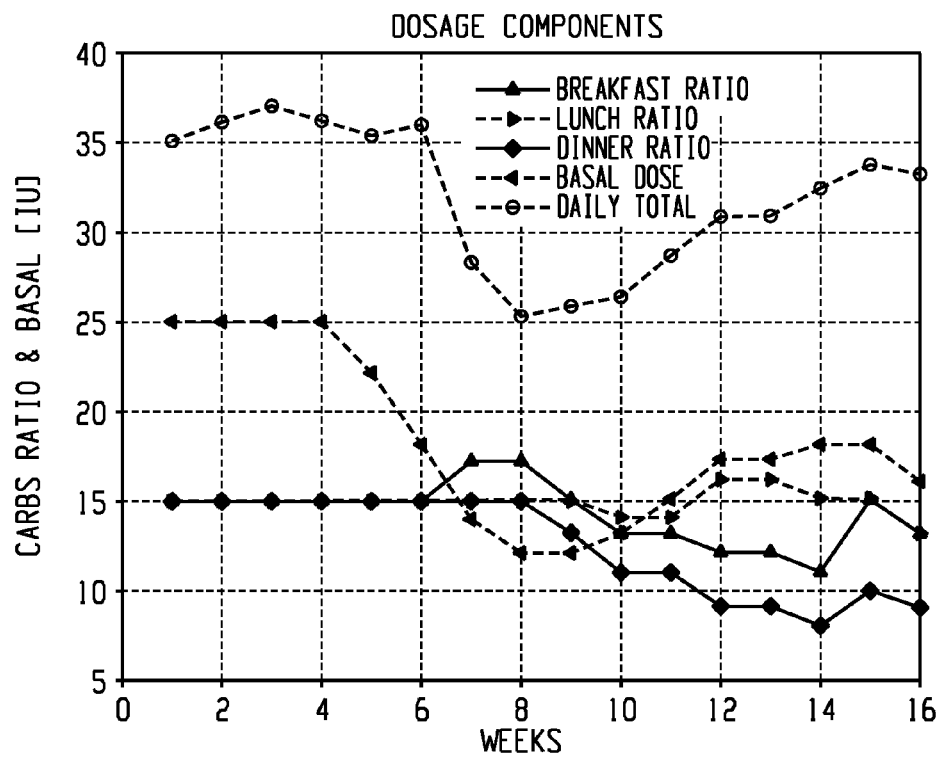
FIG. 23 illustrates insulin dosage of a subject with high glucose with high variability.

Another example of a subject with high glucose with high variability is illustrated in FIGS. 22 and 23. Subject has week 4 A1C of 8.2%, mean glucose ~180 mg/dl, yet 14 episodes of hypoglycemia (a rate of 182/year). Subject requires significant reduction in insulin before it can be increased again slowly. During last 3 weeks of the study the subject is taking almost the same amount of insulin as during the run in period yet with minimal hypoglycemia. FIG. 22 illustrates a subject with high glucose, high glycemic variability, and high rate of hypoglycemia during the run in period. For this subject hypoglycemia rate decreased from 182/yr to 48/yr, while A1C increased from 8.2% (week 4) to 9.7% (week 16). FIG. 23 as opposed to the previous 3 examples, illustrates that this subject counts carbs to figure out his bolus doses. Hence, meal dosage is given as ratio. For example, dinner dosage starts at a ratio of 1 insulin unit to every 15 grams of carbohydrates and end at a ratio of 1 [IU]:9 [gr. carbs]. To reduce hypoglycemia basal dose is reduced from 25 [IU] to 12 [IU] (weeks 4 to 8). Thereafter, without hypoglycemia insulin dosage is slowly increased. Eventually, the subject is taking at the end of the study almost the same amount of insulin as in the beginning yet with a far different distribution.

Figure 24:
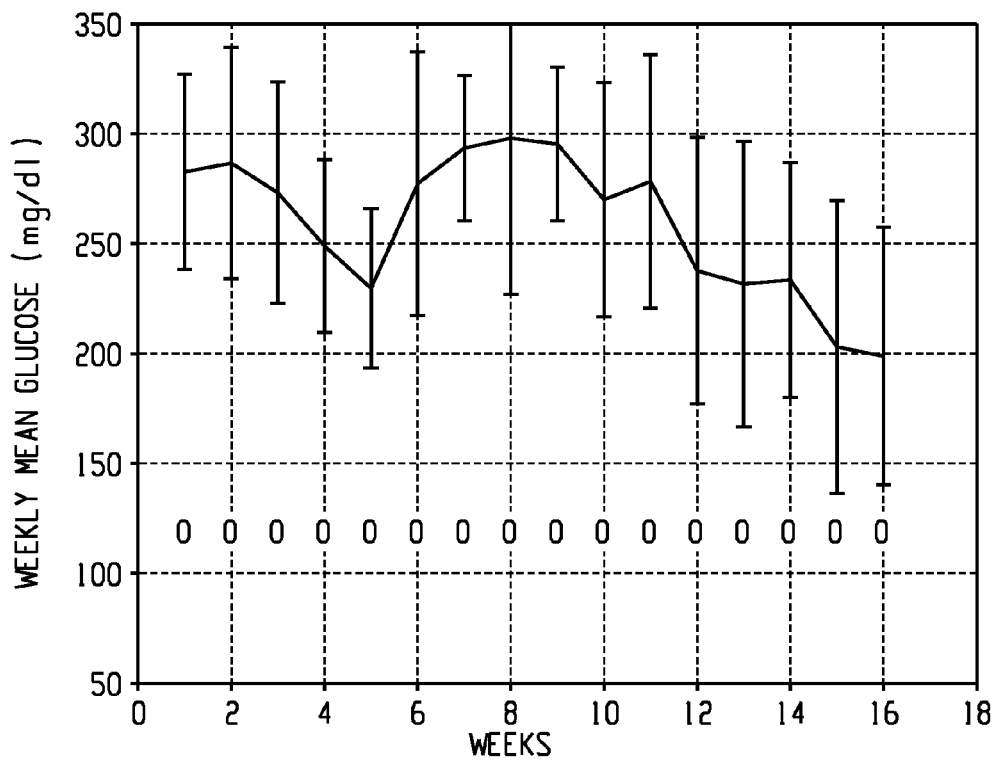
FIG. 24 illustrates blood glucose levels of a subject on a premixed insulin therapy.
Figure 25:
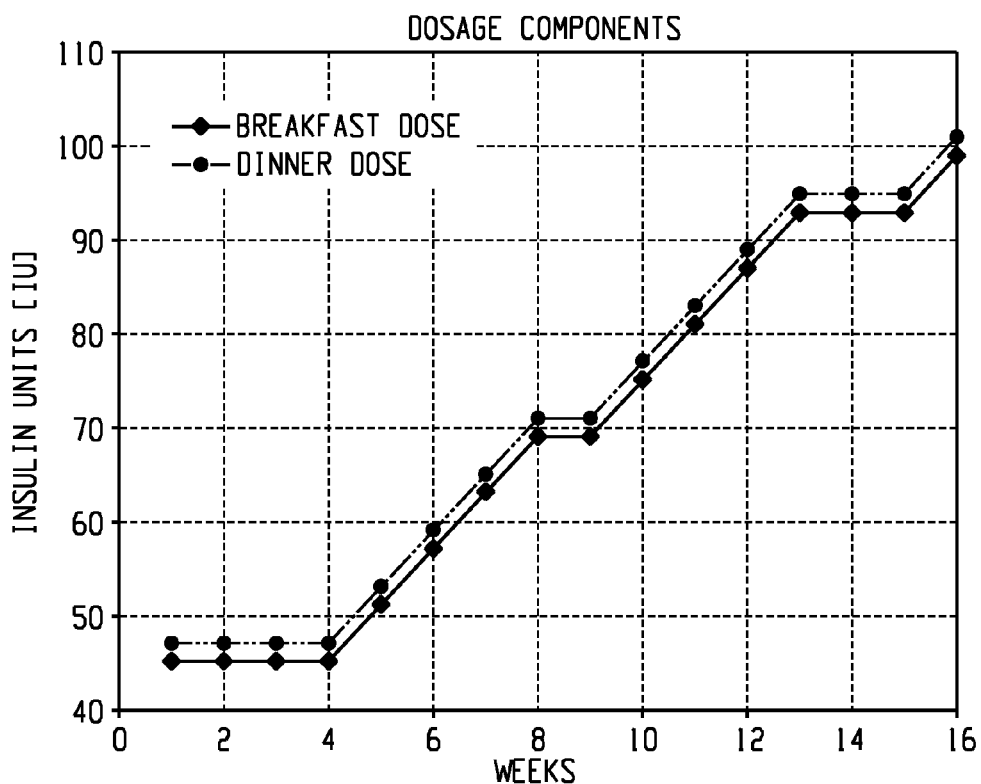
FIG. 25 illustrates insulin dosage of a subject on premixed insulin therapy.

In another example of a patient on premixed insulin therapy. FIG. 24 shows a reduction in weekly mean glucose from weeks 1-4 'for no apparent reason' as insulin dosage remained unchanged during that time. FIG. 24 also shows that the increase in insulin dosage in weeks 5-8 (from a daily total of 92 units to 140 units) resulted in a significant increase in mean glucose (from ~230 mg/dl to ~300 mg/dl). Furthermore, in weeks 12-14 mean glucose roughly equals that of week 5 although insulin dosage is ~190 units a day (more than twice that of week 5). This patient had A1C of 13.2% in week 0, 11.3% in week 4, and 9.1% in week 16. FIG. 25 illustrates the fact that certain disclosed embodiments did not increase dosage for more than 4 consecutive weeks. Note that there is no dosage increase in weeks 9 and 13 despite elevated glucose levels.

Figure 26:
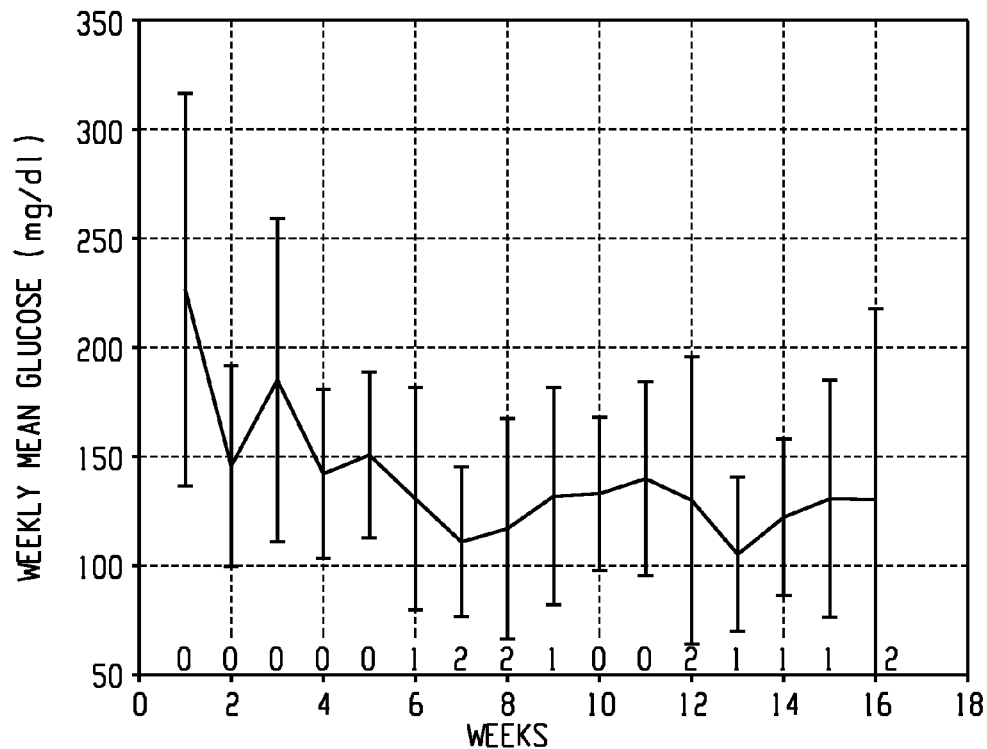
FIG. 26 illustrates blood glucose levels of a subject on a premixed insulin therapy.
Figure 27:
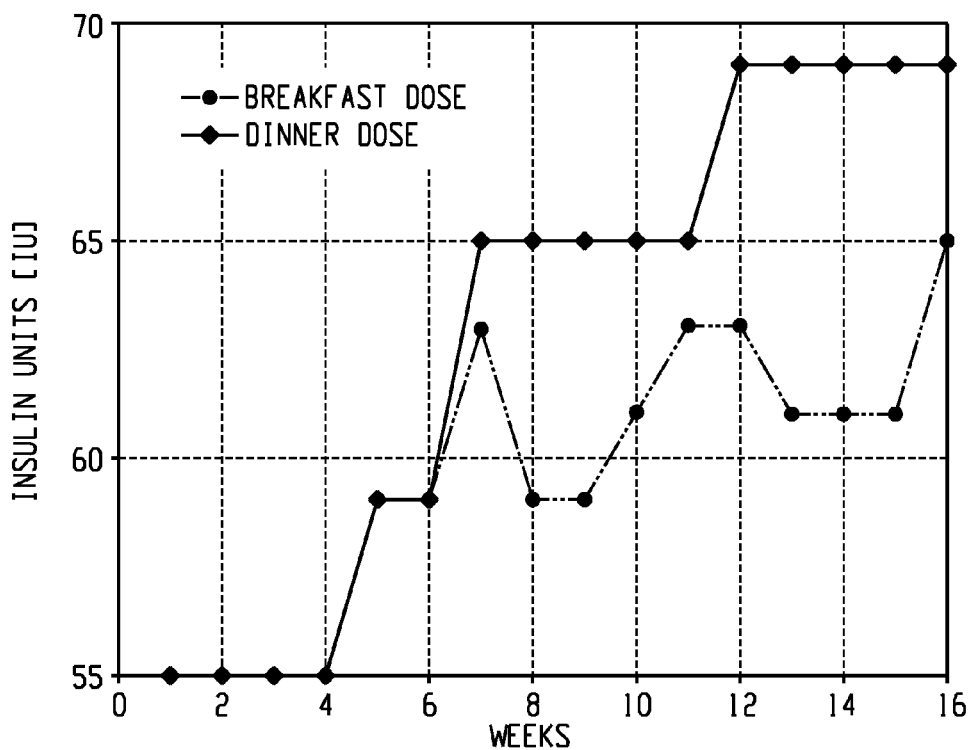
FIG. 27 illustrates insulin dosage of a subject on premixed insulin therapy.

FIG. 26 and FIG. 27 illustrate that certain disclosed embodiments had the ability to adjust different dosage component independently for a patient on premixed therapy. In weeks 6-9 and 12-16 the patient is experiencing some hypoglycemia throughout the day to which the embodiments respond by reducing the breakfast dosage component while the dinner component may still increase. This patient had week 0 A1C of 9.1%, week 4 of 8%, and week 16 of 5.8%.

Figure 28:
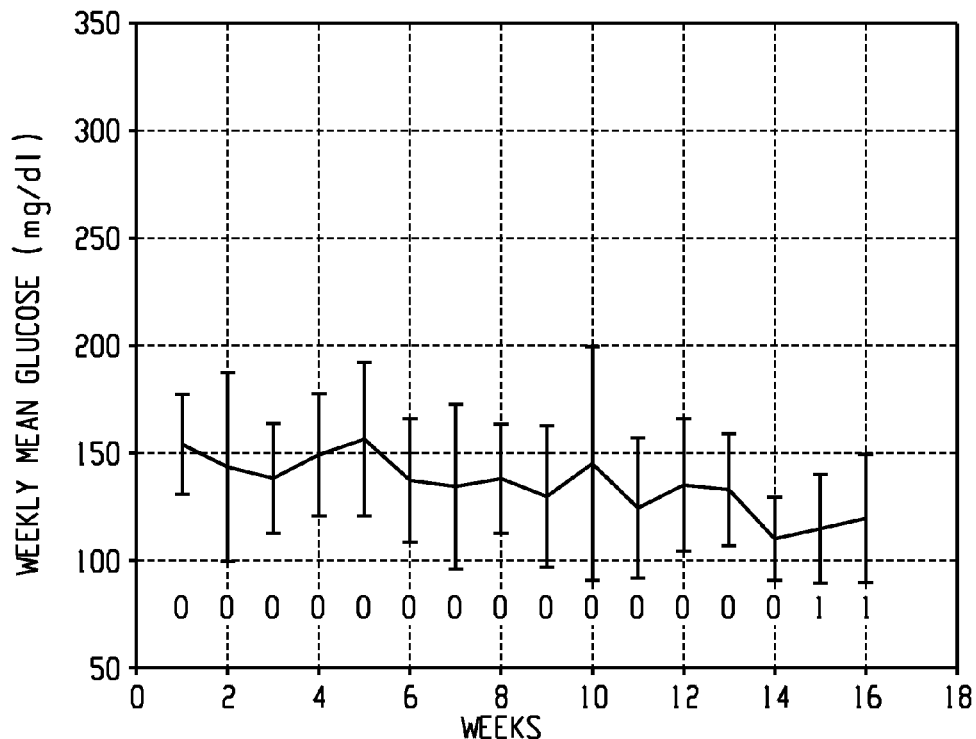
FIG. 28 illustrates blood glucose levels of a subject taking a relatively small daily total of ~45 units per day almost equally divided between basal and bolus.
Figure 29:
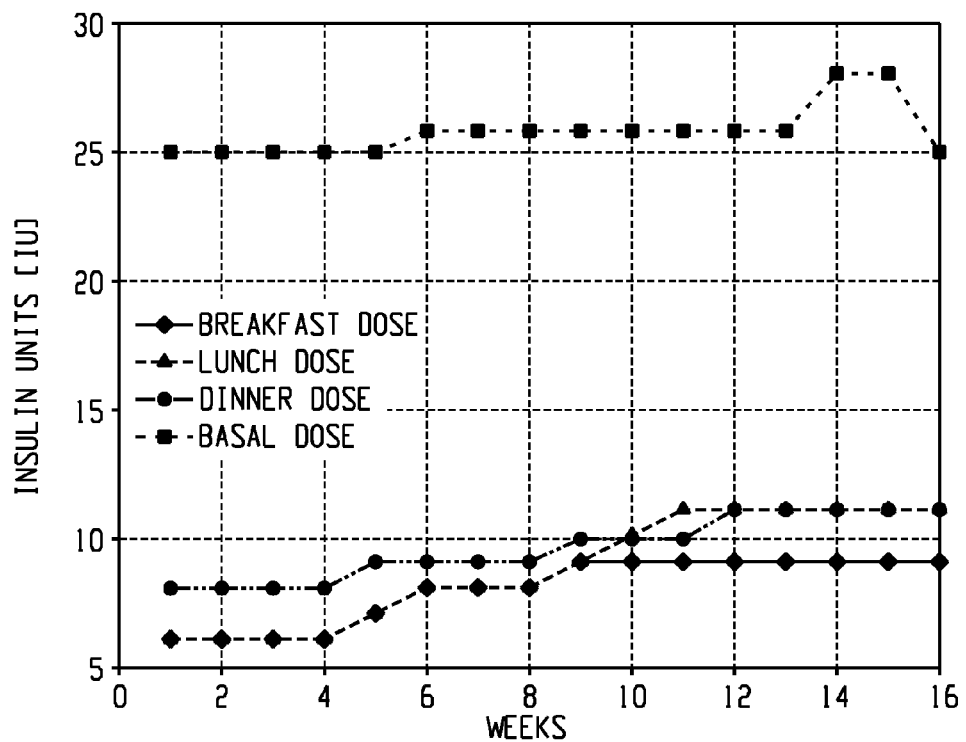
FIG. 29 illustrates insulin dosage of a subject taking a relatively small daily total of ~45 units per day almost equally divided between basal and bolus.

FIG. 28 illustrates a patient taking a relatively small daily total of ~45 units per day almost equally divided between basal and bolus. The patient mean glucose during the run-in period is almost at target hovering just below 150 mg/dl, yet A1C is 9% in week 0 and 8.4% in week 4. Certain embodiments are capable of further improving glycemic balance by slowly increasing the independent bolus dosage components to a final daily total of ~57 units/day. Week 16 A1C is improved to 7.4% with only two hypoglycemic episodes one in each of the final two weeks. FIG. 29 illustrates that basal insulin starts at 24 and ends at 25 units/day with a peak of 28 units/day for weeks 14-15. At the same time: breakfast dosage goes from 6 to 9 (+50%), lunch dosage goes from 6 to 11 (+83%), and dinner dosage goes from 8 to 11 (+37%). While the bolus dosage increase may seem dramatic it was achieved in a safe manner with acceptable rate of hypoglycemia and well improved A1C.

These examples illustrate that in certain embodiments the goal of diabetes management may be achieving glycemic balance or improved glycemic composite index weighing both A1C and hypoglycemia.

Certain embodiments of the present disclosure are directed to systems, methods and/or devices for treating a patient's diabetes by providing treatment guidance based whether and by how much to vary at least one of the one or more components in the patient's present insulin dosage regimen to get closer to the patient's desired glycemic balance point.

Certain embodiments of the present disclosure are directed to systems, methods and/or devices for treating a patient's diabetes by providing treatment guidance based whether and by how much to vary at least one of the one or more components in the patient's present insulin dosage regimen to get closer to the patient's desired glycemic balance point and individual time-varying treatment targets.

Certain embodiments of the present disclosure are directed to systems, methods and/or devices for treating a patient's diabetes by providing treatment guidance that are designed to slowly and/or safely guide its user to a better glycemic balance.

Certain embodiments are directed to providing guidance on a dynamic basis for each individual subject in order to move the subject an appropriate glycemic balance.

In certain embodiments, treatment of a patients diabetes by providing treatment guidance using glycemic balance may assumed one or more of the following:
  a) lowering mean glucose increase the chances of experiencing hypoglycemia;
  b) hypoglycemia poses a potential risk for the patients and under certain conditions it should lead to an immediate dosage adjustment (regardless of the synchronic interval);
  c) a single severe hypoglycemic event may be an outlier. As such, it requires an immediate attention but does not reset the synchronous clock;
  d) events may not need to be double counted, in other words, if a dosage component was adjusted in response to (c) that particular severe hypoglycemic data point will typically be ignored and not used again when the synchronic evaluation of the data occurs; and/or
  e) dosage evaluation should typically reflect the current dosage. That is, when an asynchronous, full, dosage adjustment occurs (due to an excessive number of hypoglycemic events over since the last full update) the synchronous clock would be reset and the hypoglycemic events that caused the asynchronous full dosage adjustment expire.

The result is that certain embodiments use a varying length window that contains the events that occurred after the last update but are no older than 7 days (this is done to allow events to expire based on time in the case that there were not enough events recorded in history to adjust dosage). Other time periods may also be used such as 2, 3, 4, 5, 6, 8, 9, 10 11, 12, 13 or 14 days. Certain embodiments may perform at least two types of updates: partial and full.

A partial update may be triggered by a severe hypoglycemic event and immediately adjusts (reduces) the dosage component that presumably caused the severe low. It does not have to reset the clock and may be treated as an outlier until there is more evidence that it wasn't an outlier (i.e, there are more hypoglycemic episodes). In certain embodiments, partial updates are only triggered by severe hypoglycemic episodes. In certain embodiments any low blood glucose value, low meaning below a particular threshold, can lead to either a partial or a full update of the insulin dosage. In certain embodiments two or more low blood glucose levels can lead to a full update. In certain embodiments one severe hypoglycemic episodes and two low blood glucose levels may lead to a full update. In other embodiments, low blood glucose values may only lead to partial updates. In certain embodiments, two or more low blood glucose value per event may lead to a full update. In other embodiments more than 3, 4, or 5 low blood glucose values may result in a full update.

A full update uses the available data in the valid history (for example, newer than the last dosage update and not older than 7 days) to adjust one or more dosage components. In certain embodiments, the full update will adjust all dosage components. In other embodiments, the full update will adjust one or more dosage components. Other time periods may also be used such as 2, 3, 4, 5, 6, 8, 9, 10 11, 12, 13 or 14 days. It is assumed that this data set reflects the up-to-date efficacy of the active dosage. In certain embodiments, a full update resets the synchronous clock thus causing the events that were part of this dosage adjustment to expire by becoming older than the most recent dosage timestamp. In certain embodiments, a full update resets the synchronous clock thus causing a substantial portion of the events that were part of this dosage adjustment to expire by becoming older than the most recent dosage timestamp. In certain embodiments, a full update resets the synchronous clock thus causing all of the events that were part of this dosage adjustment to expire by becoming older than the most recent dosage timestamp. In certain embodiments, a full update resets the synchronous clock thus causing a portion of the events that were part of this dosage adjustment to expire by becoming older than the most recent dosage timestamp.

In certain embodiments, full update may be triggered by time, by the determination that frequency of hypoglycemia exceeded certain limits, or combinations thereof. A full update can also be triggered by external interventions, such as by a treating clinician or by incorporating additional knowledge that may affect the user metabolic state. Such knowledge may be that the user has started or discontinued other drugs, or the development of physiological conditions weather temporal sickness like the flu or conditions like end stage renal failure. Other examples that can trigger a full update are a visit to the emergency room, any sort of trauma injury, or other medical conditions that would lead someone knowledgeable in this field to reset insulin dosage or regimen or both.

In certain embodiments, a full update may be triggered by time, for example, more than 7 days have passed since last update. In such cases each data set is evaluated for completeness. Certain embodiments require at least 3 data points per event. If a certain event has less than 3 data points it is declared as missing data. If data is missing from one event then certain safety measures are applied to make sure that the remaining dosage component are not going to change too aggressively. For example, If more than 1 data set is missing then it may be decided not to adjust dosage.

In certain embodiments, full update can also be triggered by the determination that frequency of hypoglycemia exceeded certain limits. In such cases it is highly likely that there is less than 3 data points per event. Nonetheless, since the full update was triggered for safety certain embodiments use whatever data is available in memory.

The logic behind certain embodiments is that a) you have to let a dosage settle in; and, b) if a full update occurred than the events (including low) have to expire otherwise certain embodiments would be accounting for events that do not reflect the efficacy of the current dosage (i.e., hypoglycemic episodes that occurred before the active dosage was instated).

In certain embodiments one or more of the following may be combined:

1) Increasing insulin dosage may be done at a more gradual pace. For example, certain embodiments may not allow more than 3, 4, 5, or 6 consecutive increases to insulin dosage. This results in slower increases of dosage which may have longer terms effects: for example if a subject starts with 50 units a day and mean glucose levels in the 200s their dosage can increase 20%-25% for several weeks leading them to a daily total of about 100 units in 4 weeks. While each change was small the cumulative effect may take time to settle in. As can be seen in the subject illustrated in FIGS. 16 and 17 mean glucose is coming down significantly in weeks 9 and 13 although insulin dosage is unchanged from previous week.
2) Hypoglycemia is an inherent part of insulin therapy. There is no need to respond to it either aggressively or conservatively unless it reflects on the active dosage.
3) Limited correlation between events. Certain embodiments treat each event set independently. Correlation between events in some embodiments is only considered when data is missing.
4) Certain embodiments make an attempt to prevent unstable oscillations by limiting an increase that followed a decrease not to exceed the level that caused the previous decrease.

In certain embodiments, glycemic index (GI) can be defined as the minimum of the average and the median of a particular data set, e.g., historic blood glucose level tagged as 'Lunch' during the period under evaluation. For a regimen of basal-bolus insulin therapy, GI can then be used to adjust the breakfast dosage component in AIDF according to the following table 2 where Δ is a number of insulin units to be added to the current breakfast dosage component:

TABLE 2

| GI | Δ fixed meal bolus | Δ for carbohydrate counting |
|---|---|---|
| 0-50 | −MAX(1, INT_MIN[0.1 * BD(k), 0.2 * BD(k)]) | MAX(1, INT_MIN[(0.1 * BD(k), 0.2 * BD(k)]) |
| 51-80 | −MAX(1, INT_MIN[0.05 * BD(k) 0.1 * BD(k)]) | MAX(1, INT_MIN[(0.05 * BD(k), 0.1 * BD(k)]) |
| 81-135 | (0) | (0) |
| 136-200 | MAX(1, INT_MIN[0.05 * BD(k) 0.1 * BD(k)]) | −MAX(1, INT_MIN[(0.05 * BD(k), 0.1 * BD(k)]) |
| 201-250 | MAX(1, INT_MIN[0.1 * BD(k), 0.2 * BD(k)]) | −MAX(1, INT_MIN[(0.1 * BD(k), 0.2 * BD(k)]) |
| 251-300 | MAX(1, INT_MIN[0.15 * BD(k), 0.25 * BD(k)]) | −MAX(1, INT_MIN[0.15 * BD(k), 0.25 * BD(k)]) |
| 301+ | MAX(1, INT_MIN[0.2 * BD(k), 0.3 * BD(k)]) | −MAX(1, INT_MIN[0.2 * BD(k), 0.3 * BD(k)]) |

Wherein for certain embodiments MAX is the maximum of; INT_MIN is the minimal integer within a given range; and BD(k) refers to the breakfast dosage component within the active IDF. Other ranges of can also be used on the column in the left hand side. For example, GI ranges can be 0-60, 61-70, 71-120, 121-180, 181-230, 231-280, and above 281. Other examples are also valid. It would be understood that if a patient is using a fixed breakfast bolus dose of 10 units and GI=140 than the new breakfast dosage component is adjusted to be 11 units. At the same time, if the patient is using a carbohydrate to insulin ratio for breakfast of 1 insulin units to 10 grams of carbohydrates then according to the right-hand column the new dosage component would be a ratio of 1 [IU]:9 [grams of carbohydrates].

In certain embodiments different tables can be used to adjust different dosage components. For example while breakfast dosage component may be adjusted according to the example given in above, certain embodiments may use the following table 3 to adjust the dinner dosage component.

TABLE 3

| GI | Δ fixed meal bolus | Δ for carbohydrate counting |
|---|---|---|
| 0-50 | −MAX(1, INT_MIN[0.1 * DD(k), 0.2 * DD(k)]) | MAX(1, INT_MIN[0.1 * DD(k), 0.2 * DD(k)]) |
| 51-100 | −MAX(1, INT_MIN[0.05 * DD(k), 0.1 * DD(k)]) | MAX(1, INT_MIN[0.05 * DD(k), 0.1 * DD(k)]) |
| 101-200 | (0) | (0) |
| 201-250 | MAX(1, INT_MIN[0.05 * DD(k), 0.1 * DD(k)]) | −MAX(1, INT_MIN[0.05 * DD(k), 0.1 * DD(k)]) |
| 251-300 | MAX(1, INT_MIN[0.1 * DD(k), 0.2 * DD(k)]) | −MAX(1, INT_MIN[0.1 * DD(k), 0.2 * DD(k)]) |
| 301+ | MAX(1, INT_MIN[0.15 * DD(k), 0.25 * DD(k)]) | −MAX(1, INT_MIN[0.15 * DD(k), 0.25 * DD(k)]) |

Wherein DD(k) refers to the dinner dosage component of the AIDF.

In certain embodiments, yet another tables can be used to adjust the long acting insulin dosage component. For example while breakfast dosage component or dinner dosage components may be adjusted according to the aforementioned examples, certain embodiments may use the following table 4 to adjust the long acting dosage component based on breakfast glucose data

TABLE 4

| GI | Δ |
|---|---|
| 0-50 | −MAX(1, INT_MIN[0.1 * LD(k), 0.2 * LD(k)]) |
| 51-100 | −MAX(1, INT_MIN[0.05 * LD(k), 0.1 * LD(k)]) |
| 101-135 | 0 |
| 136-200 | MAX(1, INT_MIN[0.05 * LD(k), 0.1 * LD(k)]) |
| 201-250 | MAX(1, INT_MIN[0.1 * LD(k), 0.2 * LD(k)]) |
| 251-300 | MAX(1, INT_MIN[0.15 * LD(k), 0.25 * LD(k)]) |
| 301+ | MAX(1, INT_MIN[0.2 * LD(k), 0.3 * LD(k)]) |

Managing Population of Diabetics

In certain embodiments, it is desired to have a group of people with insulin-treated diabetes better manage their blood glucose levels. Such embodiments can be used to significantly reduce cost of health care. For example, it is well documented that high hemoglobin A1C is a contributing factor to a significantly higher chances of developing diabetes related complications. Studies have shown that reducing a patient's A1C from 9% to 7% reduces his chances of developing retinophaty by about 76%. As nearly 80% of health care costs are due to hospitalizations, readmissions, or visits to the emergency room, it is useful to reduce average A1C within a population as a tool to reduce costs of health care. It is also useful not to reduce A1C below a certain threshold as low A1C have been shown to be a high risk factor for severe hypoglycemia. Since hypoglycemia is the leading cause for emergency room visits for people with insulin treated diabetes, it is useful to reduce the rate of hypoglycemia of a given population as a way to reduce overall costs of health care.

In certain embodiments it is desired to enroll a patient population to a service that adjusts insulin dosage as a way to improve diabetes prognosis by reducing A1C and/or the rate of hypoglycemia leading to a reduction in health care costs. For example, enrolling a group of patients that are 21-70 years of age and had a clinical diagnosis of type 1 or type 2 diabetes for at least one year. In this example, patients may be excluded if they have a body mass index (BMI)≥45 $kg/m^2$; severe impairment of cardiac, hepatic, or renal functions; psychological, or cognitive impairment; more than two episodes of severe hypoglycemia in the past year; or a history of hypoglycemia unawareness. Eligible patients can be enrolled into one of 3 treatment groups which included patients with: I. suboptimally controlled type 1 diabetes (A1C≥7.4%) treated with basal-bolus insulin therapy that may incorporate carbohydrate-counting; II. suboptimally controlled type 2 diabetes (A1C≥7.4%) treated with basal-bolus insulin therapy (without carbohydrate-counting); and III. suboptimally controlled type 2 diabetes (A1C>7.8%) treated with twice daily biphasic insulin.

In this example, it was useful to use the first 4 weeks as a baseline and allow patients to continue their pre-enrollment regimens without intervention. During the following 12 weeks, self-measured blood glucose readings reported on patients' diaries can be processed weekly by certain embodiments which recommends a new insulin dosage. Although generally encouraged to follow dosage recommendations, patients are allowed to deviate from the prescribed dosage during unusual situations (e.g. anticipated physical activity). Patients in Groups I and II are asked to test and record their capillary glucose 4 times a day before meals and before bedtime and patients in group III are asked to test twice a day, before breakfast and dinner. All patients may be asked to measure capillary glucose during the night every 5-9 days. Information captured in diaries included time-stamped scheduled and unscheduled glucose readings, insulin doses, and carbohydrate quantities (Group I only). Reduction of health care costs is measured by improved efficacy: defined in this example as the improvement in self measured weekly mean glucose, and reduction in A1C; and, by improved safety defined as reduction in the frequency of hypoglycemia for patients suffering from a high rate of hypoglycemia, e.g., more than 3 events per week, and maintaining rate of hypoglycemia at an acceptable level, e.g., no more than one event per week, for everyone else. In this example, hypoglycemia is defined as a blood glucose<65 mg/dl.

Using certain disclosed embodiments a patient population can be treated to improve diabetes management and reduce health care costs by providing them with a device that replaces their glucose meters and automatically uses the plurality of historic glucose data to adjust insulin therapy such that the population reaches a better glycemic balance point.

In this example, using certain disclosed embodiments, can lead to significant reduction in A1C in just 12 weeks, for example from a baseline A1C of 8.4% to an A1C of 7.9%, and reduction in weekly mean glucose from a baseline of 174 mg/dl to an endpoint of 163 mg/dl. And, for patient with high frequency of hypoglycemia reducing its rate from 3.2 events per week to 1.9 events per week without increasing A1C level in a statistically significant manner. And, for patients without frequent hypoglycemia reducing A1C from 8.5% at baseline to 7.8%, mean glucose from 182 mg/dl to 155 mg/dl without increasing frequency of hypoglycemia, of 0.5 events per week at baseline, in a statistically significant manner Achieving the above results lead to reduction in the number of office visits and/or the number of calls from patients to health care providers, leading to short term health care costs saving. Furthermore, maintaining the above results over a period of time can lead to significant reduction in the development of diabetes related complications or visits to the emergency room resulting in a significant health care costs reduction.

Figure 30:
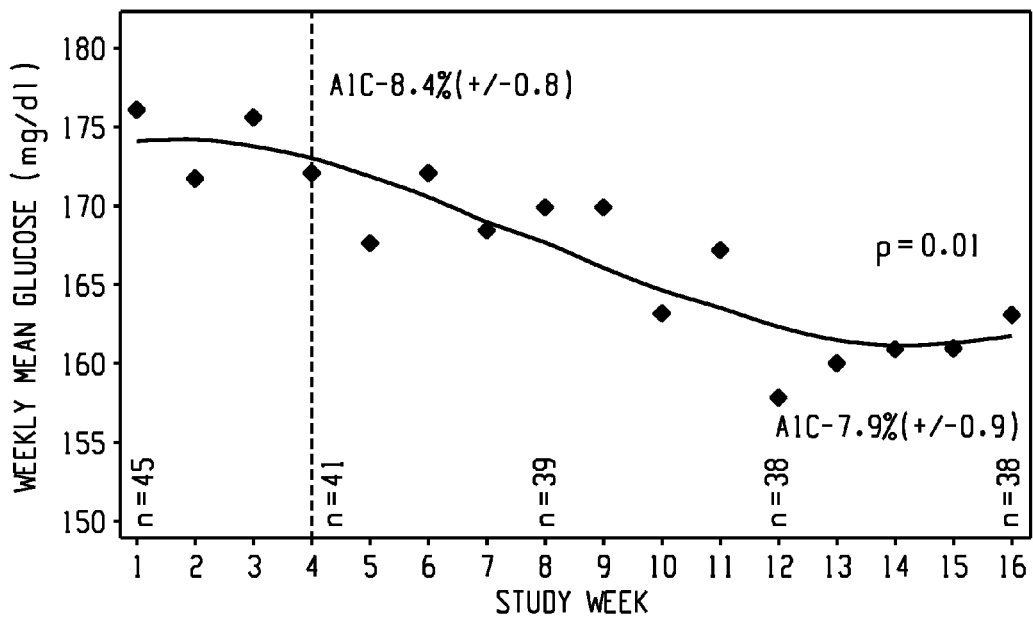
FIG. 30 illustrates the weekly mean glucose (and regression line), cumulatively for all patients in this example, according to certain embodiments.
Figure 31:
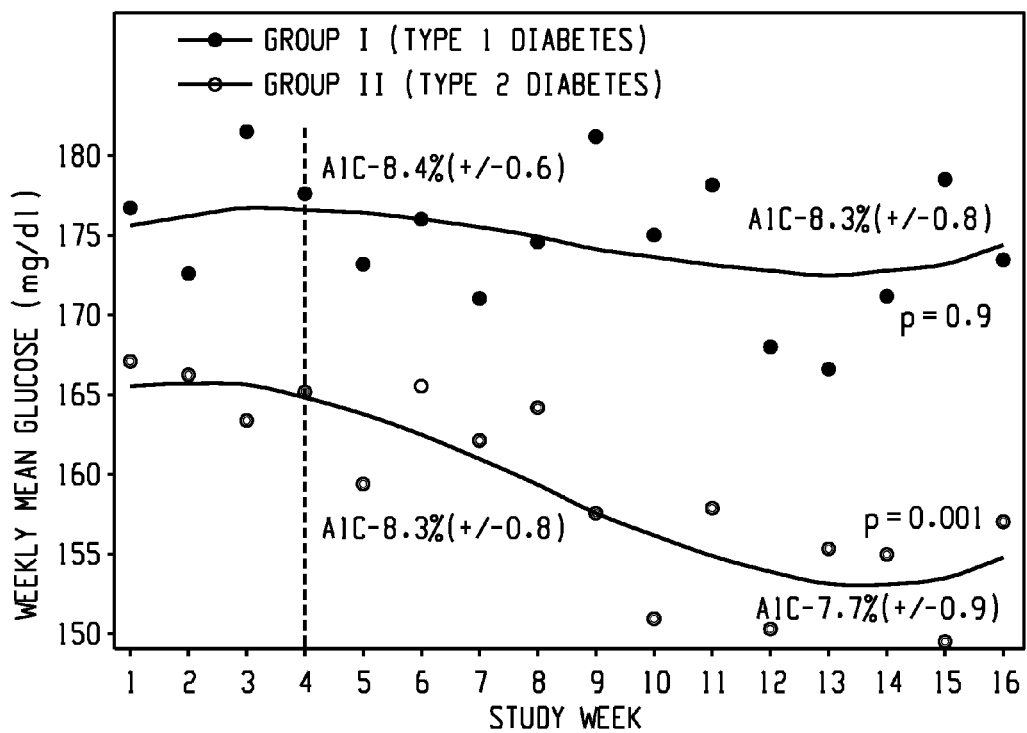
FIG. 31 illustrates the weekly mean glucose (and regression line), cumulatively in groups I and II in this example, according to certain embodiments.
Figure 32:
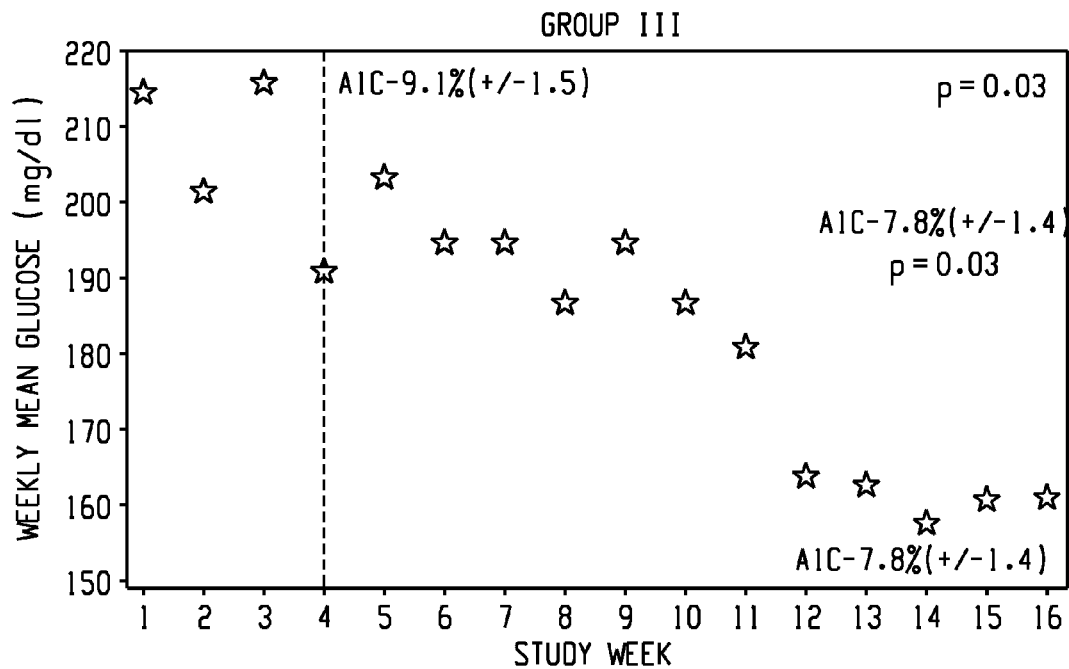
FIG. 32 illustrates the weekly mean glucose in group III (due to lesser data points, a regression line was not plotted) in this example, according to certain embodiments.
Figure 33:
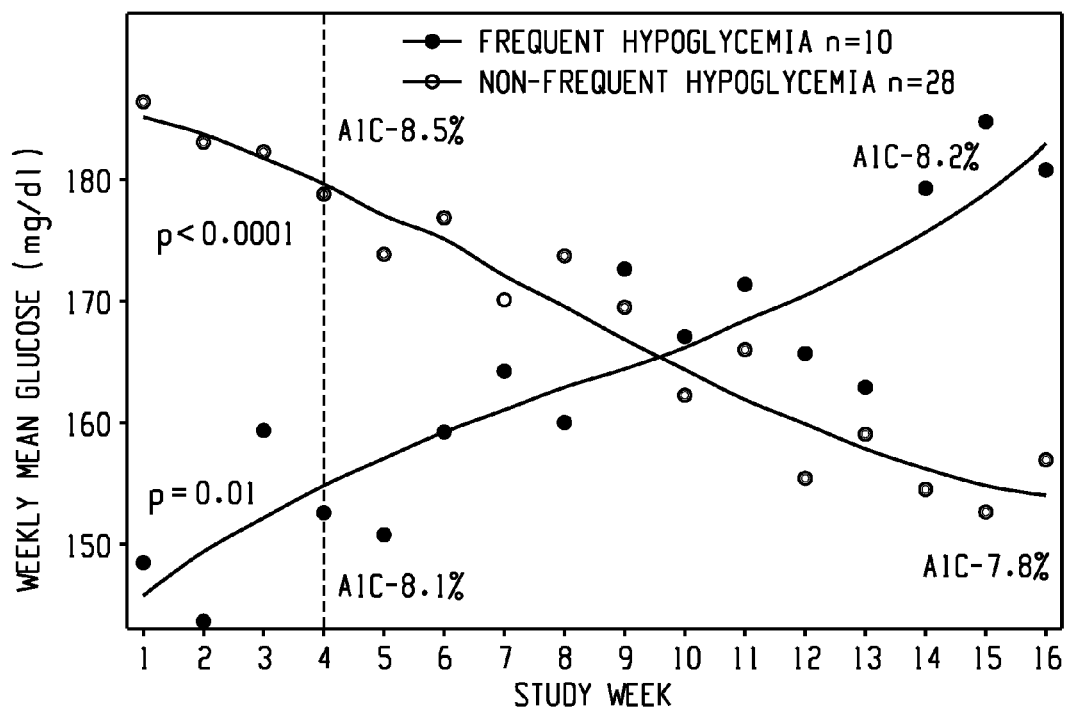
FIG. 33 illustrates the weekly mean glucose (and regression line) of patients with and without frequent hypoglycemia. During the active 12 weeks weekly mean glucose improved when possible in this example, according to certain embodiments.
Figure 34:
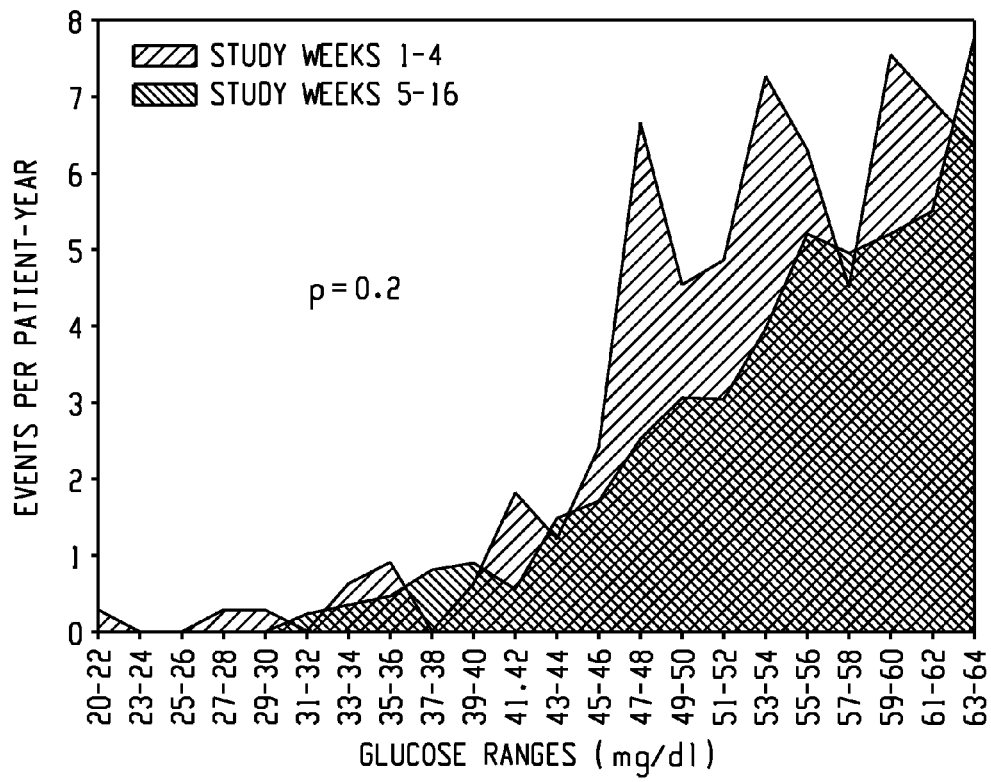
FIG. 34 illustrates the distribution of hypoglycemic glucose readings during the 12-week active phase and the 4-week run-in period in this example, according to certain embodiments.
Figure 35:
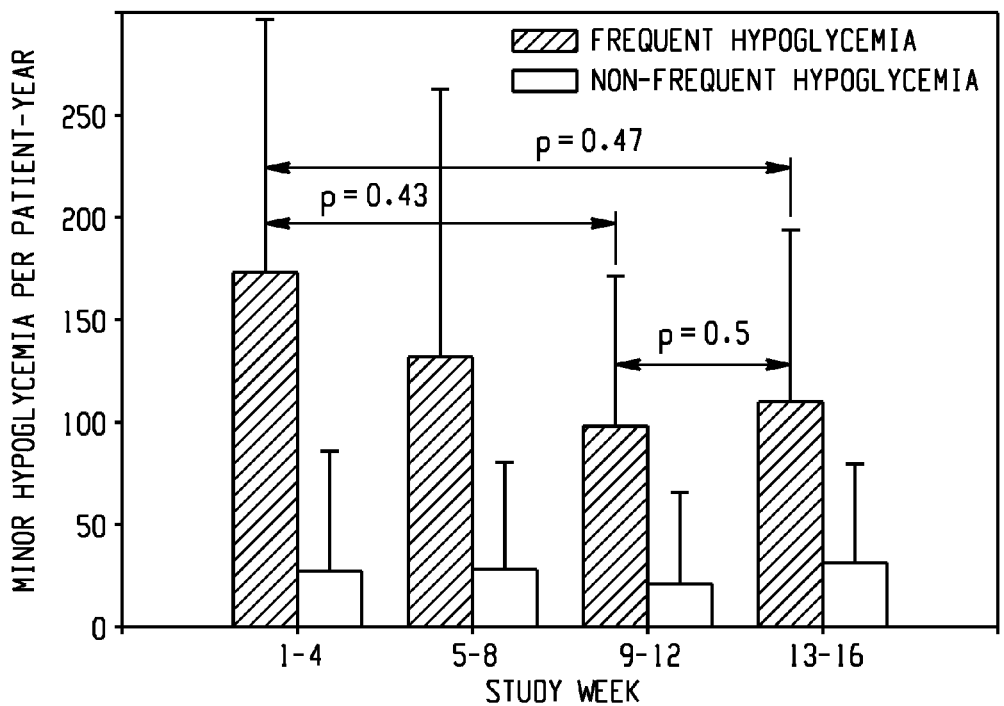
FIG. 35 illustrates the frequency of minor hypoglycemia (glucose<65 mg/dl) during each quartile for patients with or without frequent hypoglycemia (>85 events per patient-year) in this example, according to certain embodiments.

In this example, reduction in mean glucose is achieved for all members of the population as seen in FIG. 30. Using certain disclosed embodiments, significant reduction in mean glucose and hemoglobin A1C can be achieved with population members having type 2 diabetes as seen in FIG. 31 and FIG. 32. Better glycemic balance is achieved by reducing mean glucose for patient without frequent hypoglycemia while increasing mean glucose for patients with frequent hypoglycemia as seen in FIG. 33. Using certain disclosed embodiments it is possible not only to reduce the number of hypoglycemia events but also to shift their distribution such that if an hypoglycemic event occurs it is likelier to have a higher low blood glucose level, for example above 50 mg/dl, as seen in FIG. 34. In certain embodiments, statistically significant reduction in the frequency of hypoglycemia is achieved without an increase in A1C, while statistically significant reduction in A1C is achieved without an increase in the frequency of hypoglycemia, as seen in FIG. 35. In certain embodiments it is useful to increase daily total insulin dosage to achieve reduction in A1C.

Figure 36:
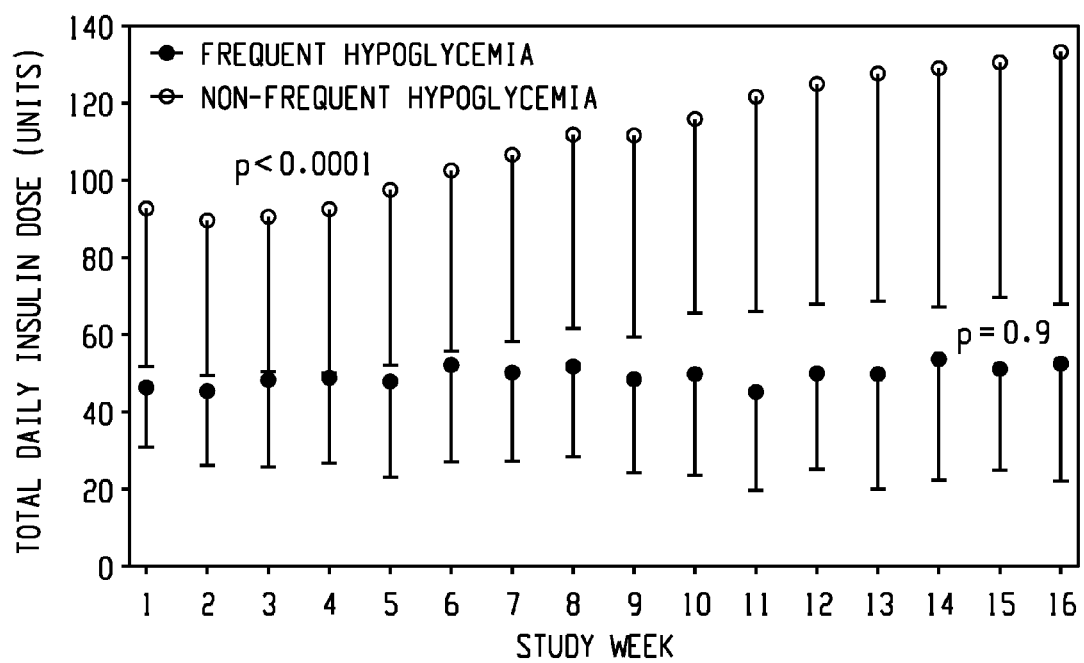
FIG. 36 illustrates the total daily insulin in patients with different frequencies of minor hypoglycemia. During the active 12-week period, the frequency and severity of hypoglycemia decreased in this example, according to certain embodiments.

In certain embodiments it is useful to achieve reduction in the frequency of hypoglycemia by changing the distribution of insulin between different administration points rather than reducing the daily total insulin dosage, as seen in FIG. 36.

Certain embodiments are directed to methods, systems and/or devices for treating a patient's diabetes by providing treatment guidance wherein the frequency of hypoglycemic events is reduced without significantly reducing the total amount of insulin used by the patient. For example, a method for treating a patient's diabetes by providing treatment guidance, the method comprising: storing one or more components of the patient's insulin dosage regimen; obtaining data corresponding to the patient's blood glucose-level measurements determined at a plurality of times; tagging each of the blood glucose-level measurements with an identifier reflective of when or why the reading was obtained; and determining the patient's current glycemic state relative to a desired balance point; and determining from at least one of a plurality of the data corresponding to the patient's blood glucose-level measurements whether and by how much to vary at least one of the one or more components in the patient's present insulin dosage regimen to get closer to the patient's desired balance point, without significantly reducing the total amount of insulin used by the patient; wherein the desired balance point is the patient's lowest blood glucose-level within a predetermined range achievable before increasing the frequency of hypoglycemic events above a predetermined threshold.

Certain embodiments are directed to apparatus for improving the health of a diabetic population, wherein the frequency of hypoglycemic events is reduced without significantly reducing the total amount of insulin used by the patient. For example, an apparatus comprising: a processor and a computer readable medium coupled to the processor and collectively capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point, without significantly reducing the total amount of insulin used by the patient; wherein the desired balance point is the patient's lowest blood glucose-level within a predetermined range achievable before the frequency of hypoglycemic events exceeds a predetermined threshold.

Certain embodiments are directed to methods, systems and/or devices for improving the health of a diabetic population, wherein the frequency of hypoglycemic events is reduced without significantly reducing the total amount of insulin used by the patients. For example, a method for improving the health of a diabetic population, the method comprising: identifying at least one diabetic patient; treating the a least one diabetic patient to control the patient's blood glucose level; wherein the patient's blood glucose level is controlled using a device capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point without significantly reducing the total amount of insulin used by the patient; wherein the desired balance point is the patient's lowest blood glucose-level within a predetermined range achievable before the frequency of hypoglycemic events exceeds a predetermined threshold.

In certain embodiments, the present disclosure comprehends systems, methods, and/or devices for optimizing the insulin dosage regimen in diabetes patients over time—such as in between clinic visits—to thereby enhance diabetes control.

As used herein with respect to certain embodiments, the term "insulin dose" means and refers to the quantity of insulin taken on any single occasion, while the term "insulin dosage regimen" refers to and means the set of instructions (typically defined by the patient's physician or other healthcare professional) defining when and how much insulin to take in a given period of time and/or under certain conditions. One conventional insulin dosage regimen comprises several components, including a long-acting insulin dosage component, a plasma glucose correction factor component, and a carbohydrate ratio component. Thus, for instance, an exemplary insulin dosage regimen for a patient might be as follows: 25 units of long acting insulin at bedtime; 1 unit of fast-acting insulin for every 10 grams of ingested carbohydrates; and 1 unit of fast-acting insulin for every 20 mg/dL by which a patient's blood glucose reading exceeds 120 mg/dL.

Referring to FIG. 1, which constitutes a generalized schematic thereof, of certain exemplary embodiments more particularly comprises an apparatus 1 having at least a first memory 10 for storing data inputs corresponding at least to one or more components of a patient's present insulin dosage regimen (whether comprising separate units of long-acting and short-acting insulin, premixed insulin, etc.) and the patient's blood-glucose-level measurements determined at a plurality of times, a processor 20 operatively connected (indicated at line 11) to the at least first memory 10, and a display 30 operatively coupled (indicated at line 31) to the processor and operative to display at least information corresponding to the patient's present insulin dosage regimen. The processor 20 is programmed at least to determine from the data inputs corresponding to the patient's blood-glucose-level measurements determined at a plurality of times whether and by how much to vary at least one or the one or more components of the patient's present insulin dosage regimen. Such variation, if effected, leads to a modification of the patient's present insulin dosage regimen data as stored in the memory 10, as explained further herein. Thus, the data inputs corresponding to the one or more components of the patient's present insulin dosage regimen as stored in the memory device 10 will, at a starting time for employment of the apparatus, constitute an insulin dosage regimen prescribed by a healthcare professional, but those data inputs may subsequently be varied by operation of the apparatus (such as during the time interval between a patient's clinic visits). In the foregoing manner, the apparatus is operative to monitor relevant patient data with each new input of information (such as, at a minimum, the patient's blood-glucose-level measurements), thereby facilitating the optimization of the patient's insulin dosage regimen in between clinic visits.

It is contemplated that the apparatus as generalized herein may be embodied in a variety of forms, including a purpose-built, PDA-like unit, a commercially available device such as a cell-phone, IPHONE, etc. Preferably, though not necessarily, such a device would include data entry means, such as a keypad, touch-screen interface, etc. (indicated generally at the dashed box 40) for the initial input by a healthcare professional of data corresponding at least to a patient's present insulin dosage regimen (and, optionally, such additional data inputs as, for instance, the patient's present weight, defined upper and lower preferred limits for the patient's blood-glucose-level measurements, etc.), as well as the subsequent data inputs corresponding at least to the patient's blood-glucose-level measurements determined at a plurality of times (and, optionally, such additional data inputs as, for instance, the patient's present weight, the number of insulin units administered by the patient, data corresponding to when the patient eats, the carbohydrate content of the foodstuffs eaten, the meal type (e.g., breakfast, lunch, dinner, snack, etc.). As shown, such data entry means 40 are operatively connected (indicated at line 41) to the memory 10.

Display 30 is operative to provide a visual display to the patient, healthcare professional, etc. of pertinent information, including, by way of non-limiting example, information corresponding to the present insulin dosage regimen for the patient, the current insulin dose (i.e., number of insulin units the patient needs to administer on the basis of the latest blood-glucose-level measurement and current insulin dosage regimen), etc. To that end, display 30 is operatively connected to the processor 20, as indicated by the dashed line 31.

As noted, the data entry means 40 may take the form of a touch-screen, in which case the data entry means 40 and display 30 may be combined (such as exemplified by the commercially available IPHONE (Apple, Inc., California)).

Referring then to FIGS. 2 through 5, there are depicted representative images for a display 30 and a touch-screen type, combined display 30/data entry means 40 exemplifying both the patient information that may be provided via the display, as well as the manner of data entry.

Figure 2:
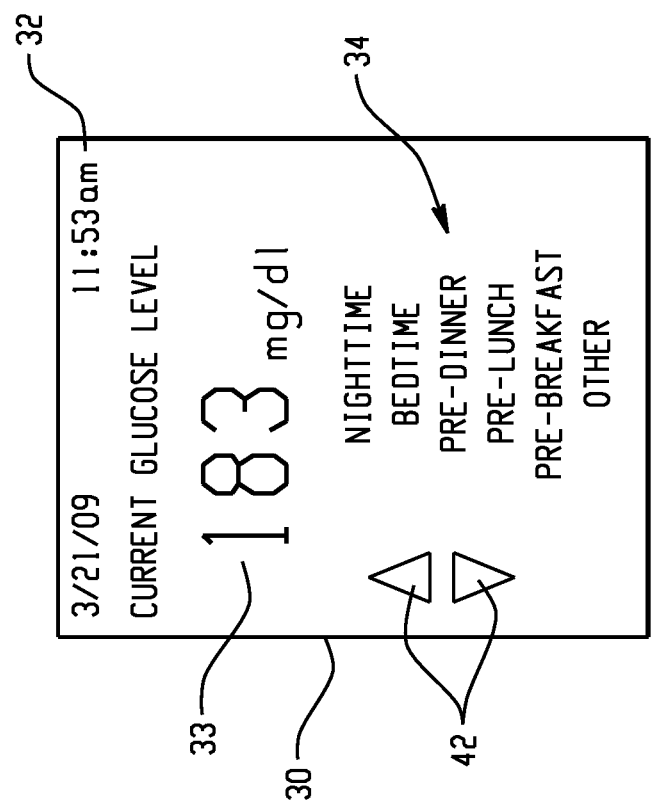
FIG. 2 is a drawing of a representative display for providing information to a patient.

More particularly, FIG. 2 shows a display 30 providing current date/time information 32 as well as the patient's current blood-glucose-level measurement 33 based upon a concurrent entry of that data. FIG. 2 further depicts a pair of scrolling arrows 42 by which the patient is able to scroll through a list 34 of predefined choices representing the time of the patient's said current blood-glucose-level measurement. As explained further herein in association with a description of an exemplary algorithm for implementing certain embodiments, selection of one of these choices will permit the processor to associate the measurement data with the appropriate measurement time for more precise control of the patient's insulin dosage regimen.

Figure 3:
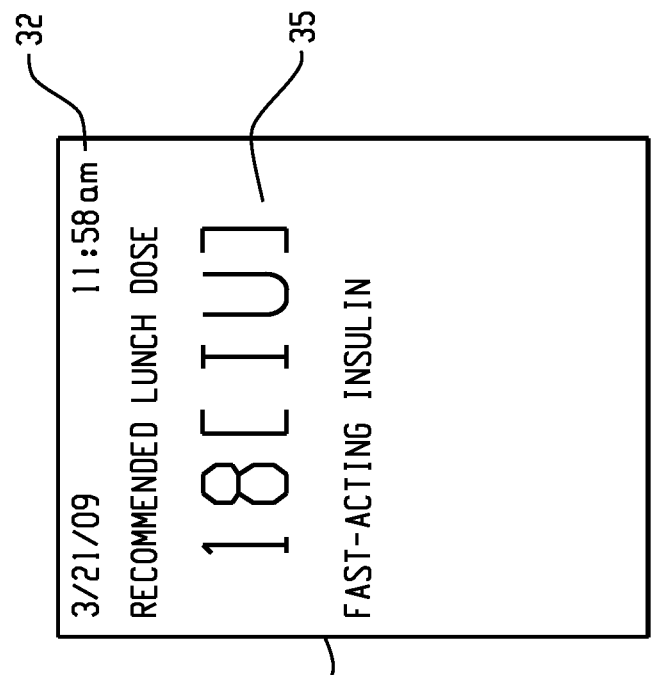
FIG. 3 is a drawing of another representative display for providing information to a patient.

FIG. 3 shows a display 30 providing current date/time information 32, as well as the presently recommended dose of short-acting insulin units 35—based upon the presently defined insulin dosage regimen—for the patient to take at lunchtime.

Figure 4:
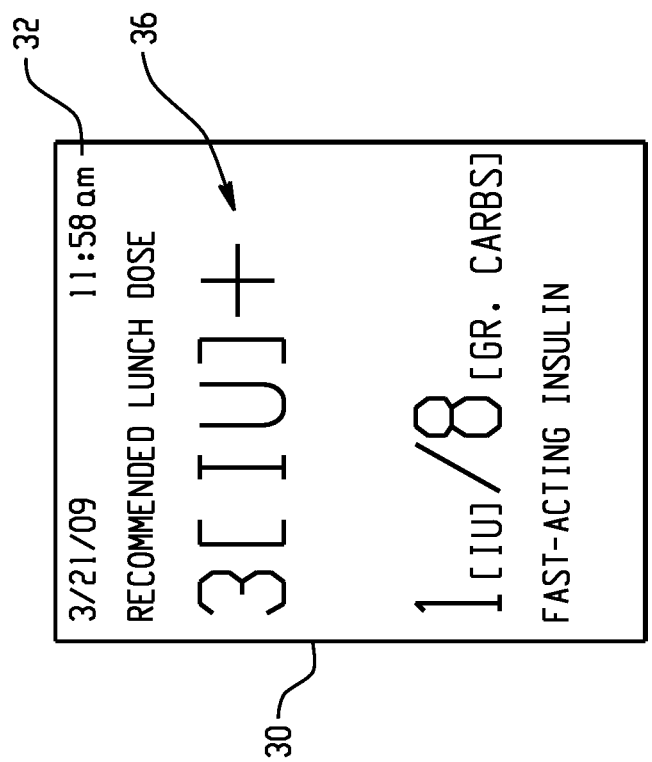
FIG. 4 is a drawing yet another representative display for providing information to a patient.

FIG. 4 shows a display 30 providing current date/time information 32, as well as, according to a conventional "carbohydrate-counting" therapy, the presently recommended base (3 IUs) and additional doses (1 IU per every 8 grams of carbohydrates ingested) of short-acting insulin units 36 for the patient to take at lunchtime—all based upon the presently defined insulin dosage regimen.

Figure 5:
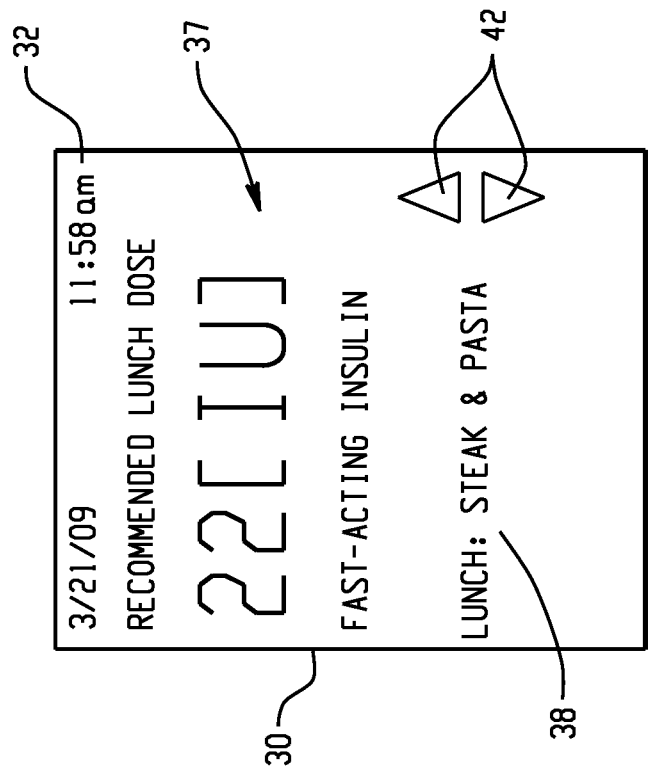
FIG. 5 is a drawing of still another representative display for providing information to a patient.

In FIG. 5, there is shown a display 30 providing current date/time information 32, as well as the presently recommended dose of short-acting insulin units 37—based upon the presently defined insulin dosage regimen—for the patient to take at lunchtime according to a designated amount of carbohydrates to be ingested. As further depicted in FIG. 5, a pair of scrolling arrows 42 are displayed, by which the patient is able to scroll through a list of predefined meal choices 38, each of which will have associated therewith in the memory a number (e.g., grams) of carbohydrates. When the patient selects a meal choice, the processor is able to determine from the number of carbohydrates associated with that meal, and the presently defined insulin dosage regimen, a recommended dose of short-acting insulin for the patient to take (in this example, 22 IUs of short-acting insulin for a lunch of steak and pasta).

Figure 6:
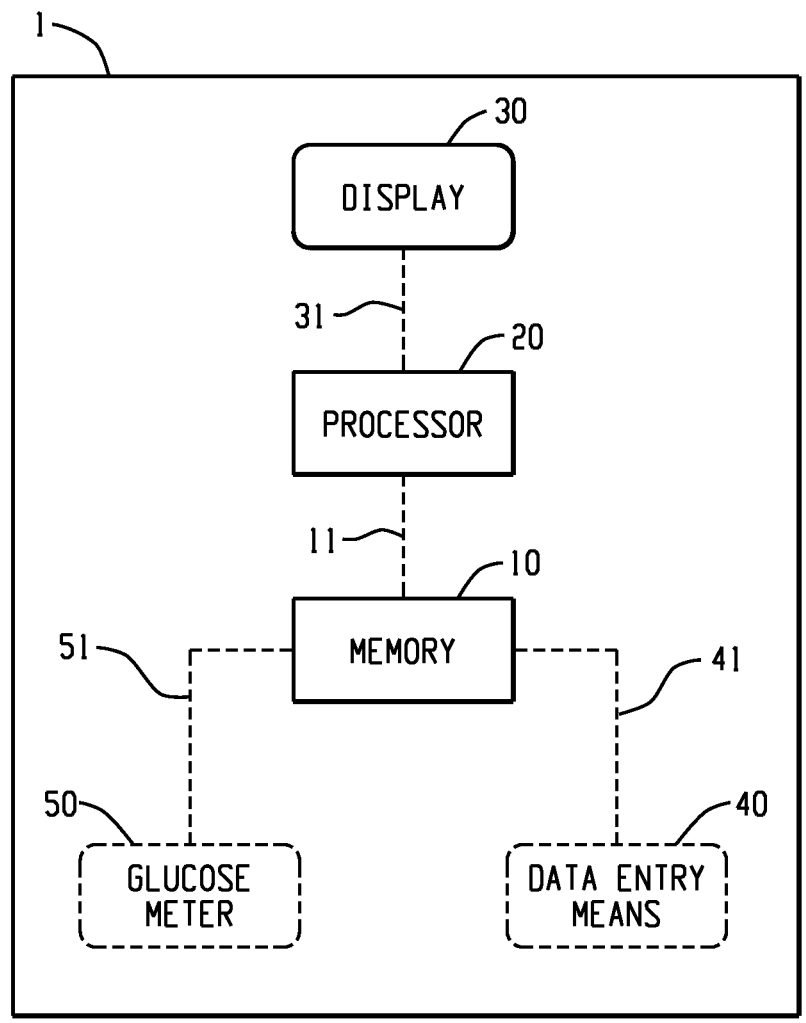
FIG. 6 is a simplified diagram of an apparatus for employing the disclosed system, according to certain embodiments thereof.

In one embodiment thereof, shown in FIG. 6, the apparatus as described herein in respect of FIG. 1 optionally includes a glucose meter (indicated by the dashed box 50) operatively connected (as indicated at line 51) to memory 10 to facilitate the automatic input of data corresponding to the patient's blood-glucose-level measurements directly to the memory 10.

Figure 7:
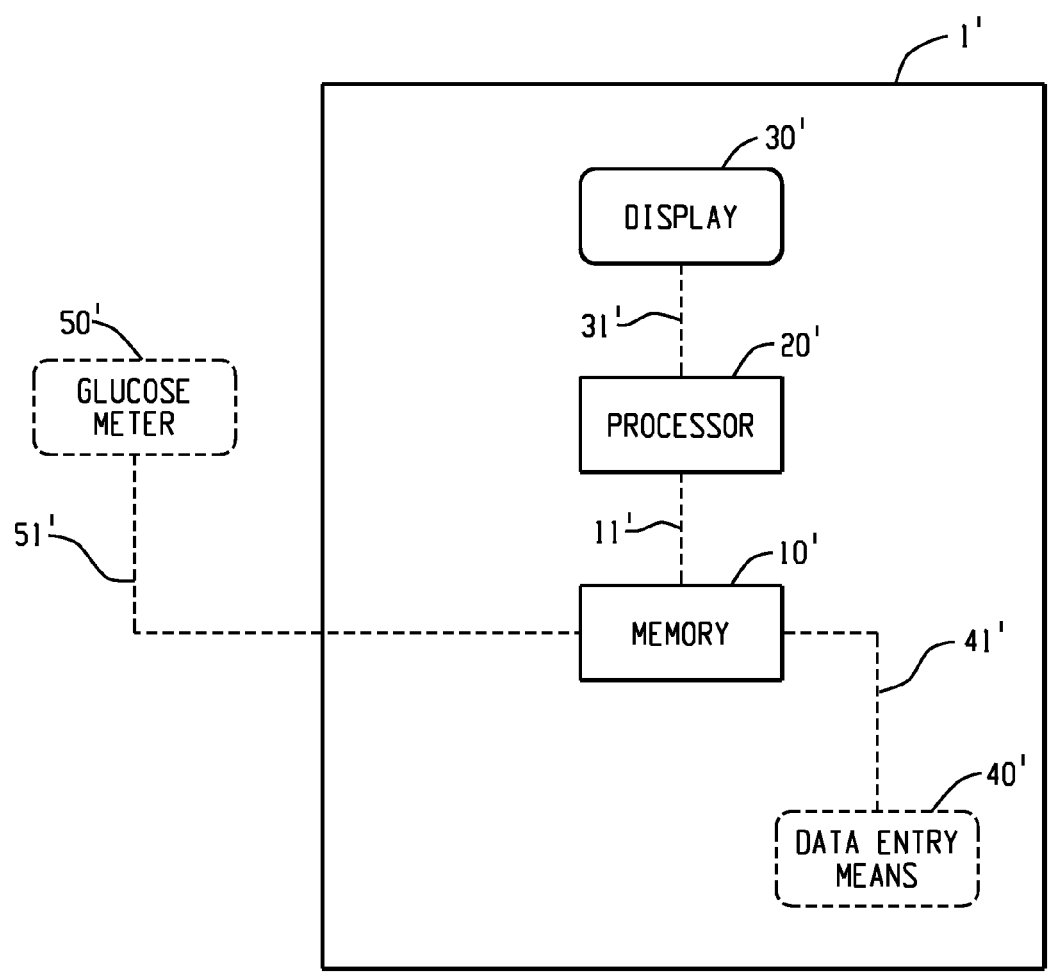
FIG. 7 is a simplified diagram of an apparatus for employing the disclosed system, according to certain embodiments.

Alternatively, it is contemplated that the glucose meter 50' could be provided as a separate unit that is capable of communicating (such as via a cable or wirelessly, represented at line 51') with the device 1' so as to download to the memory 10 the patient's blood-glucose-level measurements, such as shown in FIG. 7.

Figure 8:
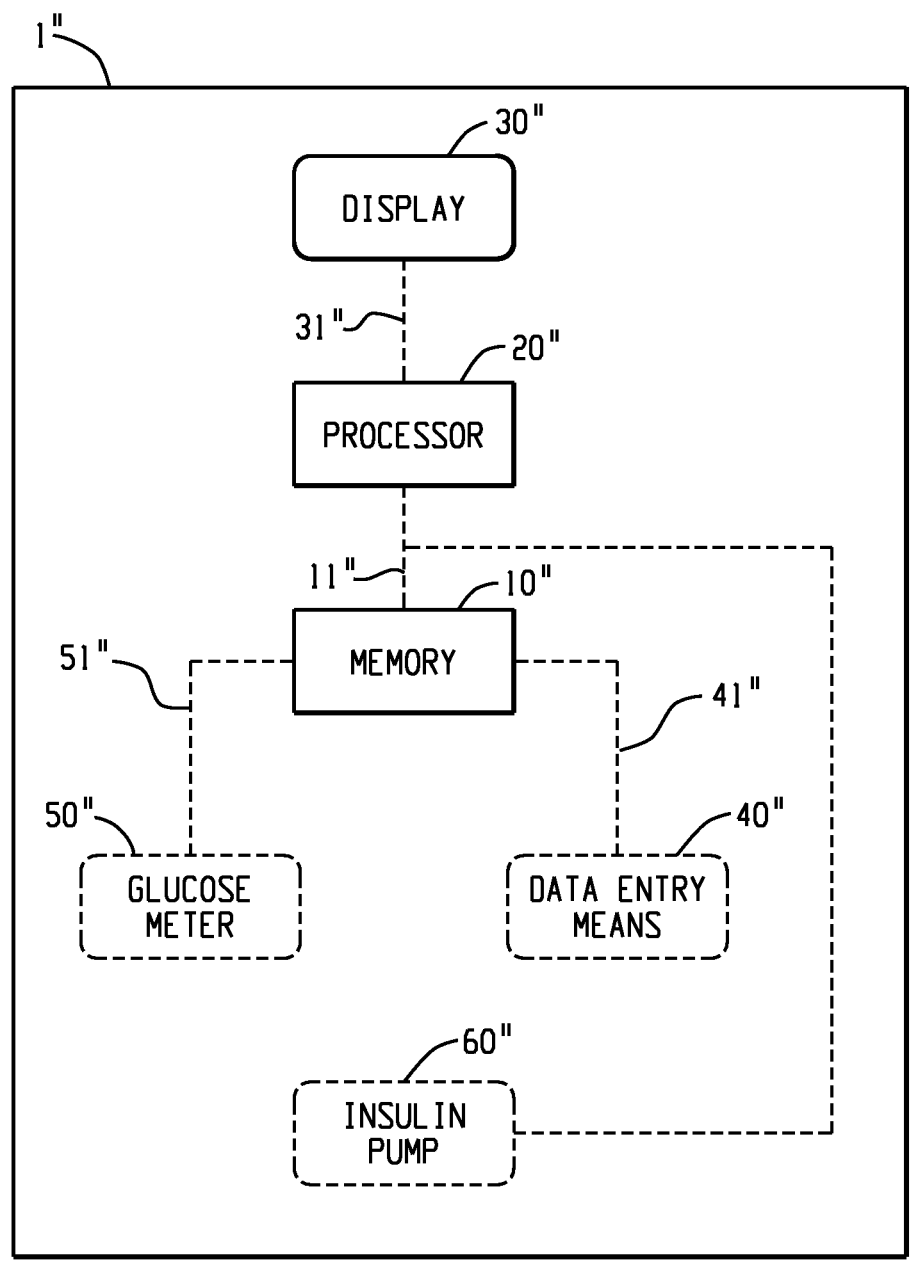
FIG. 8 is a simplified diagram of an apparatus for employing the disclosed system, according to certain embodiments thereof.

According to another embodiment, shown in FIG. 8, the apparatus 1" may be combined with an insulin pump 60" and, optionally, a glucose meter 50" as well. According to this embodiment, the processor 20" is operative to determine from at least the patient's blood-glucose-level measurement data (which may be automatically transferred to the memory 10" where the apparatus is provided with a glucose meter 50", as shown, is connectable to a glucose meter so that these data may be automatically downloaded to the memory 10", or is provided with data entry means 40" so that these data may be input by the patient) whether and by how much to vary the patient's present insulin dosage regimen. The processor 20", which is operatively connected to the insulin pump 60" (indicated at line 61"), is operative to employ the insulin dosage regimen information to control the insulin units provided to the patient via the pump 60". Therefore, the processor 20" and the pump 60" form a semi-automatic, closed-loop system operative to automatically adjust the pump's infusion rate and profile based on at least the patient's blood-glucose-level measurements. This will relieve the burden of having to go to the healthcare provider to adjust the insulin pump's infusion rate and profile, as is conventionally the case. It will be appreciated that, further to this embodiment, the insulin pump 60" may be operative to transfer to the memory 10" data corresponding to the rate at which insulin is delivered to the patient by the pump according to the patient's present insulin dosage regimen. These data may be accessed by the processor 20" to calculate, for example, the amount of insulin units delivered by the pump to the patient over a predefined period of time (e.g., 24 hours). Such data may thus be employed in certain embodiments to more accurately determine a patient's insulin sensitivity, plasma glucose correction factor and carbohydrate ratio, for instance.

Also further to this embodiment, the apparatus 1" may optionally be provided with data entry means, such as a keypad, touch-screen interface, etc. (indicated generally at the dashed box 40") for entry of various data, including, for instance, the initial input by a healthcare professional of data corresponding at least to a patient's present insulin dosage regimen (and, optionally, such additional data inputs as, for instance, the patient's present weight, defined upper and lower preferred limits for the patient's blood-glucose-level measurements, etc.), as well as the subsequent data inputs corresponding at least to the patient's blood-glucose-level measurements determined at a plurality of times (to the extent that this information is not automatically transferred to the memory 10" from the blood glucose meter 50") and, optionally, such additional data inputs as, for instance, the patient's present weight, the number of insulin units administered by the patient, data corresponding to when the patient eats, the carbohydrate content of the foodstuffs eaten, the meal type (e.g., breakfast, lunch, dinner, snack), etc.

Figure 9:
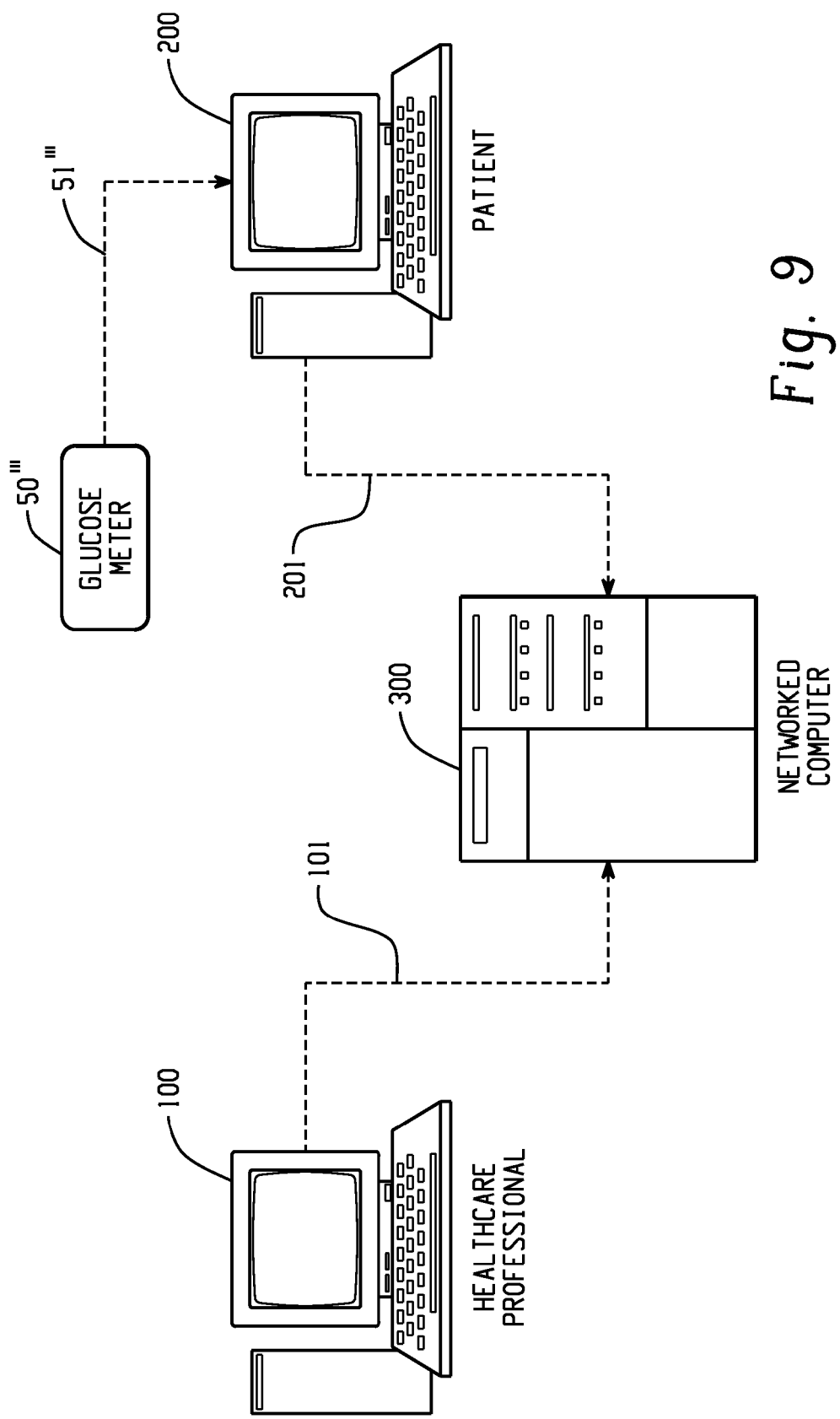
FIG. 9 is a schematic view of an exemplary arrangement, according to certain embodiments.

It is also contemplated that certain embodiments may be effected through the input of data by persons (e.g., patient and healthcare professional) at disparate locations, such as illustrated in FIG. 9. For instance, it is contemplated that the data inputs pertaining to at least the patient's initial insulin dosage regimen may be entered by the healthcare professional at a first location, in the form of a general purpose computer, cell phone, IPHONE, or other device 100 (a general purpose computer is depicted), while the subsequent data inputs (e.g., patient blood-glucose-level readings) may be entered by the patient at a second location, also in the form of a general purpose computer, cell phone, IPHONE, or other device 200 (a general purpose computer is depicted), and these data communicated to a third location, in the form of a computer 300 comprising the at least first memory and the processor. According to this embodiment, the computers 100, 200, 300 may be networked in any known manner (including, for instance, via the internet). Such networking is shown diagrammatically via lines 101 and 201. Thus, for instance, the system may be implemented via a healthcare professional/patient accessible website through which relevant data are input and information respecting any updates to the predefined treatment plan are communicated to the patient and healthcare professional.

Figure 10:
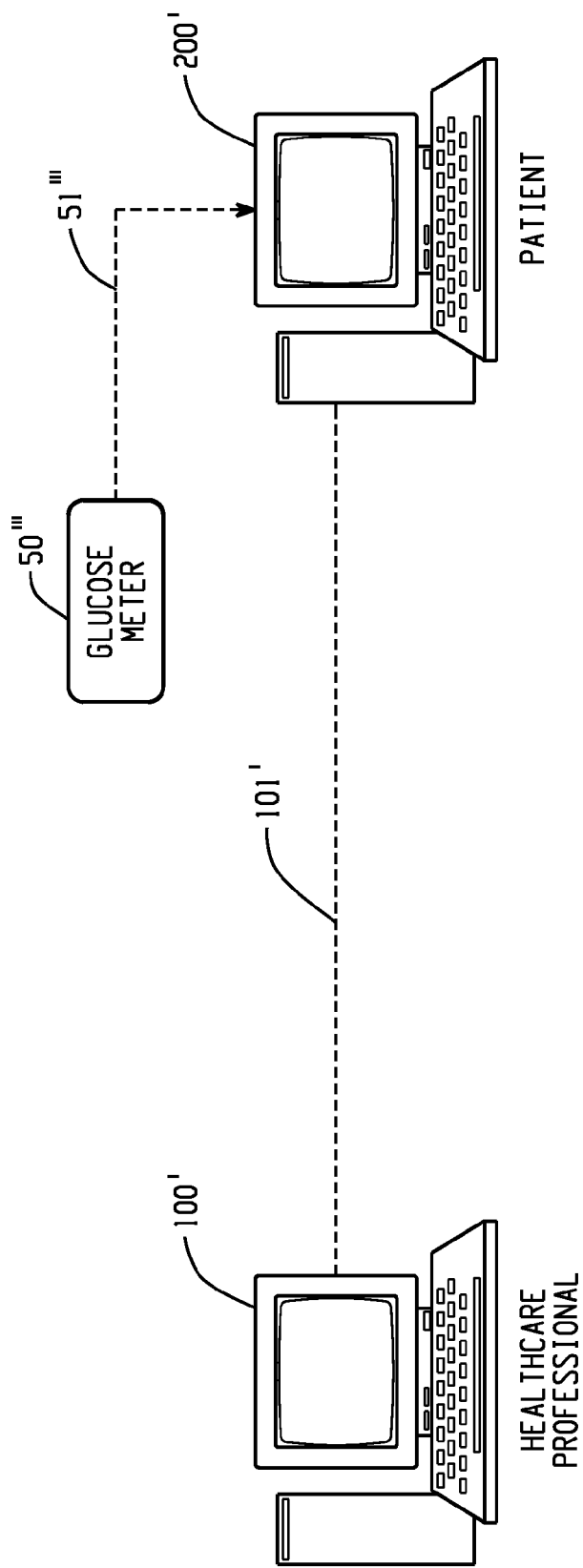
FIG. 10 is a schematic view of an exemplary arrangement for employing, according to certain embodiments.

Alternatively, it is contemplated that certain embodiments may be effected through the input of data via persons (e.g., patient and healthcare professional) at disparate locations, and wherein further one of the persons, such as, in the illustrated example, the patient, is in possession of a single device 200' comprising the processor and memory components, that device 200' being adapted to receive data inputs from a person at a disparate location. FIG. 10. This device 200' could take any form, including a general-purpose computer (such as illustrated), a PDA, cell-phone, purpose-built device such as heretofore described, etc. According to this embodiment, it is contemplated that the data inputs pertaining to at least the patient's initial insulin dosage may be entered (for instance by the healthcare professional) at another location, such as via a general purpose computer, cell phone, or other device 100' (a general purpose computer is depicted) operative to transmit data to the device 200', while the subsequent data inputs (e.g., patient blood-glucose-level measurements) may be entered directly into the device 200'. According to this embodiment, a healthcare professional could remotely input the patient's initial insulin dosage at a first location via the device 100', and that data could then be transmitted to the patient's device 200' where it would be received and stored in the memory thereof. According to a further permutation of this embodiment, the afore described arrangement could also be reversed, such that the patient data inputs (e.g., patient blood-glucose-level measurements) may be entered remotely, such as via a cell phone, computer, etc., at a first location and then transmitted to a remotely situated device comprising the processor and memory components operative to determine whether and by how much to vary the patient's present insulin dosage regimen. According to this further permutation, modifications to the patient's insulin dosage effected by operation of certain embodiments could be transmitted back to the patient via the same, or alternate, means.

Referring again to FIG. 9, it is further contemplated that there may be provided a glucose meter 50''' (including, for instance, in the form of the device as described above in reference to FIG. 6) that can interface 51''' (wirelessly, via a hard-wire connection such as a USB cable, FIREWIRE cable, etc.) with a general purpose computer 200 at the patient's location to download blood-glucose-level measurements for transmission to the computer 300 at the third location. Referring also to FIG. 10, it is further contemplated that this glucose meter 50''' may be adapted to interface 51''' (wirelessly, via a hard-wire connection such as a USB cable, FIREWIRE cable, etc.) with the single device 200', thereby downloading blood-glucose-level measurement data to that device directly.

Figure 11:
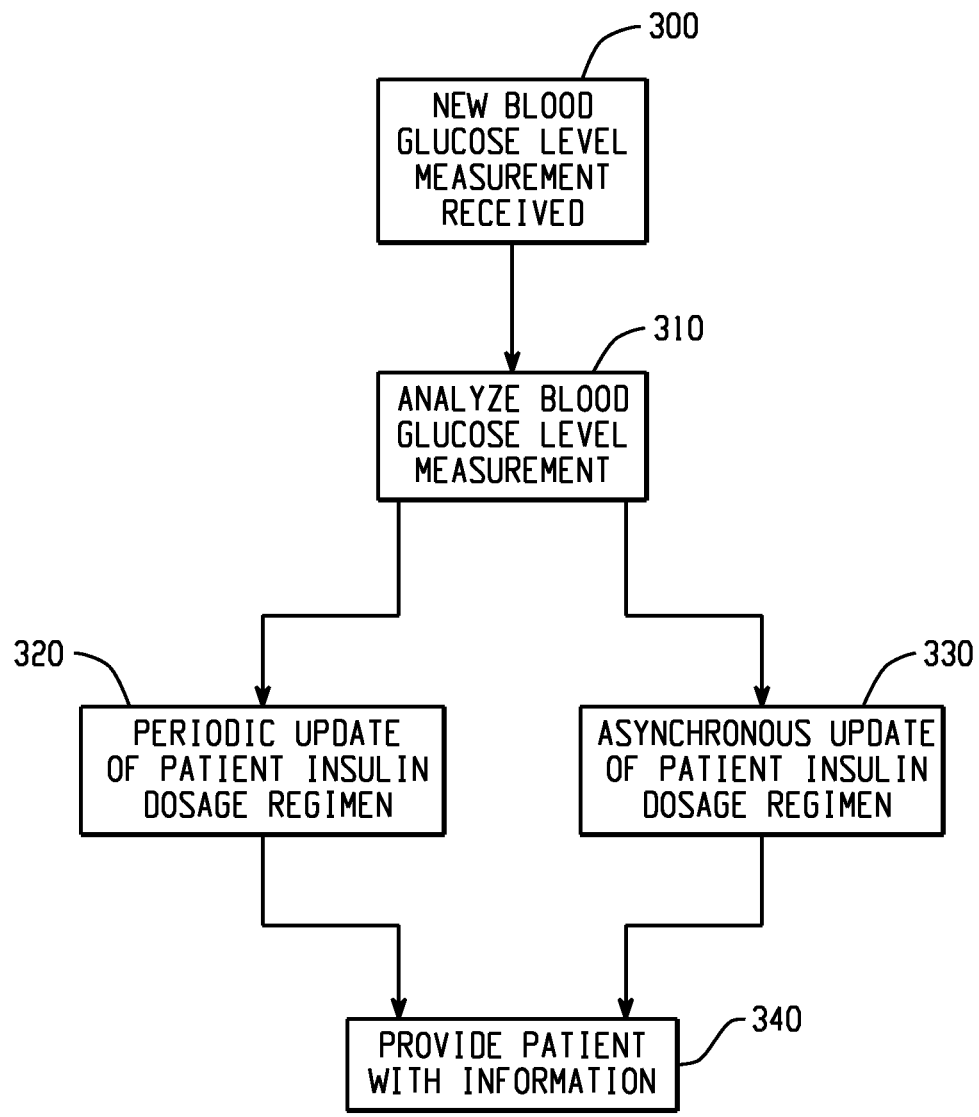
FIG. 11 is a generalized diagram of the steps employed in updating a patient's insulin dosage regimen according to certain exemplary embodiments.

Turning now to FIG. 11, there is shown a diagram generalizing the manner in which the certain embodiments may be implemented to optimize a diabetes patient's insulin dosage regimen.

In certain embodiments, there is initially specified, such as by a healthcare professional, a patient insulin dosage regimen (comprised of, for instance, a carbohydrate ratio ("CHR"), a long-acting insulin dose, and a plasma glucose correction factor). Alternatively, the initial insulin dosage regimen can be specified using published protocols for the initiation of insulin therapy, such as, for example, the protocols published by the American Diabetes Association on Oct. 22, 2008. However specified, this insulin dosage regimen data is entered in the memory of an apparatus (including according to several of the embodiments described herein), such as by a healthcare professional, in the first instance and before the patient has made any use of the apparatus.

Thereafter, the patient will input, or there will otherwise automatically be input (such as by the glucose meter) into the memory at least data corresponding to each successive one of the patient's blood-glucose-level measurements. Upon the input of such data, the processor determines, such as via the algorithm described herein, whether and by how much to vary the patient's present insulin dosage regimen. Information corresponding to this present insulin dosage regimen is then provided to the patient so that he/she may adjust the amount of insulin they administer.

According to certain exemplary embodiments, determination of whether and by how much to vary a patient's present insulin dosage regimen is undertaken both on the basis of evaluations conducted at predefined time intervals (every 7 days, for example) as well as asynchronously to such intervals. The asynchronous determinations will evaluate the patient's blood-glucose-level data for safety each time a new blood-glucose-level measurement is received to determine whether any urgent action, including any urgent variation to the patient's present insulin dosage, is necessary.

More particularly, each time a new patient blood-glucose-level measurement is received 300 into the memory it is accessed by the processor and sorted and tagged according to the time of day the measurement was received and whether or not it is associated with a certain event, e.g., pre-breakfast, bedtime, nighttime, etc. 310. Once so sorted and tagged, the new and/or previously recorded blood-glucose-level measurements are subjected to evaluation for the need to update on the basis of the passage of a predefined period of time 320 measured by a counter, as well as the need to update asynchronously for safety 330. For instance, a very low blood glucose measurement (e.g., below 50 mg/dL) representing a severe hypoglycemic event or the accumulation of several low measurements in the past few days may lead to an update in the patient's insulin dosage regimen according to the step 330, while an update to that regimen may otherwise be warranted according to the step 320 if a predefined period of time (e.g., 7 days) has elapsed since the patient's insulin dosage regimen was last updated. In either case, the patient will be provided with information 340 corresponding to the present insulin dosage regimen (whether or not it has been changed) to be used in administering his/her insulin.

Figure 12:
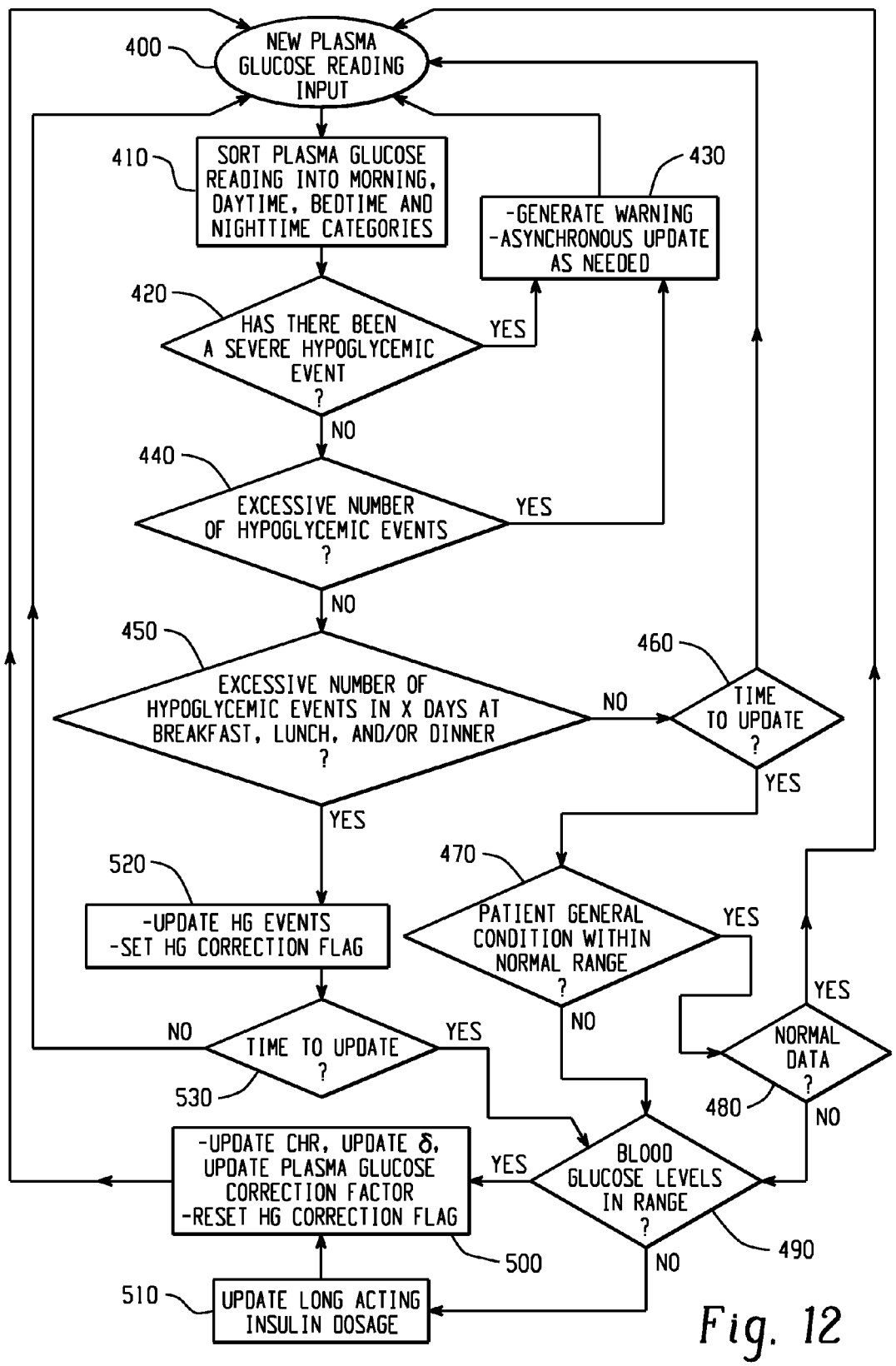
FIG. 12 is a flowchart of an exemplary algorithm employed in updating a patient's insulin dosage regimen according to certain exemplary embodiments

Referring next to FIG. 12, there is shown a flowchart that still more particularly sets forth an exemplary algorithm by which certain embodiments may be implemented to optimize a diabetes patient's insulin dosage regimen. According to the exemplary algorithm, the insulin dosage modification contemplates separate units of long-acting and short-acting insulin. However, it will be appreciated that certain embodiments are equally applicable to optimize the insulin dosage regimen of a patient where that dosage is in another conventional form (such as pre-mixed insulin). It will also be understood from this specification that certain embodiments may be implemented otherwise than as particularly described herein below.

According to a first step 400, data corresponding to a patient's new blood-glucose-level measurement is input, such as, for instance, by any of the exemplary means mentioned above, into the at least first memory (not shown in FIG. 12). This data is accessed and evaluated (by the processor) at step 410 of the exemplary algorithm and sorted according to the time it was input.

More particularly according to this step 410, the blood-glucose-level measurement data input is "tagged" with an identifier reflective of when the reading was input; specifically, whether it is a morning (i.e., "fast") measurement (herein "MPG"), a pre-lunch measurement (herein "BPG"), a pre-dinner measurement (herein "LPG"), a bedtime measurement (herein "BTPG"), or a nighttime measurement (herein "NPG").

The "tagging" process may be facilitated using a clock internal to the processor (such as, for instance, the clock of a general purpose computer) that provides an input time that can be associated with the blood-glucose-level measurement data synchronous to its entry. Alternatively, time data (i.e., "10:00 AM," "6:00 PM," etc.) or event-identifying information (i.e., "lunchtime," "dinnertime," "bedtime," etc.) may be input by the patient reflecting when the blood-glucose-level measurement data was taken, and such information used to tag the blood-glucose-level measurement data. As a further alternative, and according to the embodiment where the blood-glucose-level measurement data are provided directly to the memory by a glucose monitor, time data may be automatically associated with the blood-glucose-level measurement data by such glucose monitor (for instance, by using a clock internal to that glucose monitor). It is also contemplated that, optionally, the user/patient may be queried (for instance at a display) for input to confirm or modify any time-tag automatically assigned a blood-glucose-level measurement data-input. Thus, for instance, a patient may be asked to confirm (via data entry means such as, for example, one or more buttons or keys, a touch-screen display, etc.) that the most recently input blood-glucose-level measurement data reflects a pre-lunch (BPG) measurement based on the time stamp associated with the input of the data. If the patient confirms, then the BPG designation would remain associated with the measurement. Otherwise, further queries of the patient may be made to determine the appropriate time designation to associate with the measurement.

It will be understood that any internal clock used to tag the blood-glucose-level measurement data may, as desired, be user adjustable so as to define the correct time for the time zone where the patient is located.

Further according to the exemplary embodiment, the various categories (e.g., DPG, MPG, LPG, etc.) into which the blood-glucose-level measurement data are more particularly sorted by the foregoing "tagging" process are as follows:

NPG—The data are assigned this designation when the time stamp is between 2 AM and 4 AM.
MPG—The data are assigned this designation when the time stamp is between 4 AM and 10 AM.
BPG—The data are assigned this designation when the time stamp is between 10 AM and 3 PM.
LPG—The data are assigned this designation when the time stamp is between 3 PM and 9 PM.
BTPG—The data are assigned this designation when the time stamp is between 9 PM and 2 AM. If the BTPG data reflect a time more than three hours after the patient's presumed dinnertime (according to a predefined time window), then these data are further categorized as a dinner compensation blood-glucose-level (herein "DPG").

According to the employment of a time stamp alone to "tag" the blood-glucose-level data inputs, it will be understood that there exists an underlying assumption that these data were in fact obtained by the patient within the time-stamp windows specified above.

Per the exemplary embodiment, if the time stamp of a blood-glucose-level measurement data-input is less than 3 hours from the measurement that preceded the last meal the patient had, it is considered biased and omitted unless it represents a hypoglycemic event.

According to the next step 420, the newly input blood-glucose-level measurement is accessed and evaluated (by the processor) to determine if the input reflects a present, severe hypoglycemic event. This evaluation may be characterized by the exemplary formula $PG(t) < w$, where $PG(t)$ represents the patient's blood-glucose-level data in mg/dL, and w represents a predefined threshold value defining a severe hypoglycemic event (such as, by way of non-limiting example, 50 mg/dL).

If a severe hypoglycemic event is indicated at step 420 then, according to the step 430, the patient's present insulin dosage regimen data (in the memory 10 [not shown in FIG. 12]) is updated as warranted and independent of the periodic update evaluation described further below. More particularly, the algorithm will in this step 430 asynchronously (that is, independent of the periodic update evaluation) determine whether or not to update the patient's insulin dosage regimen on the basis of whether the patients input blood-glucose-level data reflect the accumulation of several low glucose values over a short period of time. According to the exemplary embodiment, the dosage associated with the newly input blood-glucose-level measurement is immediately decreased. More specifically, for a severe hypoglycemic event at MPG, the long-acting insulin dosage is decreased by 20%; and for a severe hypoglycemic event at BPG the breakfast short-acting insulin dose is decreased by 20%.

The algorithm also at this step 430 updates a counter of hypoglycemic events to reflect the newly-input (at step 400) blood-glucose-level measurement. Notably, modifications to the patient's insulin dosage regimen according to this step 430 do not reset the timer counting to the next periodic update evaluation. Thus, variation in the patient's insulin dosage regimen according to this step 430 will not prevent the algorithm from undertaking the next periodic update evaluation.

Any such blood-glucose-level measurement is also entered into a hypoglycemic events database in the memory. In the exemplary embodiment, this is a rolling database that is not reset. Instead, the recorded hypoglycemic events expire from the database after a predefined period of time has elapsed; essentially, once these data become irrelevant to the patient's insulin dosage regime. Thus, by way of example only, this database may contain a record of a hypoglycemic event for 7 days.

Further according to the step 430, one or more warnings may be generated for display to the patient (such as via a display 30 [not shown in FIG. 12]). It is contemplated that such one or more warnings would alert a patient to the fact that his/her blood-glucose-level is dangerously low so that appropriate corrective steps (e.g., ingesting a glucose tablet) could be taken promptly. Additionally, and without limitation, such one or more warnings may also correspond to any one or more of the following determinations:

That the patient's blood-glucose-level measurement data reflect that there have been more than two hypoglycemic events during a predetermined period of time (such as, by way of example only, in the past 7 days); that more than two drops in the patient's blood-glucose-level measurements between the nighttime measurement and the morning measurement are greater than a predetermined amount in mg/dL (70 mg/dL, for instance); and/or that more than two drops in the patient's blood-glucose-level measurement between the nighttime measurement and the morning measurement are greater than a predetermined percentage (such as, for instance, 30%).

If a severe hypoglycemic event is not indicated at step 420, the recorded (in the memory 10) data inputs corresponding to the number of patient hypoglycemic events over a predetermined period of days are accessed and evaluated by the processor (20, not shown) at step 440 to determine if there have been an excessive number of regular hypoglycemic events (e.g., a blood-glucose-level measurement between 50 mg/dL and 75 mg/dL) over that predetermined period. This evaluation is directed to determining whether the patient has experienced an excessive number of such regular hypoglycemic events in absolute time and independent of the periodic update operation as described elsewhere herein. This assessment, made at step 440, may be described by the following, exemplary formula:

$$\text{Is}(\#\{\text{of events at } HG\} > Q) \text{ or is } (\#\{\text{of hypoglycemic events in the last } W \text{ days}\} = Q)?$$

where HG represents the recorded number of hypoglycemic events, W is a predefined period of time (e.g., 3 days), and Q is a predefined number defining an excessive number of hypoglycemic events (e.g., 3). By way of example, Q may equal 3 and W may also equal 3, in which case if it is determined in step 440 that there were either 4 recorded hypoglycemic events or there were 3 recorded hypoglycemic events in the last 3 days, the algorithm proceeds to step 430.

Notably, if step 440 leads to step 430, then a binary ("1" or "0") hypoglycemic event correction "flag" is set to "1," meaning that no increase in the patient's insulin dosage regimen is allowed and the algorithm jumps to step 490 (the periodic dosage update evaluation routine). Potentially, the periodic update evaluation may concur that any or all the parts of the insulin dosage regimen require an increase due to the nature of blood-glucose-levels currently stored in the memory 10 and the execution of the different formulas described hereafter. However, by setting the hypoglycemic event correction flag to "1," the algorithm will ignore any such required increase and would leave the suggested part of the dosage unchanged. Therefore, this will lead to a potential reduction in any or all the components of the insulin dosage regimen to thus address the occurrence of the excessive number of hypoglycemic events. Further according to this step, the timer counting to the next periodic update evaluation is reset.

In the next step 450, the recorded, time-sorted/tagged blood-glucose-level measurement data corresponding to the number of patient hypoglycemic events over a predetermined period of days (for example, 7 days) are accessed and evaluated by the processor to determine if there have been an excessive number of such hypoglycemic events at any one or more of breakfast, lunch, dinner and/or in the morning over the predetermined period. This evaluation may be characterized by the exemplary formula: $\#\{HG(m)(b)(l)(d) \text{ in } XX[d]\} = Y?$; where $\#HG(m)(b)(l)(d)$ represents the number of hypoglycemic events at any of the assigned (by the preceding step) measurement times of morning, bedtime, lunch or dinner over a period of XX (in the instant example, 7) days ("[d]"), and Y represents a number of hypoglycemic events that is predetermined to constitute a threshold sufficient to merit adjustment of the patient's insulin dosage regimen (in the present example, 2 hypoglycemic events). It will be appreciated that the employment of this step in the algorithm permits identification with greater specificity of possible deficiencies in the patient's present insulin dosage regimen. Moreover, the further particularization of when hypoglycemic events have occurred facilitates time-specific (e.g., after lunch, at bedtime, etc.) insulin dosage regimen modifications.

If an excessive number of such hypoglycemic events is not indicated at step 450, then the algorithm queries at step 460 whether or not it is time to update the patient's insulin dosage regimen irrespective of the non-occurrence of hypoglycemic events, and based instead upon the passage of a predefined interval of time (e.g., 7 days) since the need to update the patient's insulin dosage regimen was last assessed. If such an update is not indicated—i.e., because an insufficient time interval has passed—then no action is taken with respect to the patient's insulin dosage and the algorithm ends (indicated by the arrow labeled "NO") until the next blood-glucose-level measurement data are input.

If, however, an update is indicated by the fact that it has been 7 days (or other predefined interval) since the need to update the patient's insulin dosage was last evaluated, then before such update is effected the algorithm first determines, in step 470, if the patient's general condition falls within a predetermined "normal" range. This determination operation may be characterized by the exemplary formula: $xxx \leq E\{PG\} \leq yyy$; where xxx represents a lower bound for a desired blood-glucose-level range for the patient, yyy represents an upper bound for a desired blood-glucose-level range for the patient, and $E\{PG\}$ represents the mean of the patient's recorded blood-glucose-level measurements. According to the exemplary embodiment, the lower bound xxx may be predefined as 80 mg/dL, and the upper bound yyy may be predefined as 135 mg/dL.

It will be understood that the foregoing values may be other than as so specified, being defined, for instance, according to the particular country in which the patient resides. Furthermore, it is contemplated that the upper (yyy) and lower (xxx) bounds may be defined by the patient's healthcare professional, being entered, for instance, via data entry means such as described elsewhere herein.

Where the patient's general condition is outside of the predetermined "normal" range, the algorithm proceeds to step 490 where the data are evaluated to determine whether it is necessary to correct the patient's long-acting insulin dosage regimen.

Where, however, the patient's general condition is within the predetermined "normal" range, the algorithm next (step 480) queries whether the patient's recorded blood-glucose-level measurement data represent a normal (e.g., Gaussian) or abnormal distribution. This may be characterized by the exemplary formula: $-X < E\{PG^{\wedge}3\} < X$; where $E\{PG^{\wedge}3\}$ represents the third moment of the distribution of the recorded (in the memory) blood-glucose-level measurement data—i.e., the third root of the average of the cubed deviations in these data around the mean of the recorded blood-glucose-levels, and X represents a predefined limit (e.g., 5). It is contemplated that the predefined limit X should be reasonably close to 0, thus reflecting that the data ($E\{PG^{\wedge}3\}$) are well balanced around the mean.

Thus, for example, where X is 5, the data are considered to be normal when the third root of the average of the cubed deviations thereof around the mean of the recorded blood-glucose-levels is greater than −5 but less than 5. Otherwise, the data are considered to be abnormal.

Where the data are determined to be normal in step 480 (indicated by the arrow labeled "YES"), then no action is taken to update the patient's insulin dosage regimen.

However, if in step 470 the mean of all of a patient's recorded blood-glucose-level measurement data are determined to fall outside of the predetermined "normal" range, then in step 490 the algorithm evaluates whether it is necessary to correct the patient's long-acting insulin dosage regimen. This is done by evaluating whether the patient's recorded MPG and BTPG data fall within an acceptable range or, alternatively, if there is an indication that the patient's long-acting insulin dosage should be corrected due to low MPG blood-glucose-level measurements. The determination of whether the patient's MPG and BTPG data fall within a predetermined range may be characterized by the exemplary formula: $xxy \leq E\{MPG\}$, $E\{BTPG\} \leq yyx$; where xxy is a lower bound for a desired blood-glucose-level range for the patient, yyx is an upper bound for a desired blood-glucose-level range for the patient, E{MPG} represents the mean of the patient's recorded MPG blood-glucose-level measurements, and E{BTPG} represents the mean of the patient's recorded BTPG measurements. According to the exemplary embodiments, xxy may be predefined as 80 mg/dL, while yyx may be predefined as 200 mg/dL. However, it will be understood that these values may be otherwise predefined, including, as desired, by the patient's healthcare provider (being entered into the memory via data entry means, for instance).

If the determination in step 490 is positive, then update of the patient's long-acting insulin dosage (step 510) is bypassed and the algorithm proceeds to step 500, according to which the patient's short-acting insulin dosage (in the form of the carbohydrate ratio ("CHR"), a correction factor Δ, and the plasma glucose correction factor are each updated and the hypoglycemic correction "flag" reset to 0 (thus permitting subsequent modification of the insulin dosage regimen at the next evaluation thereof).

If, on the other hand, the determination in step 490 is negative, then the patient's long-acting insulin dosage is updated at step 510, along with performance of the updates specified at step 500. In either case, the process ends following such updates until new patient blood-glucose-level measurement data are input.

Updates of the long-acting insulin dosage regimen data may be characterized by the following, exemplary formulas:

$$\Delta_{up} = (1 - \alpha(2))\text{floor}\left\{\frac{\alpha(1)LD(k)}{100}\right\} + \alpha(2)\text{ceil}\left\{\frac{\alpha(1)LD(k)}{100}\right\}$$

$$\Delta_{down} = (1 - \alpha(2))\text{floor}\left\{\frac{\alpha(1)LD(k)}{200}\right\} + \alpha(2)\text{ceil}\left\{\frac{\alpha(1)LD(k)}{200}\right\}$$

If E{MPG} < $b_1$
  LD(k + 1) = LD(k) − $\Delta_{down}$
Else
  If E{MPG} > $b_2$
    LD(k + 1) = LD(k) + $\Delta_{up}$
  Else if E{MPG} > $b_3$
    LD(k + 1) = LD(k) + $\Delta_{down}$
  End
End where $\alpha(1)$ represents a percentage by which the patient's present long-acting insulin dosage regimen is to be varied, $\alpha(2)$ represents a corresponding binary value (due to the need to quantize the dosage), LD(k) represents the patient's present dosage of long-acting insulin, LD(k+1) represents the new long-acting insulin dosage, $b_1$, $b_2$, and $b_3$ represent predetermined blood-glucose-level threshold parameters in mg/dL, and E{MPG} is the mean of the patient's recorded MPG blood-glucose-level measurements.

Since a patient's insulin dosage regimen is expressed in integers (i.e., units of insulin), it is necessary to decide if a percent change (increase or decrease) in the present dosage regimen of long-acting insulin that does not equate to an integer value should be the nearest higher or lower integer. Thus, for instance, if it is necessary to increase by 20% a patient's long-acting insulin dosage regimen from a present regimen of 18 units, it is necessary to decide if the new dosage should be 21 units or 22 units. In the exemplary algorithm, this decision is made on the basis of the patient's insulin sensitivity.

Insulin sensitivity is generally defined as the average total number of insulin units a patient administer per day divided by the patient weight in kilograms. More particularly, insulin sensitivity (IS(k)) according to the exemplary algorithm may be defined as a function of twice the patient's total daily dosage of long-acting insulin (which may be derived from the recorded data corresponding to the patient's present insulin dosage regimen) divided by the patient's weight in kilograms. This is expressed in the following exemplary formula:

$$IS(k) = \frac{2 \cdot LD(k)}{KK}$$

where KK is the patient weight in kilograms.

A patient's insulin sensitivity factor may of course be approximated by other conventional means, including without reliance on entry of data corresponding to the patient's weight.

More particularly, the exemplary algorithm employs an insulin sensitivity correction factor ($\alpha_{(2\times 1)}(IS)$), a 2 entries vector, to determine the percentage at which the dosage will be corrected and to effect an appropriate rounding to the closest whole number for updates in the patient's CHR, PGR and LD. When the patient's weight is known, this determination may be characterized by the following, exemplary formula:

$$\alpha(IS) = \begin{cases} [5\ 0]', & IS(k) < y_1 \\ [10\ 0]', & y_1 \leq IS(k) < y_2 \\ [20\ 0]', & y_2 \leq IS(k) < y_3 \\ [20\ 1]', & y_3 \leq IS(k) \end{cases}$$

where $\alpha(1)$ is a percentage value of adjustment from the present to a new insulin dosage value, and $\alpha(2)$ is a binary value (i.e., 0 or 1). The value of $\alpha(2)$ is defined by the value of IS(k) in relation to a predefined percent change value (e.g., $y_1$, $y_2$, $y_3$, $y_4$) for $\alpha(1)$. Thus, in the exemplary embodiment of the algorithm: Where, for example, IS(k)<0.3, the value of $\alpha(1)$ is 5 and the value of $\alpha(2)$ is 0; where 0.3≤IS(k)<0.5, the value of $\alpha(1)$ is 10 and the value of $\alpha(2)$ is 0; where 0.5≤IS(k)<0.7, the value of $\alpha(1)$ is 20 and the value of $\alpha(2)$ is 0; and where 0.7≤IS(k), the value of $\alpha(1)$ is 20 and the value of $\alpha(2)$ is 1.

When the patient weight is unknown, the algorithm will determine a using the following alternative: $\alpha(2)$ is set to "1" if the patient long acting insulin dosage is greater than X units (where, for example X may equal 50 insulin units), and the percentage by which we adjust the dosage will be determined according to the mean of the blood-glucose-level measurements currently in memory (i.e., E{PG}) by:

$$\alpha(1) = \begin{cases} 5, & w_1 \leq E\{PG\} < w_2 \\ 10, & w_2 \leq E\{PG\} < w_3 \\ 20, & w_3 \leq E\{PG\} \end{cases}$$

where $w_1$, $w_2$ and $w_3$ each represent a predefined blood-glucose-level expressed in mg/dL (thus, for example, $w_1$ may equal 135 mg/dL, $w_2$ may equal 200 mg/dL, and $w_3$ may equal 280 mg/dL).

Returning to the exemplary formulas for updating the patient's long-acting insulin dosage, in the exemplary algorithm the decision of whether and by how much to decrease or increase a patient's long-acting insulin dosage regimen is based on the predetermined threshold parameters $b_1$, $b_2$, and $b_3$; where, by way of example only, $b_1$=80 mg/dL, $b_2$=120 mg/dL, and $b_3$=200 mg/dL. More particularly, where the mean of the patient's MPG blood-glucose-level data is less than 80 mg/dL, the new long-acting insulin dosage (LD(k+1)) is the present long-acting insulin dosage (LD(k)) minus the value of $\Delta_{down}$ (which, as shown above, is a function of the insulin sensitivity correction factors α(1) and α(2), and the patient's long-acting insulin dosage (LD(k)) and may equal half of Δ.sub.up). Otherwise, if the mean of the patient's MPG blood-glucose-level data is greater than 200 mg/dL, the new long-acting insulin dosage (LD(k+1)) is the present long-acting insulin dosage (LD(k)) plus the value of the $\Delta_{up}$ (which, as shown above, is a function of the insulin sensitivity correction factors α(1) and α(2), and the patient's long-acting insulin dosage (LD(k)). Finally, if the mean of the patient's MPG blood-glucose-level data is greater than 150 but less than 200, the new long-acting insulin dosage (LD(k+1)) is the present long-acting insulin dosage (LD(k)) plus the value of the $\Delta_{down}$.

The corrective amount Δ is calculated as a percentage of the current long-acting insulin dosage rounded according to α(2). In a particular example, if α(1)=20, α(2)=0, and the current long acting insulin dosage LD(k)=58, then Δ.sub.up equals 20% of 58, which is 11.6, rounded down to $\Delta_{up}$=11. Accordingly, the long-acting insulin dosage would be updated to LD(k+1)=58+11=69.

It will be appreciated by reference to the foregoing that in certain embodiments no "ping-pong" effect is allowed; in other words, the patient's long-acting insulin dosage may not be adjustable so that any two successive such adjusted dosages fall below and above the dosage which they immediately succeed. Thus, it is not permitted to have the outcome where the latest LD update (LD(2)) is greater than the initial LD set by the healthcare professional (LD(0)), and the preceding LD update (LD(1)) is less than LD(0). Thus, the outcome LD(2)>LD(0)>LD(1) is not permitted in certain embodiments.

Returning to the step 450, if an excessive number of hypoglycemic events at any of the time-tagged blood-glucose-level measurement data for breakfast, lunch, dinner or in the morning over the predetermined period (for instance, 7 days) are indicated from the patient's data, then at step 520 the algorithm identifies from the recorded, time-tagged data of hypoglycemic events when those events occurred in order to affect any subsequently undertaken variation to the patient's insulin dosage regimen, and also sets the binary hypoglycemic correction "flag" (e.g., "1" or "0", where 1 represents the occurrence of too many hypoglycemic events, and 0 represents the nonoccurrence of too many hypoglycemic events) to 1. The presence of this "flag" in the algorithm at this juncture prevents subsequent increases in the patient's insulin dosage regimen in the presence of too many hypoglycemic events.

Further according to this step 520, where the blood-glucose-level measurement data reflects hypoglycemic events in the morning or during the night, the algorithm identifies the appropriate modification required to any subsequent variation of the patient's insulin dosage regimen. This may be characterized by the following, exemplary formula: If #HG events in {MPG+NTPG}=X, then reduce LD by α(1)/2; where #HG is the number of recorded patient hypoglycemic events at the MPG and NTPG-designated blood-glucose-level measurements, X is a predefined value (such as, for example, 2), LD refers to the long-acting insulin dosage, and α(1) represents the aforedescribed insulin sensitivity correction factor, expressed as a percentage. Thus, α(1)/2 reflects that the patient's long-acting insulin dosage is to be reduced only by ½ of the value of α(1), if at all, where the recorded hypoglycemic events occur in the morning or overnight.

Further according to this step 520, where the blood-glucose-level measurement data reflects hypoglycemic events during the day, the algorithm identifies the appropriate modification required to any subsequent variation of the patient's insulin dosage regimen. This may be characterized by the following formula: If #HG events in {BPG or LPG or NTPG}=X, then see update 6; where #HG is the number of recorded patient hypoglycemic events at any of the BPG, LPG or NTPG time-tagged measurements, X is a predefined value (for instance, 2), and "see update Δ" refers to short-acting insulin dosage correction factor Δ incorporated into the exemplary form of the algorithm, as described herein.

Following step 520, the algorithm queries 530 whether it is time to update the patient's insulin dosage regimen irrespective of the occurrence of hypoglycemic events and based upon the passage of a predefined interval of time (by way of non-limiting example, 7 days) since the need to update the patient's insulin dosage regimen was last assessed. Thus, it is possible that a patient's insulin dosage regimen will not be updated even though the HG correction flag has been "tripped" (indicating the occurrence of too many hypoglycemic events) if an insufficient period of time has passed since the regimen was last updated.

If an insufficient period of time has passed, the process is at an end (indicated by the arrow labeled "NO") until new blood-glucose-level measurement data are input. If, on the other hand, the predefined period of time has passed, then the algorithm proceeds to the step 490 to determine if the long-acting insulin dosage has to be updated as described before followed by the update step 500, according to which the patient's short-acting insulin dosage (in the form of the carbohydrate ratio ("CHR")), the correction factor Δ, and plasma glucose correction factor are each updated and the hypoglycemic correction flag reset to 0.

According to the step 500, an update to the patient's plasma glucose correction factor ("PGR") is undertaken. This may be characterized by the following, exemplary formulas:

Calculate new PGR ("NPGR"): $NPGR = \frac{1700}{E\{DT\}}$.

Calculate difference, $\Delta = |PGR(k) - NPGR|$

If $\frac{\Delta}{PGR(k)} \leq \frac{\alpha(1)}{100}$ $\Delta = (1 - \alpha(2))\text{floor}\{\Delta\} + \alpha(2)\text{ceil}\{\Delta\}$ Else $\Delta = (1 - \alpha(2))\text{floor}\left\{\frac{\alpha(1)PGR(k)}{100}\right\} + \alpha(2)\text{ceil}\left\{\frac{\alpha(1)PGR(k)}{100}\right\}$ End $PGR(k + 1) = PGR(k) + \Delta \cdot \text{sign}(NPGR - PGR(k))$ $PGR(k + 1) = \text{quant}(PGR(k + 1), ZZ)$; Quantize correction to steps of ZZ[mg/dL].

More particularly, the new PGR ("NPGR") is a function of a predefined value (e.g., 1700) divided by twice the patient's total daily dosage of long-acting insulin in the present insulin dosage regimen. In the foregoing formulas, the value of this divisor is represented by E{DT}, since the value representing twice the patient's daily dosage of long-acting insulin in the present insulin dosage regimen is substituted as an approximation for the mean of the total daily dosage of insulin administered to the patient (which data may, optionally, be employed if they are input into the memory by an insulin pump, such as in the exemplary apparatus described above, or by the patient using data entry means). The resultant value is subtracted from the present patient PGR ("PGR(k)") to define a difference ("Δ"). If the Δ divided by the present PGR(k) is less than or equal to the value of α(1) divided by 100, then the integer value of L (by which new PGR (i.e., PGR(k+1)) is updated) is a function of the formula Δ=(1−α(2))floor{Δ}+α(2)ceil{Δ}, where α(2) is the insulin sensitivity correction factor (1 or 0), "floor" is value of Δ rounded down to the next integer, and "ceil" is the value of Δ rounded up to the next integer. If, on the other hand, the Δ divided by the present PGR(k) is greater than the value of α(1) divided by 100, then the integer value of Δ is a function of the formula $$\Delta = (1 - \alpha(2))\text{floor}\left\{\frac{\alpha(1)PGR(k)}{100}\right\} + \alpha(2)\text{ceil}\left\{\frac{\alpha(1)PGR(k)}{100}\right\},$$

where α(2) is the insulin sensitivity correction factor (1 or 0), α(1) is the percent value of the insulin sensitivity correction factor, PGR(k) is the present PGR, "floor" is value of Δ rounded down to the next integer, and "ceil" is the value of Δ rounded up to the next integer. According to either outcome, the new PGR (PGR(k+1)) is equal to the present PGR (PGR(k)) plus Δ times the sign of the difference, positive or negative, of NPGR minus PGR(k).

Furthermore, it is contemplated that the new PGR will be quantized to predefined steps of mg/dL. This is represented by the exemplary formula: PGR(k+1)=quant(PGR(k+1), ZZ) PGR(k+1)=quant(PGR(k+1), ZZ); where, by way of a non-limiting example, ZZ may equal 5.

Also according to the update step 500, updates to the patient's short-acting insulin dosage regimen are undertaken by modifying the carbohydrate ratio (CHR). CHR represents the average carbohydrate to insulin ratio that a patient needs to determine the correct dose of insulin to inject before each meal. This process may be characterized by the following, exemplary formulas:

---

Calculate new CHR ("NCHR"), $NCHR = \frac{500}{E\{DT\}}$

Calculate difference, Δ = |CHR(k) − NCHR|

If $\frac{\Delta}{CHR(k)} \leq \frac{\alpha(1)}{100}$

Δ = (1−α(2))floor{Δ} +α(2)ceil{Δ}
Else $\Delta = (1 - \alpha(2))\text{floor}\left\{\frac{\alpha(1)CHR(k)}{100}\right\} + \alpha(2)\text{ceil}\left\{\frac{\alpha(1)CHR(k)}{100}\right\}$ End
CHR(k + 1) = CHR(k) + Δ · sign(NCHR − CH(k))

---

More particularly, the new CHR ("NCHR") is a function of a predefined value (e.g., 500) divided by twice the patient's total daily dosage of long-acting insulin in the present insulin dosage regimen. In the foregoing formulas, the value of this divisor is represented by E{DT}, since the value representing twice the patient's daily dosage of long-acting insulin in the present insulin dosage regimen is substituted as an approximation for the mean of the total daily dosage of insulin administered to the patient (which data may, optionally, be employed if they are input into the memory by an insulin pump, such as in the exemplary apparatus described above, or by the patient using data entry means). The resultant value is subtracted from the present patient CHR ("CHR(k)") to define a difference ("Δ"). If the Δ divided by the present CHR(k) is less than or equal to the value of α(1) divided by 100, then the integer value of Δ (by which new CHR (i.e., CHR(k+1)) is updated) is a function of the formula Δ=(1−α(2))floor{Δ}+α(2)ceil{Δ}, where α(2) is the insulin sensitivity correction factor (1 or 0), "floor" is value of Δ rounded down to the next integer, and "ceil" is the value of Δ rounded up to the next integer. If, on the other hand, the Δ divided by the present CHR(k) is greater than the value of α(1) divided by 100, then the integer value of Δ is a function of the formula $$\Delta = (1 - \alpha(2))\text{floor}\left\{\frac{\alpha(1)CHR(k)}{100}\right\} + \alpha(2)\text{ceil}\left\{\frac{\alpha(1)CHR(k)}{100}\right\},$$

where α(2) is the insulin sensitivity correction factor (1 or 0), α(1) is the percent value of the insulin sensitivity correction factor, CHR(k) is the present CHR, "floor" is value of Δ rounded down to the next integer, and "ceil" is the value of Δ rounded up to the next integer. According to either outcome, the new CHR (CHR(k+1)) is equal to the present CHR (CHR(k)) plus Δ times the sign of the difference, positive or negative, of NCHR minus CHR(k).

As patients may respond differently to doses of short-acting insulin depending upon the time of day the injection is made, a different dose of insulin may be required to compensate for a similar amount of carbohydrates consumed for breakfast, lunch, or dinner. For example, one may administer '1' insulin unit for every '10' grams of carbohydrates consumed at lunch while administering '1' insulin unit for every '8' grams of carbohydrates consumed at dinner. In the exemplary embodiment of the algorithm, this flexibility is achieved by the parameter Delta, δ, which is also updated in the step 500. It will be understood that the carbohydrate to insulin ratio (CHR) as calculated above is the same for all meals. However, the actual dosage differs among meals (i.e., breakfast, lunch, dinner) and equals CHR-δ. Therefore, the exemplary algorithm allows the dosage to be made more effective by slightly altering the CHR with δ to compensate for a patient's individual response to insulin at different times of the day.

Delta δ is a set of integers representing grams of carbohydrates, and is more specifically defined as the set of values [δb, δl, δd], where "b" represents breakfast, "l" represents lunch, and "d" represents dinner. Delta, δ, may be either positive—thus reflecting that before a certain meal it is desired to increase the insulin dose—or negative—thus reflecting that due to hypoglycemic events during the day it is desired to decrease the insulin dose for a given meal.

Initially, it is contemplated that each δ in the set [δb, δl, δd] may be defined by the patient's healthcare professional or constitute a predefined value (e.g., δ=[0, 0, 0] for each of [b, l, d], or [δb, δl, δd], thus reflecting that the patient's CHR is used with no alteration for breakfast, lunch, or dinner).

The range of δ ("Rδ") is defined as the maximum of three differences, expressed as max(|δb−δl|, |δb−δl|, |δd−δl|). In addition the algorithm defines the minimal entry ("δ$_{min}$") of the set [δb, δl, δd], expressed as min(δb, δl, δd).

Any correction to the patient's CHR can only result in a new Rδ ("Rδ(k+1)") that is less than or equal to the greatest of the range of the present set of δ (Rδ(k)) or a predefined limit (D), which may, for instance, be 2, as in the exemplary embodiment.

Against the foregoing, if the number of hypoglycemic events (HG) in a given meal (b, l or d) over a predefined period (for example, 7 days) is equal to a predefined value (for instance, 2), and if the corresponding δb, δl, or δd is not equal to the $\delta_{min}$ or the range is 0 ($R_\delta$=0), then the decrease in that $\delta$ ($\delta$b, $\delta$l, or $\delta$d) is equal to the present value for that $\delta$ minus a predefined value ("d"), which may, for instance, be 1; thus, $\delta_{\{i\}} = \delta_{\{i\}} - d$.

Otherwise, if the corresponding $\delta$b, $\delta$l, or $\delta$d is equal to the $\delta$.sub.min and the range is other than 0, then the decrease in that $\delta$ (e.g., $\delta$b, $\delta$l, or $\delta$d) is effected by decreasing each $\delta$ in the set (i.e., [$\delta$b, $\delta$l, or $\delta$d]) by the predefined value "d" (e.g., 1); thus, $\delta = \delta - d$ (where $\delta$ refers to the entire set [$\delta$b, $\delta$l, or $\delta$d]).

If, on the other hand, the number of hypoglycemic events stored in the memory is insignificant, it may be necessary to increase Δ in one or more of the set (i.e., [$\delta$b, $\delta$l, or $\delta$d]). To determine if an increase is due, the algorithm looks for an unbalanced response to insulin between the three meals (b, l, d). A patient's response to his/her recent short-acting insulin dosage is considered unbalanced if the mean blood-glucose-level measurements associated with two of the three meals falls within a predefined acceptable range (e.g., $>\alpha_1$ but $<\alpha_2$; where, for instance, $\alpha_1$=80 and $\alpha_2$=120), while the mean of the blood-glucose-level measurements associated with the third meal falls above the predefined acceptable range.

If the mean for two meals falls within [$\alpha_1$, $\alpha_2$], while the mean of the third meal is $>\alpha_2$, then the $\delta$ values for the updated set [$\delta$b, $\delta$l, or $\delta$d] are defined by the following, exemplary formulas:

$$\delta_{tmp} = \delta;$$

$$\delta_{tmp}(i) = \delta_{tmp}(i) + d;$$

If $(R_{\delta-tmp} <= R_\delta)$ or $(R_{\Delta-tmp} <= D)$, then $\delta = \delta_{tmp}$ According to the foregoing, a test set of [$\delta$b, $\delta$l, or $\delta$d], designated $\delta_{tmp}$, is defined, wherein the value of each of $\delta$b, $\delta$l, and $\delta$d equals the present value of each corresponding $\delta$b, $\delta$l, and $\delta$d. The $\delta$ value in the test set corresponding to the meal (b, l, or d) where the blood-glucose-level measurement was determined to exceed the predefined acceptable range (e.g., $>\alpha_2$) is then increased by the value "d" (e.g., 1), and the new set is accepted if it complies with one of the statements: $R_{\delta-tmp} <= R\delta$ (i.e., is the range $R_\delta$ of the test set ("$R_{\delta-tmp}$") less than or equal to the range ($R_\delta$) of the present set; or $R_{\delta-tmp} <= D$ (i.e., is the range R.sub.Δ of the test set ("$R_{\delta-tmp}$") less than or equal to the predefined value "D" (e.g., 2).

The foregoing will thus yield an increase in the insulin dosage for a particular meal if the patient's mean blood-glucose-level measurement data are outside of a predetermined range, such as, by way of example only, between $\alpha_1$=80 and $\alpha_2$=120.

Further according to this step 500, the binary hypoglycemic correction-flag is reset to 0, reflecting that the patient's insulin dosage regimen has been updated (and thus may be updated again at the next evaluation).

It will be appreciated that the PGR and CHR values determined at step 500 may optionally be employed by the processor to calculate, per conventional formulas, a "sliding scale"-type insulin dosage regimen. Such calculations may employ as a basis therefore a predefined average number of carbohydrates for each meal. Alternatively, data corresponding to such information may be input into the memory by the patient using data entry means.

Per the exemplary algorithm as described above, it will be appreciated that if a hypoglycemic event causes some dosage reduction, no other dosage can go up at the next update cycle, with respect to certain embodiments.

It should be noted that, according to certain exemplary embodiments of the algorithm herein described, any time a periodic evaluation of the patient insulin dosage regimen is undertaken, the algorithm treats the insulin dosage regimen as having been updated even if there has been no change made to the immediately preceding insulin dosage regimen. And, moreover, any time the insulin dosage regimen is updated, whether in consequence of a periodic update evaluation or an asynchronous update, the timer counting to the next periodic update evaluation will be reset to zero.

As noted, in operation of certain embodiments, there is initially specified by a healthcare professional a patient insulin dosage regimen comprised of, for example, a long-acting insulin dose component, a carbohydrate ratio component and a plasma-glucose correction factor component. This insulin dosage regimen data is entered in the memory of an apparatus, such as by a healthcare professional, in the first instance and before the patient has made any use of the apparatus. Optionally, and as necessary, the internal clock of the apparatus is set for the correct time for the time zone where the patient resides so that the time tags assigned to patient's blood-glucose-level measurements as they are subsequently input into the apparatus are accurate in relation to when, in fact, the data are input (whether automatically, manually, or a combination of both). Thereafter, the patient will input, or there will otherwise automatically be input (such as by the glucose meter) into the memory at least data corresponding to each successive one of the patient's blood-glucose-level measurements. Upon the input of such data, the processor determines, such as via the algorithm described hereinabove, whether and by how much to vary the patient's present insulin dosage regimen. Information corresponding to this present insulin dosage regimen is then provided to the patient so that he/she may adjust the amount of insulin they administer.

In the following, further embodiments are explained with the help of subsequent examples:

Example 1

A method for treating a patient's diabetes by providing treatment guidance, the method comprising: storing one or more components of the patient's insulin dosage regimen; obtaining data corresponding to the patient's blood glucose-level measurements determined at a plurality of times; tagging each of the blood glucose-level measurements with an identifier reflective of when or why the reading was obtained; and determining the patient's current glycemic state relative to a desired balance point; and determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before increasing the frequency of hypoglycemic events above a predetermined threshold.

Example 2

The method of Example 1, wherein the adjustment to the patient's insulin dosage regimen is performed in substantially real time.

Example 3

The method of Example 1 wherein an initial insulin dosage regimen is provided by a physician or other healthcare professional

Example 4

The method of Example 1, wherein the method is performed without any intervention from a doctor or other healthcare professional.

Example 5

The method of Example 1 wherein the patient's current balance point changes over time and the adjustment to patient's insulin dosage regimen is to get closer to the most recent desired balance point.

Example 6

The method of Example 5 wherein the patient's insulin dosage regimen is adjusted in a manner that dampens or prevents unstable oscillations.

Example 7

The method of Example 5 wherein the scope of the oscillations are reduced by ensuring that the current increase in the patient's insulin dosage regimen is less than the previous decrease in the patient's insulin dosage regimen.

Example 8

The method of Example 1 wherein the identifiers reflective of when the reading was obtained are selected from Breakfast, Lunch, Dinner, Bedtime, Nighttime, and Other.

Example 9

The method of Example 8 wherein the measurements tagged as "other" are classified based on the classification of the previous measurement and an elapsed time since the previous measurement.

Example 10

The method of Example 1 wherein the predetermined threshold is one severe hypoglycemic event.

Example 11

The method of Example 10 wherein the severe hypoglycemic event is defined as a blood glucose-level measurement of less than 55 mg/dL.

Example 12

The method of Example 1 wherein the hypoglycemic event is defined as a blood glucose-level measurement of less than 65 mg/dL.

Example 13

The method of Example 1 wherein the predetermined threshold is three hypoglycemic events in 24 hours.

Example 14

The method of Example 1 wherein the predetermined threshold is two hypoglycemic events for the same identifier.

Example 15

The method of Example 1 wherein the predetermined threshold is more than three hypoglycemic events since the current dosage has been instated.

Example 16

A method for updating a patient's insulin dosage regimen, the method comprising: storing one or more components of the patient's insulin dosage regime; obtaining data corresponding to the patient's blood glucose-level measurements determined at a plurality of times; incrementing a timer based on at least one of the passage of a predetermined amount of time and the receipt of each blood glucose-level measurement; tagging each of the blood glucose-level measurements with an identifier reflective of when the reading was obtained; determining for each of the obtained blood glucose-level measurements whether the measurement reflects a hypoglycemic event or a severe hypoglycemic event; and varying at least one of the one or more components in the patient's insulin dosage regime in response to a determination that the most recent blood glucose-level measurement represents a severe hypoglycemic event.

Example 17

The method of Example 16 wherein varying at least one of the one or more components in the patient's insulin dosage regime is done in response to a determination that there have been an excessive number of hypoglycemic events over a predefined period of time; and the timer is reset.

Example 18

The method of Example 16 wherein the timer indicates when to perform the step of determining from a plurality of the data corresponding to the patient's blood glucose-level measurements whether and by how much to vary at least one of the one or more components in the patient's present insulin dosage regimen; and the timer is reset.

Example 19

The method of Example 16 wherein the severe hypoglycemic event is defined as a blood glucose-level measurement of less than 50 mg/dL.

Example 18

The method of Example 17 wherein the hypoglycemic event is defined as a blood glucose-level measurement of between 50 mg/dL and 75 mg/dL.

Example 19

The method of Example 17 wherein the severe hypoglycemic events are included in the determination that there have been an excessive number of hypoglycemic events.

Example 20

The method of Example 18 wherein the timer is configured to indicate that the step of determining from a plurality of the data corresponding to the patient's blood glucose-level measurements whether and by how much to vary at least one of the one or more components in the patient's present insulin dosage regimen after 7 days.

Example 21

The method of Example 17 wherein the excessive number of hypoglycemic events over the predefined period of time is defined as a predetermined number of events in a predetermined number of days.

Example 22

The method of Example 21 wherein the excessive number of hypoglycemic events over the predetermined period of time is selected from one of the following: there have been either two hypoglycemic events with a similar identifier; three hypoglycemic events in a twenty-four hours period; or more than three hypoglycemic events since the current dosage was instated.

In the following, further embodiments of an apparatus are explained with the help of subsequent examples:

Example 23

An apparatus for treating a patient's diabetes by providing treatment guidance, the apparatus comprising: a processor; and a computer readable medium coupled to the processor; wherein the combination of the processor and the computer readable medium are configured to: store one or more components of the patient's insulin dosage regimen; obtain data corresponding to the patient's blood glucose-level measurements determined at a plurality of times; tag each of the blood glucose-level measurements with an identifier reflective of when or why the reading was obtained; determine the patient's current glycemic state relative to a desired balance point; and determine from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before increasing the frequency of hypoglycemic events above a predetermined threshold.

Example 24

The apparatus of Example 23, wherein the adjustment to the patient's insulin dosage regimen is performed in substantially real time.

Example 25

The apparatus of Example 2,3 wherein an initial insulin dosage regimen is provided by a physician or other healthcare professional.

Example 26

The apparatus of Example 23, wherein the treatment guidance is provided without any intervention from a doctor or other healthcare professional.

Example 27

The apparatus of Example 23, wherein the patient's current balance point changes over time and the adjustment to patient's insulin dosage regimen is done to get closer to the most recent desired balance point.

Example 28

The apparatus of Example 27, wherein the patient's insulin dosage regimen is adjusted in a manner that dampens, reduces, substantially prevents or prevents unstable dosage oscillations.

Example 29

The apparatus of Example 27, wherein the scope of the oscillations are reduced by ensuring that the current increase in the patient's insulin dosage regimen is less than the previous decrease in the patient's insulin dosage regimen.

Example 30

The apparatus of Example 23, wherein the identifiers reflective of when the reading was obtained are selected from Breakfast, Lunch, Dinner, Bedtime, Nighttime, and Other.

Example 31

The apparatus of Example 30, wherein the measurements tagged as "other" are classified based on the classification of the previous measurement and an elapsed time since the previous measurement.

Example 32

The apparatus of Example 23, wherein the predetermined threshold is one severe hypoglycemic event.

Example 33

The apparatus of Example 32, wherein the severe hypoglycemic event is defined as a blood glucose-level measurement of less than 55 mg/dL.

Example 34

The apparatus of Example 23, wherein the hypoglycemic event is defined as a blood glucose-level measurement of less than 65 mg/dL.

Example 35

The apparatus of Example 23, wherein the predetermined threshold is three hypoglycemic events in 24 hours.

Example 36

The apparatus of Example 23, wherein the predetermined threshold is two hypoglycemic events for the same identifier.

Example 37

The apparatus of Example 23, wherein the predetermined threshold is more than three hypoglycemic events in seven days.

Example 38

An apparatus for updating a patient's insulin dosage regimen, the apparatus comprising: a processor; and a computer readable medium coupled to the processor; wherein the combination of the processor and the computer readable medium are configured to: store one or more components of the patient's insulin dosage regime; obtain data corresponding to the patient's blood glucose-level measurements determined at a plurality of times; increment a timer based on at least one of the passage of a predetermined amount of time and the receipt of each blood glucose-level measurement; tag each of the blood glucose-level measurements with an identifier reflective of when the reading was obtained; determine for each of the obtained blood glucose-level measurements whether the measurement reflects a hypoglycemic event or a severe hypoglycemic event; vary at least one of the one or more components in the patient's insulin dosage regime in response to a determination that the most recent blood glucose-level measurement represents a severe hypoglycemic event.

Example 39

The apparatus of Example 38, wherein the decision to vary at least one of the one or more components in the patient's insulin dosage regime is done in response to a determination that there have been an excessive number of hypoglycemic events over a predefined period of time; and the timer is reset.

Example 40

The apparatus of Example 38, wherein the timer indicates when to perform the step of determining from a plurality of the data corresponding to the patient's blood glucose-level measurements whether and by how much to vary at least one of the one or more components in the patient's present insulin dosage regimen and the timer is reset.

Example 41

The apparatus of Example 38, wherein the severe hypoglycemic event is defined as a blood glucose-level measurement of less than 50 mg/dL.

Example 42

The apparatus of Example 39, wherein the hypoglycemic event is defined as a blood glucose-level measurement of between 50 mg/dL and 75 mg/dL.

Example 43

The apparatus of Example 39, wherein the severe hypoglycemic events are included in the determination that there have been an excessive number of hypoglycemic events.

Example 44

The apparatus of Example 40, wherein the timer is configured to indicate that the step of determining from a plurality of the data corresponding to the patient's blood glucose-level measurements whether and by how much to vary at least one of the one or more components in the patient's present insulin dosage regimen after 7 days.

Example 45

The apparatus of Example 38, wherein the excessive number of hypoglycemic events over a predefined period of time is defined as a predetermined number of events in a predetermined number of days.

Example 46

The apparatus of Example 45, wherein the predetermined number of days is 7 day.

Example 47

An apparatus for improving the health of a diabetic population, the apparatus comprising: a processor and a computer readable medium coupled to the processor and collectively capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before the frequency of hypoglycemic events exceeds a predetermined threshold.

Example 48

The apparatus of Example 47, wherein the percentage of patients controlled to a HbA1c of less than 7.5% is at least 80%.

Example 49

The apparatus of Examples 47 or 48, wherein the percentage of patients brought to a HbA1c of less than 7% is at least 70%.

Example 50

The apparatus of Examples 47, 48 or 49, wherein the overall healthcare management costs are reduced.

Example 51

The apparatus of Examples 47, 48 or 49, wherein the overall healthcare management costs are reduced due to a reduction in the number of hospitalizations or readmissions.

Example 52

The apparatus of Examples 47, 48 or 49, wherein the overall healthcare management costs are reduced due to a reduction in the number of emergency room visits.

Example 53

The apparatus of Examples 47 to 51, or 52 wherein there is a reduction in the frequency of hypoglycemic events within the treated population.

Example 54

The apparatus of Examples 47 to 52 or 53 wherein there the patient population mean HbA1c is reduced while the frequency of hypoglycemic events does not increase.

Example 55

The apparatus of Examples 47 to 53 or 54, wherein there is a reduction in complications within the treated population.

Example 56

The apparatus of Examples 47 to 54 or 55, wherein the percentage of patients developing secondary complications is reduced to no more than 20% over 10 years.

Example 57

The apparatus of Examples 47 to 55 or 56, wherein at least 80% of the diabetic population being treated achieves a desired balance point in a safe and effective manner.

Example 58

The apparatus of Examples 47 to 56 or 57, wherein the method results in safe and effective adjustment of treatment in at least 80% of the treated diabetic population over 10 years.

Example 59

The apparatus of Examples 47 to 57 or 58, wherein there is an 40% reduction in secondary complications over a 5 year period.

In the following, further embodiments of methods are explained with the help of subsequent examples:

Example 60

A method for improving the health of a diabetic population, the method comprising: treating a least one diabetic patient in the population using a device capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before the frequency of hypoglycemic events exceeds a predetermined threshold.

Example 61

The method of Example 60, wherein the percentage of patients controlled to a HbA1c of less than 7.5% is at least 80%.

Example 62

The methods of Examples 60 or 61, wherein the percentage of patients brought to a HbA1c of less than 7% is at least 70%.

Example 63

The methods of Examples 60, 61 or 62, wherein the overall healthcare management costs are reduced.

Example 64

The methods of Examples 60, 61 or 62, wherein the overall healthcare management costs are reduced due to a reduction in the number of hospitalizations or readmissions.

Example 65

The methods of Examples 60, 61, or 62, wherein the overall healthcare management costs are reduced due to a reduction in the number of emergency room visits.

Example 66

The methods of Examples 60, 61, 62 or 63, wherein there is a reduction in the frequency of hypoglycemic events within the treated population.

Example 67

The methods of Examples 60, 61, 62 or 63, wherein there the patient population mean HbA1c is reduced while the frequency of hypoglycemic events does not increase.

Example 68

The methods of Examples 60 to 66 or 67, wherein there is a reduction in complications within the treated population.

Example 69

The methods of Examples 60 to 67 or 68, wherein the percentage of patients developing secondary complications is reduced to no more than 20% over 10 years.

Example 70

The methods of Examples 60 to 68 or 69, wherein at least 80% of the diabetic population being treated achieves a desired balance point in a safe and effective manner.

Example 71

The methods of Examples 60 to 69 or 70, wherein the method results in safe and effective adjustment of treatment in at least 80% of the treated diabetic population over 10 years.

Example 72

The methods of Examples 60 to 70 or 71, wherein there is an 40% reduction in secondary complications over a 5 year period.

Example 73

A method for improving the health of a diabetic population, the method comprising: identifying at least one diabetic patient; treating the a least one diabetic patient to control the patient's blood glucose level; wherein the patient's blood glucose level is controlled using a device capable of: (a) storing one or more components of the patient's insulin dosage regimen; (b) obtaining data corresponding to the patient's blood glucose-level measurements determined at a plurality of times; (c) tagging each of the blood glucose-level measurements with an identifier reflective of when or why the reading was obtained; (d) determining the patient's current glycemic state relative to a desired balance point; and (e) determining from at least one of a plurality of the data corresponding to the patient's blood glucose-level measurements whether and by how much to vary at least one of the one or more components in the patient's present insulin dosage regimen to get closer to the patient's desired balance point; wherein the desired balance point is the patient's lowest blood glucose-level within a predetermined range achievable before the frequency of hypoglycemic events exceeds a predetermined threshold.

Example 74

The method of Example 73, wherein the percentage of patients brought to a HbA1c of less than 7.5% is at least 80%.

Example 75

The methods of Examples 73 or 74, wherein the percentage of patients brought to a HbA1c of less than 7% is at least 70%.

Example 76

The methods of Examples 73, 74 or 75, wherein the overall healthcare management costs are reduced.

Example 77

The methods of Examples 73, 74 or 75, wherein the overall healthcare management costs are reduced due to a reduction in the number of hospitalizations or readmissions.

Example 78

The methods of Examples 73, 74 or 75, wherein the overall healthcare management costs are reduced due to a reduction in the number of emergency room visits.

Example 79

The methods of Examples 73 to 77 or 78, wherein there is a reduction in the frequency of hypoglycemic events within the treated population.

Example 80

The methods of Examples 73 to 78 or 79, wherein there the patient population mean HbA1c is reduced while the frequency of hypoglycemic events does not increase.

Example 81

The methods of Examples 73 to 79 or 80, wherein there is a reduction in complications within the treated population.

Example 82

The methods of Examples 73 to 80 or 81, wherein the percentage of patients developing complications is reduced to no more than 20% over 10 years.

Example 83

The methods of Examples 73 to 81 or 82, wherein at least 80% of the diabetic population being treated achieves the desired balance point in a safe and effective manner.

Example 84

The methods of Examples 73 to 82 or 83, wherein the method results in safe and effective adjustment of treatment in at least 80% of the treated diabetic population over 10 years.

Example 85

The methods of Examples 73 to 83 or 84, wherein there is an 40% reduction in secondary complications over a 5 year period.

While the present disclosure has been described in connection with certain embodiments, it is to be understood that the present disclosure is not to be limited to the disclosed embodiments, but on the contrary, is intended to cover various modifications and equivalent arrangements. Also, the various embodiments described herein may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. A method for treating a patient's diabetes by providing treatment guidance, the method comprising:
   storing one or more components of the patient's insulin dosage regimen;
   obtaining data corresponding to the patient's blood glucose-level measurements determined at a plurality of times;
   initiating a timer to monitor the predetermined time period;
   incrementing the timer based on at least one of the passage of a predetermined increment of time and the receipt of at least one of the plurality of blood glucose-level measurements;
   tagging the blood glucose-level measurements with an identifier reflective of when or why the reading was obtained;
   determining, after obtaining one of the plurality of blood glucose-level measurements but before obtaining a subsequent blood glucose-level measurement, the patient's current glycemic state relative to a desired balance point; and
   determining from at least one of a plurality of the data corresponding to the patient's blood glucose-level measurements whether and by how much to vary at least one of the one or more components in the patient's present insulin dosage regimen to get closer to the patient's desired glycemic balance point;
   reducing at least one of the one or more components in the patient's insulin dosage regimen in response to the determination that the most recently obtained blood glucose-level measurement represents a severe hypoglycemic event;
   reducing at least one of the one or more components in the patient's insulin dosage regimen in response to a determination that the most recently obtained blood glucose-level measurement results in an excessive number of hypoglycemic events during the predetermined time period; wherein the timer is reinitiated after the determination that there have been an excessive number of hypoglycemic events over the predetermined amount of time; and
   determining at the end of the predetermined time period, from a plurality of the data corresponding to the patient's blood glucose-level measurements whether and by how much to vary at least one of the one or more components in the patient's present insulin dosage regimen in order to maintain the patient's blood glucose-level measurements within a predefined range; wherein the timer is reinitiated after the determination of whether and by how much to vary at least one of the one or more components in the patient's present insulin dosage regimen;

wherein the desired glycemic balance point is the patient's lowest blood glucose-level within a predetermined range achievable before increasing the frequency of hypoglycemic events above a predetermined threshold.

2. The method of claim 1, wherein the adjustment to the patient's insulin dosage regimen is performed prior to the next insulin administration after determining to change the insulin dosage regimen.

3. The method of claim 1 wherein an initial insulin dosage regimen is provided by a physician or other healthcare professional.

4. The method of claim 1, wherein the method is performed without any intervention from a doctor or other healthcare professional.

5. The method of claim 1 wherein the patient's current glycemic balance point changes over time and the adjustment to patient's insulin dosage regimen is to get closer to the most recent desired glycemic balance point.

6. The method of claim 5 wherein the patient's insulin dosage regimen is adjusted in a manner that dampens or prevents unstable oscillations.

7. The method of claim 5 wherein the scope of the oscillations are reduced by ensuring that the current increase in the patient's insulin dosage regimen is less than the previous decrease in the patient's insulin dosage regimen.

8. The method of claim 1 wherein the identifiers reflective of when the reading was obtained are selected from Breakfast, Lunch, Dinner, Bedtime, Nighttime, and Other.

9. The method of claim 8 wherein the measurements tagged with the identifier Other are classified based on the classification of the previous measurement and an elapsed time since the previous measurement.

10. The method of claim 1 wherein the predetermined threshold is one severe hypoglycemic event.

11. The method of claim 10 wherein the severe hypoglycemic event is defined as a blood glucose-level measurement of less than 55 mg/dL.

12. The method of claim 1 wherein the hypoglycemic event is defined as a blood glucose-level measurement of less than 65 mg/dL.

13. The method of claim 1 wherein the predetermined threshold is three hypoglycemic events in 24 hours.

14. The method of claim 1 wherein the predetermined threshold is two hypoglycemic events for the same identifier.

15. The method of claim 1 wherein the predetermined threshold is more than three hypoglycemic events since the current dosage has been instated.

16. An apparatus for treating a patient's diabetes by providing treatment guidance, comprising:
at least first computer-readable memory for storing one or more components of the patient's insulin dosage regimen;
at least one data input for obtaining data corresponding to the patient's blood glucose-level measurements determined at a plurality of times;
a timer for monitoring the predetermined time period;
at least one processor operatively connected to the at least first computer-readable memory, the processor programmed at least to:
initiate a timer to monitor the predetermined time period;
increment the timer based on at least one of the passage of a predetermined increment of time and the receipt of at least one of the plurality of blood glucose-level measurements;
tag the blood glucose-level measurements with an identifier reflective of when or why the reading was obtained;
determine, after obtaining one of the plurality of blood glucose-level measurements but before obtaining a subsequent blood glucose-level measurement, the patient's current glycemic state relative to a desired balance point; and
determine from at least one of a plurality of the data corresponding to the patient's blood glucose-level measurements whether and by how much to vary at least one of the one or more components in the patient's present insulin dosage regimen to get closer to the patient's desired glycemic balance point;
reduce at least one of the one or more components in the patient's insulin dosage regimen in response to the determination that the most recently obtained blood glucose-level measurement represents a severe hypoglycemic event;
reduce at least one of the one or more components in the patient's insulin dosage regimen in response to a determination that the most recently obtained blood glucose-level measurement results in an excessive number of hypoglycemic events during the predetermined time period; wherein the timer is reinitiated after the determination that there have been an excessive number of hypoglycemic events over the predetermined amount of time; and
determine at the end of the predetermined time period, from a plurality of the data corresponding to the patient's blood glucose-level measurements whether and by how much to vary at least one of the one or more components in the patient's present insulin dosage regimen in order to maintain the patient's blood glucose-level measurements within a predefined range; wherein the timer is reinitiated after the determination of whether and by how much to vary at least one of the one or more components in the patient's present insulin dosage regimen;
wherein the desired glycemic balance point is the patient's lowest blood glucose-level within a predetermined range achievable before increasing the frequency of hypoglycemic events above a predetermined threshold.

17. The apparatus of claim 1, wherein the adjustment to the patient's insulin dosage regimen is performed prior to the next insulin administration after determining to change the insulin dosage regimen.

18. The apparatus of claim 1 wherein an initial insulin dosage regimen is provided by a physician or other healthcare professional.

19. The apparatus of claim 1, wherein the method is performed without any intervention from a doctor or other healthcare professional.

20. The apparatus of claim 1 wherein the patient's current glycemic balance point changes over time and the adjustment to patient's insulin dosage regimen is to get closer to the most recent desired glycemic balance point.

21. The apparatus of claim 5 wherein the patient's insulin dosage regimen is adjusted in a manner that dampens or prevents unstable oscillations.

22. The apparatus of claim 5 wherein the scope of the oscillations are reduced by ensuring that the current increase in the patient's insulin dosage regimen is less than the previous decrease in the patient's insulin dosage regimen.

23. The apparatus of claim 1 wherein the identifiers reflective of when the reading was obtained are selected from Breakfast, Lunch, Dinner, Bedtime, Nighttime, and Other.

24. The apparatus of claim 8 wherein the measurements tagged with the identifier Other are classified based on the classification of the previous measurement and an elapsed time since the previous measurement.

25. The apparatus of claim 1 wherein the predetermined threshold is one severe hypoglycemic event.

26. The apparatus of claim 10 wherein the severe hypoglycemic event is defined as a blood glucose-level measurement of less than 55 mg/dL.

27. The apparatus of claim 1 wherein the hypoglycemic event is defined as a blood glucose-level measurement of less than 65 mg/dL.

28. The apparatus of claim 1 wherein the predetermined threshold is three hypoglycemic events in 24 hours.

29. The apparatus of claim 1 wherein the predetermined threshold is two hypoglycemic events for the same identifier.

30. The apparatus of claim 1 wherein the predetermined threshold is more than three hypoglycemic events since the current dosage has been instated.

* * * * *